US012712051B2

(12) United States Patent
Candido et al.

(10) Patent No.: US 12,712,051 B2
(45) Date of Patent: Aug. 18, 2026

(54) GEOMETRIC ATTENTION FOR BIOLOGICAL LANGUAGE REASONING

(71) Applicant: Chan Zuckerberg Biohub, Inc., Redwood City, CA (US)

(72) Inventors: Salvatore J. Candido, San Francisco, CA (US); Roshan M. Rao, Brooklyn, NY (US); Zeming Lin, Long Island City, NY (US); Alexander W. Rives, Brooklyn, NY (US); Thomas F. Hayes, San Francisco, CA (US)

(73) Assignee: Chan Zuckerberg Biohub, Inc., Redwood City, CA (US)

( * ) Notice: Subject to any disclaimer, the term of this patent is extended or adjusted under 35 U.S.C. 154(b) by 0 days.

(21) Appl. No.: 18/734,919

(22) Filed: Jun. 5, 2024

(65) Prior Publication Data

US 2025/0378912 A1 Dec. 11, 2025

(51) Int. Cl.
*G16B 40/00* (2019.01)

(52) U.S. Cl.
CPC .................................... *G16B 40/00* (2019.02)

(58) Field of Classification Search
CPC ........ G16B 30/00; G16B 40/00; G16B 30/10; G16B 5/00; G16B 15/30; G16B 15/00; G16B 15/20; G16B 45/00; G06N 3/08; G06N 20/00; G06N 3/0455; G16C 20/70; G16C 20/80
See application file for complete search history.

(56) References Cited

U.S. PATENT DOCUMENTS

| | | | | |
|---|---|---|---|---|
| 5,577,249 | A | 11/1996 | Califano | |
| 11,017,882 | B2 | 5/2021 | Cameron | |
| 11,450,407 | B1 | 9/2022 | Laniado | |
| 11,532,378 | B2 * | 12/2022 | Bepler | G06N 3/084 |
| 11,773,143 | B2 | 10/2023 | Dubois | |
| 12,211,588 | B1 | 1/2025 | Aithani | |
| 12,367,329 | B1 * | 7/2025 | Candido | G06F 30/27 |
| 2004/0083091 | A1 | 4/2004 | Ie | |
| 2005/0130224 | A1 | 6/2005 | Saito | |
| 2006/0217891 | A1 | 9/2006 | Tanuma | |
| 2007/0231329 | A1 | 10/2007 | Lazar | |
| 2008/0014646 | A1 | 1/2008 | Kuroda | |
| 2008/0215301 | A1 | 9/2008 | Eyal | |
| 2009/0006059 | A1 | 1/2009 | Arora | |
| 2009/0144209 | A1 | 6/2009 | Miyakawa | |
| 2020/0168293 | A1 | 5/2020 | Baker | |
| 2020/0342953 | A1 | 10/2020 | Morrone | |
| 2021/0090690 | A1 | 3/2021 | Plumbley | |
| 2021/0107936 | A1 | 4/2021 | Varanasi | |
| 2021/0166779 | A1 | 6/2021 | Jumper | |
| 2021/0249105 | A1 | 8/2021 | Madani | |
| 2021/0304847 | A1 | 9/2021 | Senior | |
| 2022/0036966 | A1 | 2/2022 | Meyers | |
| 2022/0104515 | A1 | 4/2022 | Hume | |
| 2022/0108766 | A1 | 4/2022 | Mackinnon | |
| 2022/0122690 | A1 * | 4/2022 | Liu | G06N 3/0455 |
| 2022/0246233 | A1 | 8/2022 | Morrone | |
| 2022/0246239 | A1 | 8/2022 | Cho | |
| 2022/0358373 | A1 * | 11/2022 | Bucher | G06N 3/045 |
| 2022/0359045 | A1 | 11/2022 | Manica | |
| 2022/0375539 | A1 | 11/2022 | Alvarez | |
| 2022/0384058 | A1 | 12/2022 | Lee | |
| 2023/0034425 | A1 | 2/2023 | Laniado | |
| 2023/0093507 | A1 | 3/2023 | Pei | |
| 2023/0110719 | A1 | 4/2023 | Krause | |
| 2023/0114905 | A1 | 4/2023 | Egertson | |
| 2023/0123770 | A1 | 4/2023 | Bepler | |
| 2023/0154573 | A1 | 5/2023 | Arijit | |
| 2023/0161996 | A1 | 5/2023 | Bepler | |
| 2023/0170059 | A1 * | 6/2023 | Gadhiya | G16C 20/10 702/27 |
| 2023/0297812 | A1 | 9/2023 | Shin | |
| 2023/0298687 | A1 | 9/2023 | Figurnov | |

(Continued)

FOREIGN PATENT DOCUMENTS

| | | | | |
|---|---|---|---|---|
| WO | 2023129955 | | 7/2023 | |
| WO | WO-2024187031 | A2 * | 9/2024 | G16B 15/30 |
| WO | WO-2025160309 | A1 * | 7/2025 | G06N 3/084 |

OTHER PUBLICATIONS

Abramson et al., Accurate structure prediction of biomolecular interactions with AlphaFold 3, Nature, vol. 630, Jun. 13, 2024, 24 pages, https://doi.org/10.1038/s41586-024-07487-w.

Alamdari et al., Protein generation with evolutionary diffusion: sequence is all you need, bioRxiv preprint, Sep. 12, 2023, pp. 1-62, https://doi.org/10.1101/2023.09.11.556673.

Alley et al., Unified rational protein engineering with sequence-based deep representation learning, Nature Methods, vol. 16, Dec. 2019, 14 pages, https://doi.org/10.1038/s41592-019-0598-1.

(Continued)

*Primary Examiner* — Mary K Zeman
(74) *Attorney, Agent, or Firm* — Van Pelt, Yi & James LLP

(57) ABSTRACT

A sequence state including representations of neighboring amino acids included in a local physical structure for a specific amino acid is received, wherein the neighboring amino acids at least include a first neighboring amino acid and a second neighboring amino acid. A direction query vector and a direction key vector are determined including by applying a first directional rotation transformation to at least a portion of a representation of the first neighboring amino acid included in the representations and applying a second directional rotation transformation to at least a portion of a representation of the second neighboring amino acid included in the representations. A direction attention result is determined including by evaluating elements of the direction query vector and the direction key vector. At least the direction attention result is used to update the sequence state for an attention mechanism of a machine learning model.

16 Claims, 25 Drawing Sheets

(56) References Cited

U.S. PATENT DOCUMENTS

| | | | | |
|---|---|---|---|---|
| 2023/0326545 | A1 | 10/2023 | Narayanan | |
| 2023/0335228 | A1 | 10/2023 | Van Hoorn | |
| 2023/0360734 | A1 | 11/2023 | Evans | |
| 2023/0368915 | A1 | 11/2023 | Abraham | |
| 2023/0386610 | A1 | 11/2023 | Singh | |
| 2023/0395186 | A1 | 12/2023 | Kohl | |
| 2023/0410938 | A1 | 12/2023 | Pritzel | |
| 2023/0420070 | A1 | 12/2023 | Wang | |
| 2023/0420084 | A1 | 12/2023 | Langevin | |
| 2024/0013854 | A1 | 1/2024 | Kyriacou | |
| 2024/0029819 | A1 | 1/2024 | Merbl | |
| 2024/0029820 | A1 | 1/2024 | Song | |
| 2024/0038337 | A1 | 2/2024 | Laniado | |
| 2024/0047012 | A1 | 2/2024 | Kozintsev | |
| 2024/0087674 | A1 | 3/2024 | Gligorijevic | |
| 2024/0087686 | A1 | 3/2024 | Pritzel | |
| 2024/0096444 | A1 | 3/2024 | Laniado | |
| 2024/0105277 | A1 | 3/2024 | Kumar | |
| 2024/0120022 | A1 | 4/2024 | Senior | |
| 2024/0145026 | A1 | 5/2024 | Zhang | |
| 2024/0153590 | A1 | 5/2024 | Essaghir | |
| 2024/0177798 | A1 | 5/2024 | Min | |
| 2024/0203523 | A1 | 6/2024 | Leem | |
| 2024/0203532 | A1 | 6/2024 | Madani | |
| 2024/0212785 | A1 | 6/2024 | El Hibouri | |
| 2024/0220685 | A1 | 7/2024 | Xu | |
| 2024/0257902 | A1 | 8/2024 | Zhao | |
| 2024/0257907 | A1 | 8/2024 | Yang | |
| 2024/0282408 | A1 | 8/2024 | Lee | |
| 2024/0321386 | A1 | 9/2024 | Evans | |
| 2024/0355413 | A1 | 10/2024 | Duplay | |
| 2024/0379248 | A1 | 11/2024 | Hemmatian | |
| 2025/0029680 | A1 | 1/2025 | Vural | |
| 2025/0210129 | A1* | 6/2025 | R | G16B 15/20 |

OTHER PUBLICATIONS

Chang et al., MaskGIT: Masked Generative Image Transformer, Proceedings of the IEEE/CVF Conference on Computer Vision and Pattern Recognition, Feb. 8, 2022, 23 pages.

Chen et al., xTrimoPGLM: Unified 100B-Scale Pre-trained Transformer for Deciphering the Language of Protein, arXiv preprint arXiv:2401.06199v1, Jan. 15, 2024, 86 pages.

Elnaggar et al., ProtTrans: Towards Cracking the Language of Life's Code Through Self-Supervised Learning, IEEE Trans Pattern Analysis & Machine Intelligence, vol. 14, No. 8, Aug. 2021, pp. 1-29.

Ferruz et al., ProtGPT2 is a deep unsupervised language model for protein design, Nature Communications, Jul. 27, 2022, pp. 1-10, https://doi.org/10.1038/s41467-022-32007-7.

Gaujac et al., Learning the Language of Protein Structure, arXiv preprint arXiv:2405.15840v1, May 24, 2024, pp. 1-20.

Heinzinger et al., Bilingual Language Model for Protein Sequence and Structure, bioRxiv preprint, Mar. 24, 2024, pp. 1-23, https://doi.org/10.1101/2023.07.23.550085.

Heinzinger et al., Modeling aspects of the language of life through transfer-learning protein sequences, BMC Bioinformatics, 2019, pp. 1-17, https://doi.org/10.1186/s12859-019-3220-8.

Hesslow et al., RITA: a Study on Scaling Up Generative Protein Sequence Models, arXiv preprint arXiv:2205.05789v2, Jul. 14, 2022, 10 pages.

Ingraham et al., Generative models for graph-based protein design, 33rd Conference on Neural Information Processing Systems (NeurIPS 2019), 2019, pp. 1-12.

Ingraham et al., Illuminating protein space with a programmable generative model, Nature, vol. 623, Nov. 30, 2023, 15 pages, https://doi.org/10.1038/s41586-023-06728-8.

Jumper et al., Highly accurate protein structure prediction with AlphaFold, Nature, vol. 596, Aug. 26, 2021, 12 pages, https://doi.org/10.1038/s41586-021-03819-2.

Li et al., DeProt: Protein language modeling with quantizied structure and disentangled attention, bioRxiv preprint, Apr. 17, 2024, 15 pages, https://doi.org/10.1101/2024.04.15.589672.

Lin et al., Evolutionary-scale prediction of atomic level protein structure with a language model, bioRxiv preprint, Oct. 31, 2022, 28 pages, https://doi.org/10.1101/2022.07.20.500902.

Lin et al., Out of Many, One: Designing and Scaffolding Proteins at the Scale of the Structural Universe with Genie 2, arXiv preprint arXiv:2405.15489v1, May 24, 2024, 27 pages.

Miyato et al., GTA: A Geometry-Aware Attention Mechanism for Multi-View Transformers, arXiv preprint arXiv:2310.10375v3, Jun. 7, 2024, 37 pages.

Nijkamp et al., ProGen2: Exploring the Boundaries of Protein Language Models, arXiv preprint arXiv:2206.13517v1, Jun. 27, 2022, 20 pages.

Rao et al., Transformer Protein Language Models Are Unsupervised Structure Learners, bioRxiv preprint, Dec. 15, 2020, 24 pages, https://doi.org/10.1101/2020.12.15.422761.

Razavi et al., Generating Diverse High-Fidelity Images with VQ-VAE-2, arXiv preprint arXiv:1906.00446v1, Jun. 2, 2019, 15 pages.

Rives et al., Biological structure and function emerge from scaling unsupervised learning to 250 million protein sequences, Proceedings of the National Academy of Sciences, vol. 118, No. 15, 2021, pp. 1-12, https://doi.org/10.1073/pnas.2016239118.

Su et al., Saprot: Protein Language Modeling with Structure-Aware Vocabulary, bioRxiv preprint, Oct. 2, 2023, 22 pages, https://doi.org/10.1101/2023.10.01.560349.

Van Den Oord et al., Neural Discrete Representation Learning, 31st Conference on Neural Information Processing Systems (NIPS 2017), 2017, 11 pages.

Van Kempen et al., Fast and accurate protein structure search with Foldseek, Nature Biotechnology, vol. 42, Feb. 2024, 17 pages, https://doi.org/10.1038/s41587-023-01773-0.

Watson et al., De novo design of protein structure and function with RFdiffusion, Nature, vol. 620, Aug. 31, 2023, 38 pages, https://doi.org/10.1038/s41586-023-06415-8.

Yu et al., Scaling Autoregressive Models for Content-Rich Text-to-Image Generation, arXiv preprint arXiv:2206.10789v1, Jun. 22, 2022, 49 pages.

Laine et al., Protein sequence-to-structure learning: Is this the end(-to-end revolution)?, HAL open science, Sep. 13, 2021, 21 pages, https://hal.science/hal-03342140v1.

Costa et al., Ophiuchus: Scalable Modeling of Protein Structures through Hierarchical Coarse-Graining SO(3)-Equivariant Autoencoders, arXiv preprint arXiv:2310.02508v2, Dec. 27, 2023, 29 pages.

Lee et al., ShapeProt: Top-down Protein Design with 3D Protein Shape Generative Model, bioRxiv preprint, Dec. 3, 2023, 19 pages, https://doi.org/10.1101/203.12.03.567710.

Liu et al., Euclidean transformers for macromolecular structures: Lessons learned, 2022 ICML Workshop on Computational Biology, 2022, 8 pages.

Luo et al., Spherical Rotation Dimension Reduction with Geometric Loss Functions, arXiv preprint arXiv:2204.10975v2, Apr. 27, 2023, 60 pages.

Pereira et al., Step-by-Step design of proteins for small molecule interaction: A review on recent milestones, Protein Science, vol. 30, Apr. 23, 2021, pp. 1502-1520, wileyonlinelibrary.com/journal/pro.

Sekmen et al., Mathematical and Machine Learning Approaches for Classification of Protein Secondary Structure Elements from Co Coordinates, Biomolecules 13, No. 6, May 3, 2023, 19 pages, https://doi.org/10.3390.biom13060923.

Wu et al., Surface-VQMAE: Vector-quantized Masked Autoencoders on Molecular Surfaces, International Conference on Machine Learning, 2024, pp. 1-16, https://openreview.net/forum?id=szxtVHOhOC.

Zhang et al., A survey on masked autoencoder for self-supervised learning in vision and beyond, Journal of Latex Class Files, vol. 14, No. 8, Aug. 2015, pp. 1-13.

Huang et al., Protein Structure Prediction: Challenges, Advances, and the Shift of Research Paradigms, Genomics Proteomics Bioinformatics, vol. 21, 2023, pp. 913-925.

Lin et al., Language models of protein sequences at the scale of evolution enable accurate structure prediction, bioRxiv preprint, Jul. 21, 2022, 31 pages, https://www.biorxiv.org/contenUIO.IIOI/2022.07.20.500902vl.

(56) References Cited

OTHER PUBLICATIONS

Xue et al., Multimodal Pre-Training Model for Sequence-Based Prediction of Protein-Protein Interaction, arXiv:2112.04814v1, Dec. 9, 2021, 13 pages, https://arxiv.Org/abs/2112.04814.
Mi et al., GDFold2: A Fast and Parallelizable Protein Folding Environment with Freely Defined Objective Functions, bioRxiv preprint, Protein sceince 34.2, Mar. 14, 2024, 29 pages.
Mi et al., GDFold2: A Fast and Parallelizable Protein Folding Environment with Freely Defined Objective Functions, bioRxiv preprint, Protein science 34.2, Nov. 11, 2024, 35 pages.
Yang et al., Masked Inverse Folding with Sequence Transfer for Protein Representation Learning, bioRxiv preprint, Protein engineering, design and selection 36, Mar. 19, 2023, 18 pages.

* cited by examiner

GEOMETRIC ATTENTION FOR BIOLOGICAL LANGUAGE REASONING

BACKGROUND OF THE INVENTION

A transformer model typically incorporates a self-attention mechanism to allow the model to weigh the dependencies and importance of different parts of an input sequence. The ability to learn long-range dependances and generate context accurate outputs makes transformers efficient for language tasks. In the context of biological languages, biological objects can be described by their properties including by their biological structure. Rather than with sentences as is commonly the case with human language, a biological structure sequence can be described in biological terms such as with atoms and bonds, etc. Therefore, when developing a large language model for biological language reasoning, there is a compelling need for a transformer attention mechanism that understands biological structure.

BRIEF DESCRIPTION OF THE DRAWINGS

Various embodiments of the invention are disclosed in the following detailed description and the accompanying drawings.

DETAILED DESCRIPTION

Figure 1:
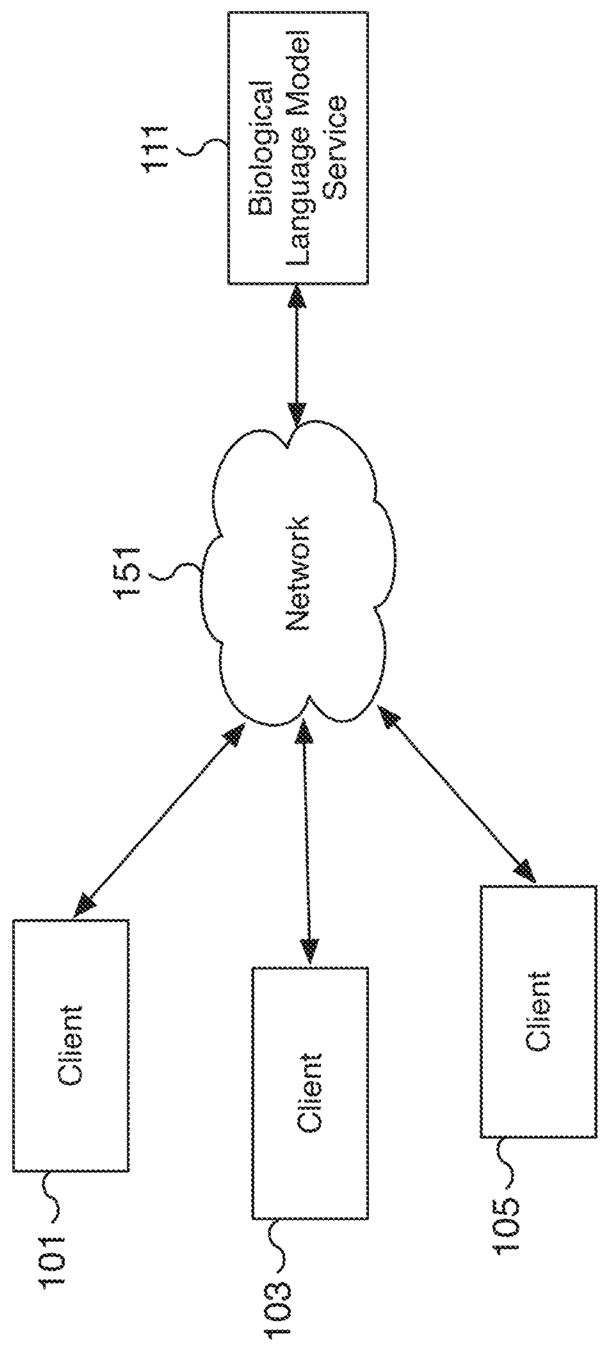
FIG. 1 is a block diagram illustrating an embodiment of a biological language reasoning platform that includes the ability to predict and generate biological language results using a biological language model.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Geometric attention for biological language reasoning is disclosed. As described herein, a geometric attention mechanism can process and learn geometric dependencies found in biological language. For example, a geometric attention mechanism can learn and accurately encoded local geometric biological structure including local structure with long-range dependances. Features of the biological structure, such as direction and distance with respect to local neighbors are extracted and learned. In various embodiments, the geometric attention mechanism can be utilized in an autoencoder model for encoding biological structure into structure tokens, where each generated structure token encodes a latent understanding of local structure. The encoded local structure can be further processed by a biological language reasoning model, by consuming structure tokens and/or by incorporating its own geometric attention mechanisms. In various embodiments, the encoded geometric structure allows the biological language reasoning model to reason on structural properties of a biological object, such as on the physical structure of a protein at the granularity of its amino acids and associated atoms.

In connection with the disclosed geometric attention mechanism, a biological language reasoning model and corresponding service platform and architecture are disclosed. As described herein, the disclosed biological language reasoning techniques and system are able to process biological queries to generate and predict biological reasoning results. For example, a biological protein language model can process protein queries to generate and predict protein sequences, structure, and/or function, among other properties of a protein. Although primarily discussed with respect to proteins, the biological language reasoning techniques are applicable to other biological language domains as well. In some embodiments, the disclosed techniques are integrated into a biological reasoning service and the capabilities of the biological language model are exposed to clients. For example, a biological reasoning service incorporating a generative and predictive biological language reasoning model can reason over protein sequence, structure, and functions simultaneously. In some embodiments, a protein query can include masked portions of a protein sequence and/or structure and the output from the biological protein language model is the unmasked protein sequence and structure. As another example, a protein query can include different masked combinations of sequence, structure, and/or function descriptions in addition to other protein properties such as secondary structure and solvent accessible surface area. When the protein query is provided to the biological reasoning service, the results are the unmasked protein properties such as a protein's predicted sequence, structure, and/or functions. In various embodiments, the disclosed biological language reasoning model captures a complex biological understanding of the specific biological domain. For example, a protein language reasoning model can capture protein sequence, structure, secondary, tertiary, and quaternary structure, and/or functions at an atomic and/or amino acid level. In various embodiments, the disclosed biological language reasoning model is a multi-track model that allows the model to respond to queries along one or more different tracks. For example, a biological protein language reasoning model can be queried to predict and/or generate a protein's amino acid sequence, structure, secondary structure, protein solvent accessible surface area, and function.

In various embodiments, the disclosed biological language reasoning model is a multi-track model that utilizes multi-directional transformers. The utilized transformers are not restricted in a specific or single direction when considering biological context, such as for a protein sequence or structure. For example, the disclosed biological language reasoning model accepts masked input at any amino acid or residue position and for multiple amino acids or residue positions with respect to a query protein. Moreover, masking can apply to one or more tracks, such as sequence, structure, and/or function tracks, among other protein tracks. In particular, the disclosed biological language reasoning model can utilize tokens for each track. For example, tokenized protein structure can be utilized for structure conditioning and/or reasoning. In some embodiments, a protein's structure is tokenized into a set of structure tokens which are understood by the protein language model. Furthermore, within the biological language model and/or tokenizer, one or more self-attention blocks that incorporate geometric reasoning are utilized. A geometric reasoning module and each instance of a disclosed geometric reasoning block can process and be used in the encoding of structure including local and/or global structure such as across local protein structure and/or across the entire protein structure. For example, for protein structure, a geometric reasoning module can encode the structure of local amino acids based on their relative distance and direction to neighboring local amino acids. In some embodiments, the neighboring amino acids are determined by physical distance allowing the geometric reasoning module to encode complex physical structure properties of proteins at a local level. Using direction and distance factors between local neighboring amino acids, self-attention scores can be determined. In some embodiments, when determining self-attention scores, the determined direction properties are attenuated based on the determined distance properties. By using the disclosed structure tokenization techniques, a protein structure can be tokenized to significantly increase the efficiency and performance of protein generation and prediction. For example, a masked protein structure can be provided as an input query to generate a corresponding unmasked protein and its unmasked structure and sequence. The generated protein sequence can be used for a variety of applications including motif scaffolding, binder design, and antibody generation, among other applications. For example, a protein can be predicted and generated by the biological language model that conforms to a desired sequence and/or pattern, including a desired partial amino acid sequence and/or a desired partial protein structure such as a particular three-dimensional shape for a portion of the protein.

In some embodiments, an amino acid sequence of a protein is tokenized into amino acid sequence tokens. For example, a query protein is presented using at least a partial sequence of the query protein and where missing amino acids may be masked. The provided protein sequence is then tokenized into amino acid sequence tokens. In some embodiments, a structure of the protein is tokenized into structure tokens. Similar to the provided protein sequence, the query protein is presented using at least a partial structure of the query protein and where missing amino acids may be masked. The provided protein structure is then tokenized into structure tokens. In some embodiments, at least a portion of the amino acid sequence tokens and at least a portion of the structure tokens are combined into a combined training sequence data set having an amino acid sequence track and a structure track, wherein at least a portion of the structure track of the combined training sequence data set is masked. For example, using a multi-track approach with at least an amino acid sequence track and a structure track, the encoded sequence and structure tokens are combined into a combined training sequence data set. On various passes, different portions including different token portions may be masked and at varying or variable mask rates. In some embodiments, a language machine learning model is trained using the combined training sequence data set to predict one or more identities of the masked structure track portion of the combined training sequence data set. For example, a biological protein language machine learning model is trained using combined training sequence data sets with portions that are masked. By training with combined training sequence data sets with one or more masked portions, the overall robustness and prediction capabilities of a biological protein language machine learning model are significantly improved. For example, the trained model can recognize proteins including by predicting one or more identities of masked portions of a query protein. Although described with respect to a model with sequence and structure tracks, additional tracks are applicable as well. For example, a biological protein language machine learning model can be trained to predict any combination of protein properties such as protein sequence, structure, secondary structure, tertiary structure, quaternary structure, functions, and solvent accessible surface areas, among other properties. In some embodiments, the predicted properties utilize a token format and are predicted as predicted property tokens, such as predicted sequence, structure, secondary structure, function, and/or solvent accessible surface areas tokens. For example, by specifying a function that a query protein should exhibit, the corresponding function tokens can be provided to a biological protein language machine learning model as an input sequence that is combined with other specified property tokens. The combined input sequence data set can be used by the biological protein language machine learning model to predict corresponding sequence tokens to determine the amino acid sequence of the protein that exhibits the function specified.

In various embodiments, a biological protein language machine learning model utilizes protein structure tokens to efficiently encode protein structure. The protein structure can be encoded using a geometric reasoning process that includes determining geometric attention scores. In some embodiments, each amino acid in a query protein is tokenized. For example, each amino acid or residue in a protein can be tokenized in parallel to generate a set of structure tokens for a query protein including for a query protein with portions that are masked. In some embodiments, for a specific amino acid in a protein, physically neighboring amino acids of the specific amino acid are determined based on physical distances with respect to the specific amino acid in a local physical protein structure. For example, based on the local structure of a specific amino acid, the closest neighboring amino acids by distance are determined. By determining the closest neighboring amino acids based on distances with respect to structure rather than by their relative positions in the amino acid sequence, a significantly more accurate representation of structure is utilized. For example, by incorporating physical distances, the determined neighbors for a specific amino acid can include amino acids that are physically close but could appear relatively far apart when examined only by their relative positions in the protein's amino acid sequence. In various embodiments, the determination of the physically neighboring amino acids accounts for the three-dimensional structure of the protein such as when different portions or ends of a protein fold onto themselves. In particular, the use of physical distances to determine neighboring amino acids accounts for amino acids that are physically close in three-dimensional space despite being separated by many intervening amino acids in the protein's amino acid sequence. In some embodiments, the physical distance values are determined based on a local reference frame of the specific amino acid. In various embodiments, the K closest neighboring amino acids are determined by distance and the number of closest K neighbors can be configurable. In some embodiments, representations of the determined physically neighboring amino acids are included in a structure encoder input for the specific amino acid. For example, the determined local representation of an amino acid including references to its local neighboring amino acids is used as input for a structure encoder used to generate structure tokens. In some embodiments, the structure encoder input is provided to an autoencoder trained using geometric loss to determine a token representing the local physical protein structure for the specific amino acid. For example, the encoder of the autoencoder can generate a latent representation of a protein's local structure and that encoded representation can be further quantized, for example, with a codebook, to generate a structure token associated with an amino acid's structure within the protein.

In various embodiments, a geometric reasoning module is used to encode biological structure such as local protein structure into structure tokens. For example, a geometric reasoning module can utilize one or more geometric attention or geometric self-attention blocks. In some embodiments, a sequence state including representations of neighboring amino acids included in a local physical structure for a specific amino acid is received, wherein the neighboring amino acids at least include a first neighboring amino acid and a second neighboring amino acid. For example, a sequence state that includes a specific amino acid and references to its nearest neighboring amino acids is generated. The sequence state can be used to encode the local structure of the amino acid including its local structure with respect to its neighboring amino acids. In various embodiments, using the sequence state, attention scores can be determined by a geometric attention block. The geometric attention block can consider direction and/or distance between amino acids when determining an attention score.

In some embodiments, a direction query vector and a direction key vector are determined including by applying a first directional rotation transformation to at least a portion of a representation of the first neighboring amino acid included in the representations and applying a second directional rotation transformation to at least a portion of a representation of the second neighboring amino acid included in the representations. For example, a pair of neighboring amino acids are transformed into the same reference coordinate system. In some embodiments, the directional rotation transformation applied is based on each amino acid's local coordinate system. In some embodiments, a direction attention result is determined including by evaluating elements of the direction query vector and the direction key vector. For example, the direction query vector and the direction key vector can be multiplied to determine a direction attention result. In some embodiments, a dot product operation is performed on the corresponding direction query vector and direction key vector element. In some embodiments, at least the direction attention result is used to update the sequence state for an attention mechanism of a machine learning model. For example, a direction attention result can be used by the attention mechanism to calculate a geometric attention result using a value vector. The geometric attention result can further utilize other factors such as a distance attention result. In some embodiments, additional operations are performed to determine the geometric attention result, such as determining a value vector, applying a rotation transformation to the determined value vector, applying a softmax or normalization function to a direction attention result or a weighted direction attention result, and transforming a result back to the local reference frame, for example, by applying an inverse rotation transformation, to determine the resulting geometric attention result.

In some embodiments, the determined direction attention result is modified by a distance attention result. For example, the direction attention result can be modulated or attenuated based on distance such as determining a greater geometric attention value when neighboring proteins are closer. In various embodiments, the resulting final attention score can be a weighted sum of the direction and distance attention scores. In some embodiments, a distance query vector and a distance key vector are determined including by applying a first distance rotation transformation and a first distance translation transformation to at least the portion of the representation of the first neighboring amino acid included in the representations and applying a second distance rotation transformation and a second distance translation transformation to at least the portion of the representation of the second neighboring amino acid included in the representations. To ensure the applied transformations are consistent, in various embodiments, the different transformations for the first and second neighboring amino acids are consistent. For example, in various embodiments, the rotation matrices of the first distance rotation transformation and the first direction rotation transformation are the same, and the rotation matrices of the second distance rotation transformation and the second direction rotation transformation are the same. Furthermore, the application of different distance rotation and translation transformations allows the distance between the two neighboring amino acids to be determined by using the same frame of reference. In some embodiments, a distance attention result is determined including by evaluating elements of the distance query vector and the distance key vector. For example, a Euclidean norm operation can be performed with the corresponding distance query vector and the distance key vector elements to determine a distance attention result. In some embodiments, the operation performed corresponds to a Euclidean norm function on the difference between query and key vector values.

In some embodiments, at least the direction attention result and the distance attention result are used to update the sequence state for an attention mechanism of a machine learning model. For example, a weighted attention result based on the direction attention result and the distance attention result can be determined. In some embodiments, the weighted attention result is determined by subtracting a weighted distance term from a weighted direction term. For example, distance and direction term weights can be learned and applied for each attention head to determine a weighted attention result. Further, a softmax or normalization function can be applied to the weighted attention result and the result multiplied by a determined value vector that has been rotated using the appropriate rotation matrices. A transformation is applied to determine the resulting attention score, for example, by applying an inverse rotation transformation to transform the result back to the local frame of reference. In various embodiments, the geometric attention result is used to update the sequence state.

FIG. 1 is a block diagram illustrating an embodiment of a biological language reasoning platform that includes the ability to predict and generate biological language results using a biological language model. In the example shown, clients 101, 103, and 105 are network clients configured to access a biological language model hosted by biological language model service 111. Clients 101, 103, and 105 are communicatively connected to biological language model service 111 via network 151. Network 151 can be a public or private network. In some embodiments, network 151 is a public network such as the Internet. Biological language model service 111 provides biological language reasoning services including a service to predict and generate biological results such as a target protein's sequence, structure, and/or functions, among other properties of a target protein. For example, using biological language model service 111 via a client such as one of clients 101, 103, or 105, a user can provide a search query for a desired protein based on a partial target protein sequence and/or structure. A protein is then generated and predicted by biological language model service 111 that matches the provided protein constraints. In some embodiments, the predicted biological results can be visualized via a graphical user interface and further synthesized, such as via a wet lab. For example, a visual graphical user interface can be provided by biological language model service 111 to visually and interactively generate a search query and to subsequently visually inspect the resulting generated biological result.

In some embodiments, clients 101, 103, and 105 are each a network client device for interfacing with biological language reasoning services hosted by biological language model service 111. For example, each of clients 101, 103, and 105 can be configured with a network software client such as a browser to access biological language reasoning services of biological language model service 111 including the ability to predict and generate biological language results such as protein search results. A biological language reasoning query can be provided by clients 101, 103, and/or 105 in various appropriate formats such as a search query, a generative language prompt, a programming language, and/or a written or visual constraint description format, etc. In various embodiments, the clients 101, 103, and 105 are further utilized to manage and interface with biological language reasoning results, such as to review, iterate on, refine, and/or modify provided search results including provided predicted and generated protein results.

In some embodiments, biological language model service 111 is a cloud service that offers functionality for performing biological language reasoning including for predicting and generating biological language results. For example, biological language model service 111 can host a biological language model such as a multi-track biological protein language model that can predict both protein sequence and protein structure based on provided protein constraints, such as a partial protein sequence and/or protein structure. In some embodiments, biological language model service 111 can predict results when provided with multiple proteins, such as a sequence of proteins. For example, biological language model service 111 can predict the structure of the two or more query proteins including how they will fold and be held together. In various embodiments, the biological language model of biological language model service 111 is trained to capture the complex biological understanding of the targeted biological domain and is conditioned on and can be queried at the atomic level. For example, for protein generation and prediction, biological language model service 111 is trained based at least on local protein structure and captures the orientation of local amino acids and their physical relationship, including distance and direction, to neighboring amino acids.

In various embodiments, a multi-track biological language model of biological language model service 111 is based on a transformer model and includes multiple transformer blocks including transformer blocks with geometric attention and geometric reasoning. Further, the model and associated tokenizers are trained with one or more specialized geometric loss functions, for example, to improve the encoding of biological structure. In some embodiments, one or more specialized geometric loss functions can be used to compute physical structural differences between neighboring atoms and/or amino acids. For example, a geometric loss function can be used to determine direction loss and a separate geometric loss function can be used to determine distance loss.

In some embodiments, in addition to protein sequence and structure tracks, a multi-track biological protein language model of biological language model service 111 includes additional tracks such as protein function, protein feature, and additional protein structure tracks. For example, a multi-track biological protein language model can include secondary, tertiary, and/or quaternary protein structure tracks and protein feature tracks for defining constraints such as solvent accessible surface area. In various embodiments, the multi-track biological language model can be trained using biological structure tokens for improved efficiency, resource utilization, and performance.

In various embodiments, biological language model service 111 may further include various user interfaces for receiving biological language reasoning queries including biological language reasoning searches. For example, in some embodiments, biological language model service 111 provides a programming language interface for describing a search query such as a protein search query. The search query can provide context for the search including constraints for the targeted results. In some embodiments, the provided user interface includes a visual component for providing constraints such as sequence, structure, and/or function constraints.

In some embodiments, biological language model service 111 is interconnected with one or more web lab services, for example, for synthesizing predicted biological results. For example, biological language model service 111 may be further integrated with a web lab such as a third-party web lab for synthesizing a predicted biological result such as a predicted protein. The integrated third-party web lab can be provided with the predicted protein sequence for synthesizing the protein, for example, by assembling the predicted amino acids of the protein.

In various embodiments, the biological language reasoning services provided by biological language model service 111 are configured as a secure environment. For example, the provided biological language reasoning computing environment can be configured to adhere to security requirements including confidentiality and integrity requirements. The provided secure environment is particularly essential when multiple parties have different interests and security requirements. For example, the implemented requirements can be imposed by the biological language reasoning service provider, clients of the biological language reasoning services, and/or be attached to and/or associated with data used by the biological language reasoning service. Other parties and their respective security interests can exist as well, and their requirements can be reflected in the implemented security model. For example, the confidentiality and integrity of data such as training data provided by different clients such as clients 101, 103, and/or 105 can be protected including by isolating access to the provided data. Different clients can utilize their respective provided additional private data such as confidential private training data for improving and/or customizing a biological language model such as a foundational model hosted by biological language model service 111. The provided data can be secured, for example, using private and public key technologies and the encryption and/or decryption of the data can be managed by a key management service of biological language model service 111. For example, data including data in encrypted form, can be provided to and received at biological language model service 111 via a secure connection. In various embodiments, the encrypted data provided to biological language model service 111 is decrypted only under certain conditions such as only within a secure enclave and with the proper authorization. For example, encrypted data provided by clients can be decrypted only within a client's isolated secure enclave of biological language model service 111. The operations associated with and the environment of a client's secure enclave can be configured to meet a required security model, such as requirements for isolated compute, memory, and/or storage. Additional requirements include requirements on access to data, access to compute and other hardware resources, access to trained models including fine-tuned models, and/or access to training pipelines, among other requirements.

In some embodiments, biological language model service 111 offers a secure environment for processing client data and hosting client customized biological language reasoning models. For example, biological language model service 111 can offer key management services for use in transferring encrypted data to a secure enclave and the associated secure enclave for processing the transferred data and hosting trained models. Client data including confidential and/or sensitive data can be deployed to the secure enclave and only decrypted within the secure enclave. A biological language model can then be trained using the decrypted data. For example, a client can provide a specific dataset of confidential data for fine-tuning a foundational biological reasoning model and/or custom settings for a model including custom and/or confidential hyperparameters. For example, the fine-tuning of a trained foundational model using techniques such as Layered Regularization with Adversarial Projection (LORA) fine-tuning can be performed securely via biological language model service 111. A fully trained model can further be deployed within the enclave for performing inference including inference in response to biological language reasoning queries. For example, a fine-tuned model can be securely accessed via a client's secure enclave hosted by biological language model service 111. In some embodiments, a client's data and trained results, such as LORA weights, are securely stored in an account separate from an account used to securely store the foundational base model. An escrow provider provides a corresponding platform, such as via biological language model service 111, for allowing the fine-tuning and model interface to be performed across the two accounts. In various embodiments, the secure enclave allows client data including fine-tuned models trained with the data to be isolated from other environments including other client environments. The secure enclave further provides a secure and isolated compute environment, for example, for performing training and/or inference tasks. In various embodiments, a client's secure enclave is configured to meet a specific security model. For example, the operating environment of the secure enclave can be configured to not contain and/or not utilize persistent storage. Other examples of configuration/deployment settings include network connectively restrictions, interactive access restrictions, remote access restrictions, access restrictions based on client and/or host profiles, access requirements such as requiring multi-factor authentication, redaction requirements, and/or dedicated and/or isolated hardware requirements including dedicated compute and memory, among other configuration/deployment settings.

Although single instances of some components have been shown to simplify the diagram of FIG. 1, additional instances of any of the components shown in FIG. 1 may exist. For example, biological language model service 111 may include one or more cloud servers such as one or more machine learning training, machine learning inference, and/or web application servers and one or more databases utilized by the cloud servers. Additionally, clients 101, 103, and 105 are example client devices for accessing and utilizing the services of biological language model service 111. Although three clients are shown (clients 101, 103, and 105), many more additional clients can exist and access the services of biological language model service 111. In some embodiments, components not shown in FIG. 1 may also exist.

Figure 2:
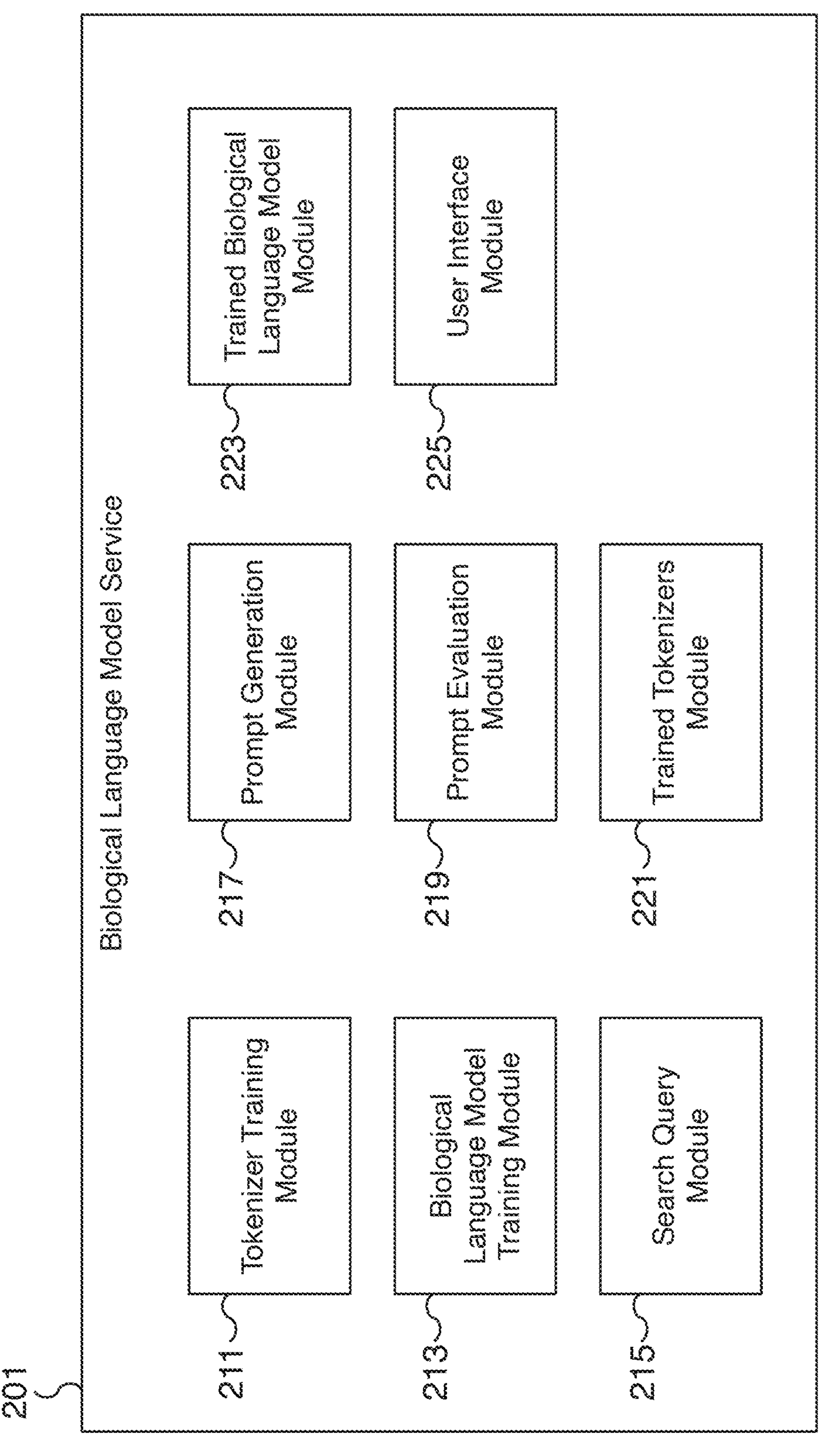
FIG. 2 is a block diagram illustrating an embodiment of a biological language model service for generating and predicting biological language reasoning results.

FIG. 2 is a block diagram illustrating an embodiment of a biological language model service for generating and predicting biological language reasoning results. In the example shown, biological language model service 201 is a cloud-based service for applying a biological language model to perform biological language reasoning. In various embodiments, the biological language model can be applicable to different biological domains such as for protein prediction and generation. Biological language model service 201 includes tokenizer training module 211, biological language model training module 213, search query module 215, prompt generation module 217, prompt evaluation module 219, trained tokenizers module 221, trained biological language model module 223, and user interface module 225. In some embodiments, biological language model service 201 is biological language model service 111 of FIG. 1. In some embodiments, the clients accessing and utilizing the services of biological language model service 201 include clients 101, 103, and/or 105 of FIG. 1.

In some embodiments, biological language model service 201 includes multiple processing modules for performing biological language reasoning. In various embodiments, one or more of the modules shown may not exist and/or additional modules may exist. In some embodiments, the functionality of one or more of the modules may be merged into a single module or split out across multiple different modules. In some embodiments, biological language model service 201 is implemented by one or more cloud servers and one or more data stores such as one or more databases including distributed databases. In some embodiments, cloud servers of biological language model service 201 can include machine learning training and inference servers as well as web application servers.

In some embodiments, tokenizer training module 211 is a processing module for training tokenizers used by biological language model service 201. For example, tokenizer training module 211 can be used to train a variety of tokenizers based on the tracks available for a multi-track biological language model of biological language model service 201. Example tokenizers can include a tokenizer for protein sequence, protein structure, and protein feature, among other protein tracks, as applicable. In some embodiments, tokenizer training module 211 is used to train a protein structure tokenizer that encodes protein structure into tokens based on the local structure of amino acids relative to neighboring amino acids. In various embodiments, the tokenized format for biological structure allows a biological language model to predict and generate biological results more efficiently and with greater emphasis resource utilization. Moreover, the trained tokenizers may be autoencoders and can include a decoding module for decoding tokens. For example, a protein structure decoder can decode protein structure tokens into a protein structure. Similarly, a protein sequence decoder can decode protein sequence tokens into a protein sequence.

In some embodiments, biological language model training module 213 is a processing module for training a multi-track biological language model of a biological language model service. For example, biological language model training module 213 can be used to train a multi-track biological protein language model to predict and generate protein language results based on masked input. In some embodiments, the different tracks can include protein sequence and protein structure tracks. Additional tracks can include secondary, tertiary, and/or quaternary protein structure tracks, protein feature tracks for defining constraints such as solvent accessible surface area, and a protein function track, among others. In various embodiments, a multi-track biological language model can be trained using biological structure tokens for improved efficiency, resource utilization, and performance, among other technological benefits. For example, protein structure can be pre-tokenized and used to train a multi-track biological protein language model using protein structure tokens. In various embodiments, the multi-track biological language model utilizes multiple multi-directional transformers and includes processing modules for geometric attention and reasoning.

In some embodiments, biological language model training module 213 includes functionality for training a multi-track biological language model using both experimental and synthetic training data. For example, experimental biological data including experimental protein sequence and structure data can be processed into training data. Similarly, synthetic biological data including predicted protein sequence and structure data generated using machine learning techniques can be processed into training data. The experimental and synthetic training data can be scored based on their respective accuracy to reflect their experimental and/or synthetic nature. By utilizing both experimental and synthetic training data, the trained model is conditioned with a greater understanding of the targeted biological language. In particular domains, such as with respect to protein structure, experimental may be scarce and the use of scored synthetic data allows a biological protein language model to develop a more thorough understanding of protein language.

In some embodiments, search query module 215 is a processing module for receiving and preparing a biological language reasoning query. Search query module 215 can support different query formats including formats based on a generative language prompt, a search query programming language, written constraint descriptions, and visual constraint descriptions, among others. In various embodiments, search query module 215 can receive and process a search query thereby preparing the query for prompt generation and subsequent prompt evaluation. For example, based on a received search query, search query module 215 can generate multiple derivative inference passes for a multi-track biological language model to narrow a search space for optimal prediction results. In some embodiments, search query module 215 along with user interface module 225 provide an interface for clients (such as clients 101, 103, and/or 105 of FIG. 1) to interface with biological language model service 201. For example, utilizing search query module 215, clients can perform searches for structure prediction, protein design, motif scaffolding, binder design, and/or antibody generation, among other biological language reasoning applications.

In some embodiments, prompt generation module 217 is a processing module for generating a generative artificial intelligence (AI) prompt for use with a biological language reasoning model of trained biological language model module 223 such as a biological protein language model. In some embodiments, the generative AI prompt is created by compiling and/or parsing a biological reasoning programming language. In some embodiments, the generative AI prompt is created by prompt evaluation module 219 using at least in part a prompt template customized for the biological language reasoning model and/or tokenizing the appropriate input using trained tokenizers module 221. For example, prompt generation module 217 can provide the appropriate context and specifics, such as tokenized sequence, structure, and/or function, for the various tracks that are applicable for a multi-track biological language reasoning model. In some embodiments, prompt generation module 217 interfaces with search query module 215 to create one or more generative AI prompts to solve a biological reasoning search query. For example, prompt generation module 217 can generate a sequence of iterative prompts including prompts based on past interference results to narrow the field of search when addressing a biological reasoning search query. In some embodiments, prompt generation module 217 can perform additional preprocessing for prompt data when generating a generative AI prompt. For example, structure data such as local amino acid structure information can be converted by prompt generation module 217 into the appropriate structure format usable by a biological language reasoning model.

In some embodiments, prompt evaluation module 219 is a processing module for evaluating a biological language generative artificial intelligence (AI) prompt using a trained biological language reasoning model of trained biological language model module 223. In some embodiments, the generative AI prompt is created by prompt generation module 217 and addresses the different tracks of a multi-track biological language reasoning model. For example, a generative AI prompt for a trained multi-track biological protein language model can be used to predict protein sequence, structure, and/or function, depending on the configured tracks of the selected model and the selectively generated masked input. In various embodiments, prompt evaluation module 219 initiates the evaluation of the generative AI prompt using the appropriate trained biological language model to generate and predict a biological language result. For example, prompt evaluation module 219 can evaluate a generative AI prompt to predict a protein sequence, structure, and/or function using a trained biological protein language model. In various embodiments, prompt evaluation module 219 interfaces with search query module 215 and/or user interface module 225 to provide biological language reasoning model inference results to a user in response to evaluating a prompt using the selected trained biological language model.

In some embodiments, trained tokenizers module 221 is a module for interfacing with trained tokenizers for use with a trained biological language model. For example, trained tokenizers module 221 includes access to multiple trained tokenizers for tokening input for different tracks of a multi-track biological language model. In some embodiments, the provided tokenizers can include a protein sequence tokenizer, a protein structure tokenizer, and/or a protein function tokenizer, among other tokenizers. In various embodiments, trained tokenizers module 221 interfaces with search query module 215, prompt generation module 217, and/or prompt evaluation module 219 to provide token results. In various embodiments, the tokenizers are trained using tokenizer training module 211.

In some embodiments, trained biological language model module 223 is a module for interfacing with a trained biological language model such as a trained biological protein language model. In various embodiments, trained biological language model module 223 can provide inference results when provided with a biological language prompt. In some embodiments, trained biological language model module 223 may utilize additional training and/or finetuning modules for improved prediction results. For example, one or more additional models in addition to a foundation biological language model can be utilized as part of an inference pipeline of trained biological language model module 223. Moreover, in various embodiments, trained biological language model module 223 can select between multiple models depending on context including based on factors such as biological domain, resource availability, configuration, accessibility, and/or cost, among other factors. For example, trained biological language model module 223 may provide different models trained for different conditions and the appropriate model is selected. In various embodiments, trained biological language model module 223 interfaces with search query module 215, prompt generation module 217, and/or prompt evaluation module 219 to provide biological language reasoning inference results. In some embodiments, trained biological language model module 223 includes access to third-party models such as a third-party structure prediction model. In various embodiments, the models of trained biological language model module 223 are trained using biological language model training module 213.

In some embodiments, user interface module 225 is a processing module for providing a user interface for interfacing with biological language model service 201. For example, user interface module 225 can provide visual, textual, and/or graphical user interfaces, among other forms of user interfaces, for exposing and utilizing the services of biological language model service 201. In some embodiments, the provided user interface is a programmatic, command-line, graphical, dialog-based, augmented reality-based, and/or virtual reality-based user interface. For example, user interface module 225 can allow users to create and execute biological language reasoning queries as well as to review, iterate on, refine, and/or modify the provided biological language reasoning results. In some embodiments, a provided graphical user interface allows a user to define a query protein and to view the predicted and generated protein in response to the protein query. In some embodiments, the interface is a programming language interface, and the user provides a programming language description of the desired query. The generated results can be further processed including by using a biological language programming language to process the received generated results as return data. In some embodiments, user interface module 225 provides an application programming interface (API) to expose the services of biological language model service 201. For example, a provided biological language model service API can allow for the automated execution of search queries by biological language model service 201.

Figure 3:
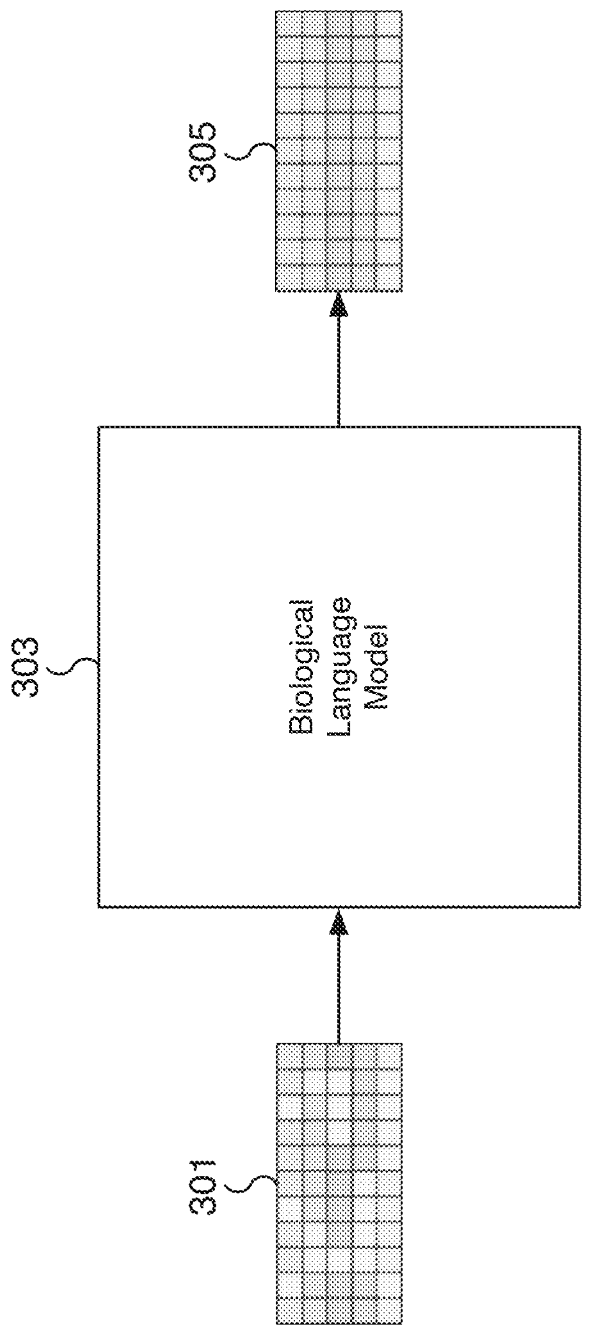
FIG. 3 is a block diagram illustrating an embodiment of a multi-track biological language reasoning model.

FIG. 3 is a block diagram illustrating an embodiment of a multi-track biological language reasoning model. In the example shown, biological language model 303 is a biological language model that receives masked multi-track input 301 and predicts multi-track output 305. In some embodiments, masked multi-track input 301 is created in response to a search query such as a search query processed by search query module 215 of FIG. 2 and converted into a generative artificial intelligence (AI) biological language prompt for biological language model 303 by prompt generation module 217 of FIG. 2. In some embodiments, the control flow for evaluating a biological language prompt by biological language model 303 is performed by prompt evaluation module 219 of FIG. 2. In some embodiments, biological language model 303 is a trained biological language model trained by biological language model training module 213 of FIG. 2 and managed by trained biological language model module 223 of FIG. 2. In some embodiments, biological language model 303 utilizes one or more tokenizers that are trained by tokenizer training module 211 of FIG. 2 and managed by trained tokenizers module 221 of FIG. 2. Although masked multi-track input 301, biological language model 303, and multi-track output 305 are described in the context of a biological protein language reasoning, other biological language domains are applicable as well based on the disclosed architecture, techniques, and platform discussed herein.

In some embodiments, masked multi-track input 301 includes masked input for each of the multiple tracks supported by biological language model 303. In the example shown, biological language model 303 can correspond to a protein language model and masked multi-track input 301 includes five protein related tracks, each with masked elements. For example, the five tracks for a protein language model can correspond to input for an amino acid sequence, primary structure, secondary structure, solvent accessible surface area, and function. In various embodiments, the input for each track is tokenized input with corresponding tokens corresponding to each amino acid of the protein for each track of masked multi-track input 301. A specification associated with a desired property of a protein, such as its sequence, structure, secondary structure, solvent accessible surface area, and function, can be converted into at one or more input tokens. For example, for the amino acid sequence of a protein, the amino acid sequence input track corresponds to amino acid sequence tokens for each unmasked amino acid sequence of the query protein, and for the primary structure of a protein, the primary structure input track corresponds to learned structure tokens for each unmasked amino acid structure of the query protein. In various embodiments, the amino acid sequence tokens can be determined by a mapping, encoding, machine learning, and/or another appropriate approach. For example, the set of known and/or supported amino acids can be mapped to a set of amino acid tokens. In some embodiments, an amino acid token vocabulary can be learned for the amino acid sequence input track. Similarly, for the secondary structure of the query protein, the secondary structure input track corresponds to secondary structure tokens for each unmasked secondary structure for each amino acid of the query protein, for function properties of the query protein, the feature input track corresponds to function tokens for unmasked features for each amino acid of the query protein, and for the solvent accessible surface area of the query protein, the solvent accessible surface area input track corresponds to solvent accessible surface area tokens for unmasked solvent accessible surface area for each amino acid of the query protein. In various embodiments, the different input tracks can apply a mapping, encoding, machine learning, and/or another appropriate approach to generate corresponding tokens. For example, a vocabulary of secondary structure elements can be determined and used to map secondary structure to secondary structure tokens. In some embodiments, a dictionary of secondary structure of proteins (DSSP) algorithm, a structural identification (STRIDE) algorithm, and/or another approach is used to generate the vocabulary of secondary structure elements for mapping to secondary structure tokens. In some embodiments, for solvent accessible surface area, a solvent accessible surface area metric can be tokenized by bucketing the solvent accessible surface area metric. For example, a float value corresponding to a depth in a protein can be binned to generate a solvent accessible surface area token. In the example shown, the boxes of masked multi-track input 301 that are blank correspond to masked input whose values will be predicted as output values in multi-track output 305 by biological language model 303. In various embodiments, when the different tracks are taken together, masked multi-track input 301 corresponds to combined input tokens that are a combined input sequence data that specify at least a portion of a protein. The combined input sequence can be provided to a biological protein language machine learning model to predict one or more missing tokens.

In some embodiments, multi-track output 305 includes the unmasked values for each amino acid's properties for each track supported by biological language model 303. For example, multi-track output 305 can include the unmasked amino acids of a corresponding masked query protein's sequence with respect to masked multi-track input 301. As another example, multi-track output 305 can include a predicted structure for masked amino acids of the structure track for a query protein with respect to masked multi-track input 301. As yet another example, multi-track output 305 can include predicted functions for masked amino acids of the function track for a query protein with respect to masked multi-track input 301. In various embodiments, biological language model 303 similarly predicts the values of corresponding masked properties for other tracks of biological language model 303 such as secondary structure and solvent accessible surface area tracks. In the example shown, multi-track output 305 shows no masked values since each corresponding masked value of masked multi-track input 301 now has a corresponding unmasked value predicted by biological language model 303. In various embodiments, the values of multi-track output 305 can be tokenized values. For example, a decoder of a trained auto-encoder tokenizer can be used to decode the predicted token value into a more accessible output result. As one particular example, a protein sequence decoder can decode predicted sequence tokens into a more convenient, accessible, and manageable protein sequence format usable for protein synthesis. Similarly, a protein structure decoder can decode predicted structure tokens into a more convenient and manageable protein structure format including one that can then be used to visualize the predicted protein structure. In some embodiments, a property token for an amino acid, such as a function token, can correspond to one or more properties such as one or more functions of the amino acid. For example, a single function token can be decoded to the set of all functions predicted for a particular amino acid of the query protein.

In some embodiments, biological language model 303 is a multi-track deep learning model that utilizes multi-directional transformers. The utilized transformers are not restricted in a specific or single direction when considering biological context, such as for a protein sequence or structure. For example, when trained for protein language reasoning, biological language model 303 can accept, via masked multi-track input 301, masked input at any amino acid or residue position for a query protein. Moreover, masking can apply to any of the tracks supported by biological language model 303, such as sequence, structure, and/or function tracks, among other protein tracks. In various embodiments, biological language model 303 can utilize tokens for each track. For example, a tokenized protein structure can be utilized for structure conditioning and/or reasoning. In some embodiments, biological language model 303 can further utilize one or more self-attention blocks that can incorporate geometric reasoning. A geometric reasoning module and each instance of a disclosed geometric reasoning block can process and be used in the encoding of a local structure. In various embodiments, in response to the provided masked multi-track input 301, a protein language reasoning version of biological language model 303 predicts the masked values of masked multi-track input 301 to generate a target protein described by multi-track output 305 in response to the query protein constrained by the unmasked values of masked multi-track input 301.

In some embodiments, although not shown in FIG. 3, biological language model 303 may receive additional forms of input other than the tokenized input tracks of masked multi-track input 301. For example, biological language model 303 may receive additional input in the form of partial structure input instead of a tokenized version of the structure. In some embodiments, a query protein structure is provided in a user-accessible format that allows users to more easily interface with biological language model 303 including by providing structure constraints in an unencoded format for the query protein. For example, local structure for amino acids of a query protein can be described using three-dimensional coordinates associated with relevant atoms. When configured to receive non-tokenized input, biological language model 303 can be structured to include one or more geometric reasoning blocks that allow the model to express an internal understanding of protein structure including local protein structure and/or structure across the entire protein. In some embodiments, although non-tokenized input is provided to the biological language model 303, the input can be tokenized as a pre-processing step such as a pre-processing step for preparing masked multi-track input 301.

In some embodiments, biological language model 303 includes one or more conditioning tracks and/or conditioning tensors. For example, a biological language program can be compiled to generate conditioning input corresponding to requirements and/or constraints for biological language model 303 to utilize during inference. In various embodiments, biological language model 303 is trained to support a biological language program specification and can include one or more conditioning tracks that can be conditioned using a biological language program based on the biological language program specification.

Figure 4:
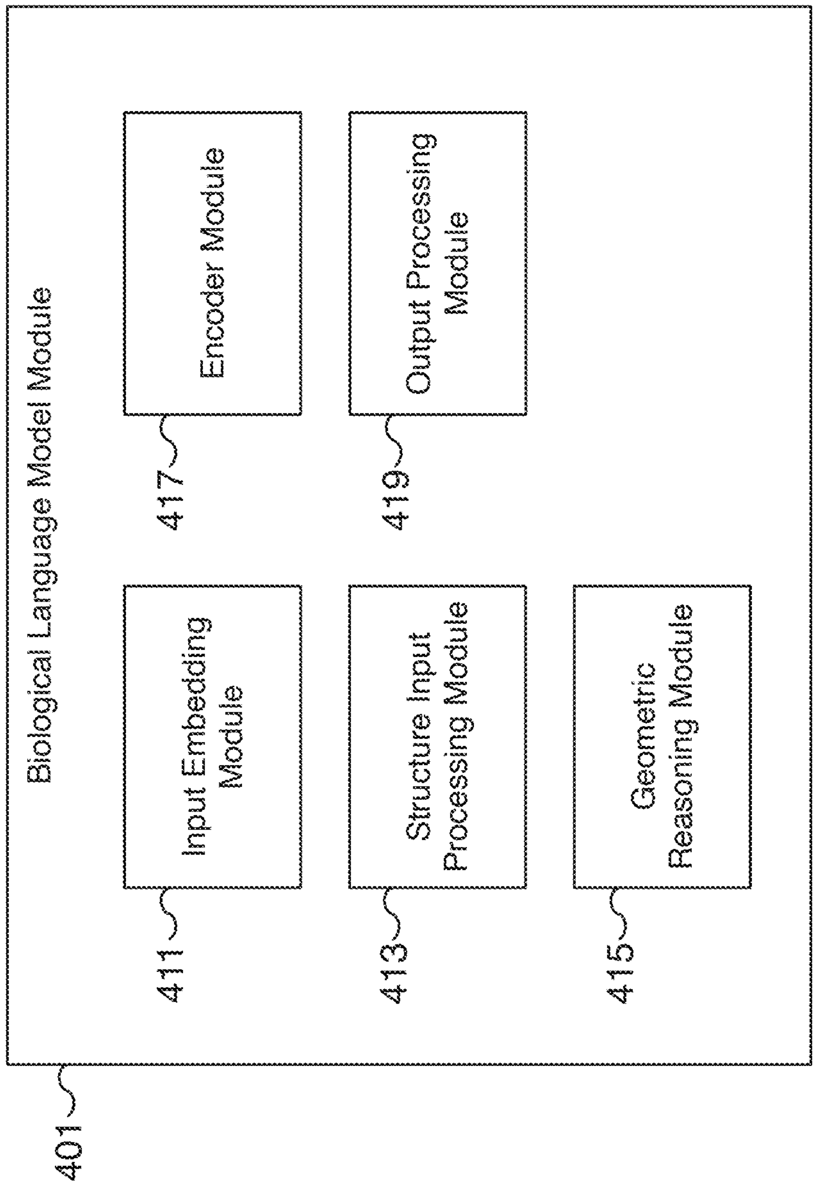
FIG. 4 is a block diagram illustrating an embodiment of a biological language model module capable of generating and predicting biological language reasoning results.

FIG. 4 is a block diagram illustrating an embodiment of a biological language model module capable of generating and predicting biological language reasoning results. In various embodiments, biological language model module 401 corresponds to components and architecture aspects for using a deep learning model to perform biological language reasoning. In the example shown, biological language model module 401 includes input embedding module 411, structure input processing module 413, geometric reasoning module 415, encoder module 417, and output processing module 419. In various embodiments, biological language model module 401 corresponds to trained biological language model module 223 of FIG. 2 and biological language model 303 of FIG. 3. For example, biological language model module 401 corresponds to at least a portion of the functionality used to train biological language model 303 of FIG. 3 and to perform inference using biological language model 303 of FIG. 3.

In some embodiments, input embedding module 411 is a processing module for embedding input provided to the model such as provided input tokens. For example, the different input tokens for the different tracks of a multi-track biological language model are embedded into embedding vectors using an embedding layer of input embedding module 411. In some embodiments, a position-wise sum operation is performed by input embedding module 411. For example, for biological protein language reasoning, the position-wise sum operation can be performed relative to each amino acid of the query protein. In various embodiments, corresponding embedding vectors based on the length L of a query protein and an embedding dimension are generated by input embedding module 411 and capture the provided semantic meaning for each of the L amino acids of the query protein.

In some embodiments, structure input processing module 413 is a processing module for processing user provided structure data. For example, structure information can be provided to a multi-track biological language model in a non-tokenized format, such as a user-accessible format that allows users to interface with a biological language model more easily. Rather than requiring biological structure be presented in a tokenized format, users can provide structure constraints in an unencoded format, including standardized structure formats. For example, for a query protein, the local structure of amino acids can be provided in a standardized and/or documented structure format. In some embodiments, the received structure input utilizes backbone frames for each amino acid including specifying relevant atoms of an amino acid based on their three-dimensional spatial coordinates. In some embodiments, the received structure input utilizes a different set of atoms for each amino acid including, for example, a set that uses all atomic coordinates for an amino acid. For non-proteins, the structure input can include coordinates for any number of relevant atoms including all atoms of at each specific position. In various embodiments, structure input processing module 413 receives the provided structure input and performs any necessary pre-processing before feeding the processed structure data to the biological language model. For example, a biological language model can be configured to receive non-tokenized structure data for conditioning on local structure. In some embodiments, the structure data is received at a transformer block configured with geometric attention.

In some embodiments, geometric reasoning module 415 is a processing module for performing geometric reasoning on structure input data. For example, geometric reasoning module 415 can be utilized to encode local structure information based on provided local structure data. In some embodiments, a transformer block of encoder module 417 can utilize geometric reasoning module 415 to perform geometric attention on provided structure data including structure data that has not been tokenized to encode local structure context. In various embodiments, geometric reasoning module 415 can include one or more of layer normalization, self-attention, geometric attention, and feed-forward blocks. For example, layer normalization can be performed prior to self-attention, geometric attention, and feed-forward processing. In some embodiments, the geometric reasoning process performed by geometric reasoning module 415 is similar to the geometric reasoning performed when tokenizing structure data.

In some embodiments, encoder module 417 is a processing module for processing the embedded semantic input generated by input embedding module 411. For example, encoder module 417 can apply attention mechanisms to the embedded input to allow the model to consider the full context of the query target such as a query protein. In various embodiments, encoder module 417 includes multiple transformer blocks including self-attention and geometric attention blocks. For example, encoder module 417 can include multiple layers of transformers, each layer applying attention mechanisms to consider, for example, the context of different amino acids of a query protein. In some embodiments, encoder module 417 includes multi-directional transformers and can unmask properties of the query object, such as a query protein, at different positions such as at different amino acid locations. At the completion of processing for encoder module 417, the output can be a set of intermediate or hidden representations for each position of the query object. In some embodiments, the outputted representations correspond to a set of output values or logits that require additional processing to generate a biological query output result.

In some embodiments, output processing module 419 is a processing module for applying an output layer to generate biological language model results. In some embodiments, output processing module 419 projects the logits corresponding to intermediate or hidden outputted representations determined by encoder module 417 for each track of the multi-track model. For example, output processing module 419 can determine sequence, structure, and function values for corresponding sequence, structure, and function tracks of a multi-track model. In various embodiments, output processing module 419 determines the multi-track output values in the format of output tokens. The output tokens can then be decoded using a decoder module of the corresponding tokenizer.

Figure 5:
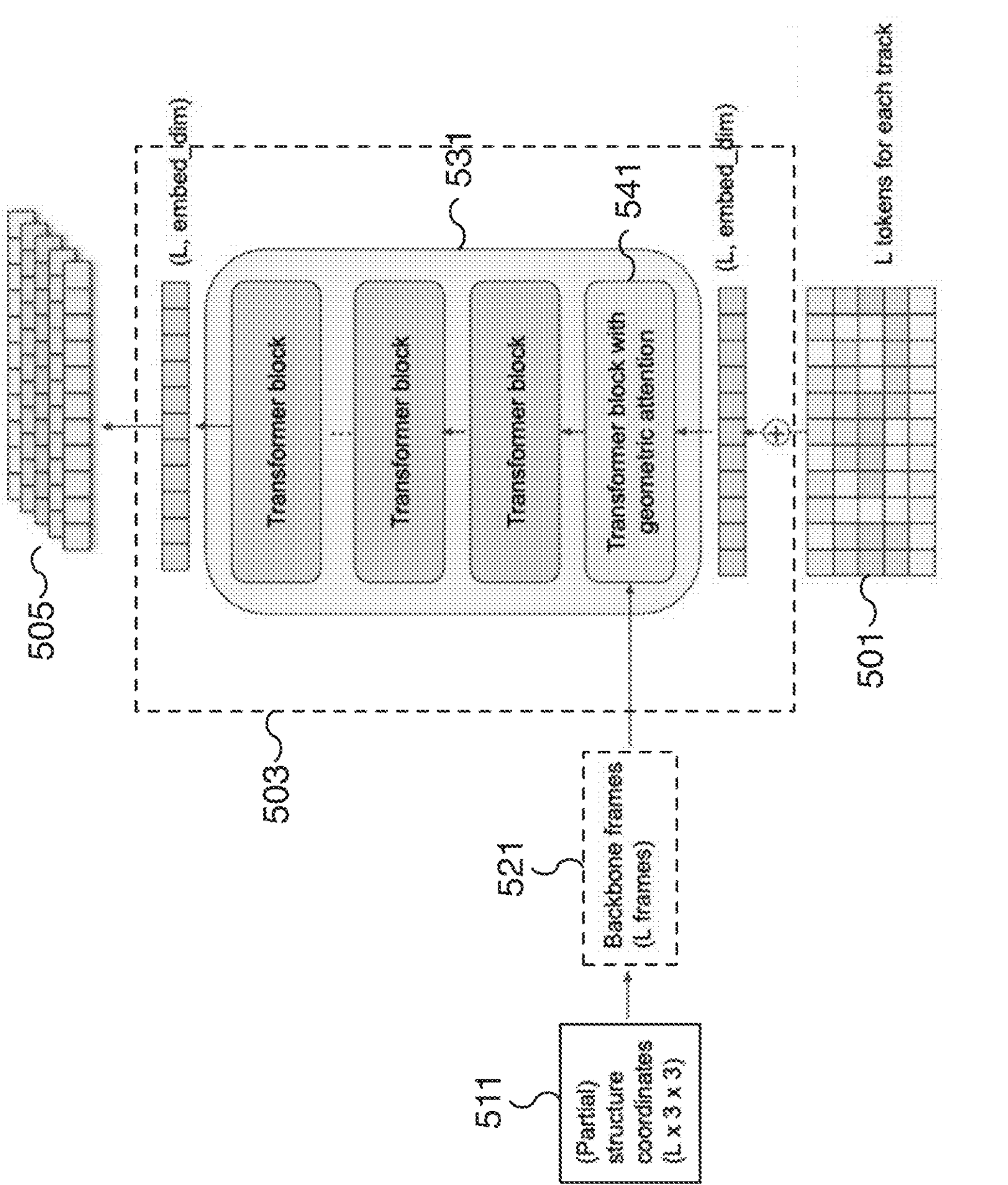
FIG. 5 is a block diagram illustrating an embodiment of a multi-track biological protein language model module capable of generating and predicting biological protein language reasoning results including structure results.

FIG. 5 is a block diagram illustrating an embodiment of a multi-track biological protein language model module capable of generating and predicting biological protein language reasoning results including structure results. In the example shown, masked multi-track input 501 is provided as input for a specific query protein to multi-track biological protein language model 503. Also shown in FIG. 5 is structure input data 511 that corresponds to the local amino acid structure data for the query protein. The query protein is described by L amino acids, each with three backbone atoms with each backbone atom described by three coordinates corresponding to X, Y, and Z coordinate values. Structure input data 511 is converted to backbone frames 521. Both masked multi-track input 501 and backbone frames 521 are received at multi-track biological protein language model 503 and used to predict query protein results corresponding to multi-track output 505. In various embodiments, backbone frames 521 is used to augment constraints specified in masked multi-track input 501.

In some embodiments, multi-track biological protein language model 503 is trained by biological language model training module 213 of FIG. 2 and the trained model is then managed by trained biological language model module 223 of FIG. 2. In some embodiments, inference with multi-track biological protein language model 503 is initiated by prompt evaluation module 219 of FIG. 2. In some embodiments, multi-track biological protein language model 503 is further implemented via biological language model module 401 of FIG. 4 and backbone frames 521 is converted by biological language model module 401 of FIG. 4. For example, structure input data 511 can be converted to backbone frames 521 by structure input processing module 413 of FIG. 4. In some embodiments, masked multi-track input 501 is masked multi-track input 301 of FIG. 3, multi-track biological protein language model 503 is biological language model 303 of FIG. 3, and/or multi-track output 505 is multi-track output 305 of FIG. 3.

As shown in FIG. 5, multi-track biological protein language model 503 includes encoder block 531 with multiple transformer blocks including transformer block with geometric attention 541 that receives backbone frames 521. In various embodiments, each of the transformer blocks of encoder block 531 can implement an attention mechanism such as a self-attention or geometric attention mechanism. In some embodiments, the embodiment of encoder block 531 is implemented by encoder module 417 of FIG. 4 and the corresponding geometric attention mechanism of the displayed transformer is implemented by geometric reasoning module 415 of FIG. 4.

In various embodiments, a position-wise sum operation is performed on masked multi-track input 501 by multi-track biological protein language model 503. For example, the L input tokens per track of masked multi-track input 501 are embedded into vectors by an embedding layer such as one implemented by input embedding module 411 of FIG. 4. Also shown in FIG. 5 is the output of encoder block 531 and its chain of transformers. In various embodiments, this output corresponds to intermediate or hidden representations for each position of the query protein. In some embodiments, the determined representations correspond to a set of output values or logits. Multi-track biological protein language model 503 projects the determined representations (or logits) for each track of multi-track output 505, unmasking any corresponding masked input values of masked multi-track input 501. In some embodiments, the output layer processing is performed by output processing module 419 of FIG. 4.

In some embodiments, structure input data 511 utilizes a coordinates format for describing biological structure such as protein structure. In the example of FIG. 5, the structure data of structure input data 511 can include the coordinates for each of the three backbone atoms of each of the L amino acids of a protein. The backbone atoms can correspond to nitrogen (N), alpha-carbon (CA), and carbon (C) atoms and each can be described by a set of three-dimensional spatial coordinates corresponding to X, Y, and Z coordinates. Structure input data 511 can include fewer than L amino acids when only a partial structure is defined. For a protein with L amino acids, the backbone coordinates have size $L \times 3 \times 3$. In some embodiments, backbone frames 521 utilizes a frame format by determining a backbone frame for each protein amino acid backbone. For example, a frame can include the coordinates of the alpha-carbon atom and a $3 \times 3$ rotation matrix for the frame defined by the nitrogen, alpha-carbon, and carbon atoms. In some embodiments, the alpha-carbon is placed at the origin and the nitrogen atom defines the X-axis. Although specific spatial and structure formats are described, alternative formats are appropriate as well. For example, another reference point other than the nitrogen atom of a backbone can be used to define the X-axis. Moreover, although FIG. 5 is shown with backbone frames 521, other frame formats other than ones based on a backbone frame are appropriate as well. In some embodiments, structure input data 511 and multi-track biological protein language model 503 are alternatively configured to utilize a structure format that relies on a different set of atoms (other than backbone atoms) such as a format that utilizes all atomic coordinates.

In various embodiments, the block diagram of FIG. 5 corresponds to only a partial view of a multi-track biological language model. For example, some of the components shown of multi-track biological protein language model 503 may be simplified and certain dimensions flattened for ease of demonstration. Additionally, certain components of FIG. 5 may be replicated to maximize performance such as by performing additional processing in parallel. In order to emphasize certain features of multi-track biological protein language model 503, some components may exist that are not shown, such as certain layers and functional components of the multi-track biological protein language model.

Figure 6:
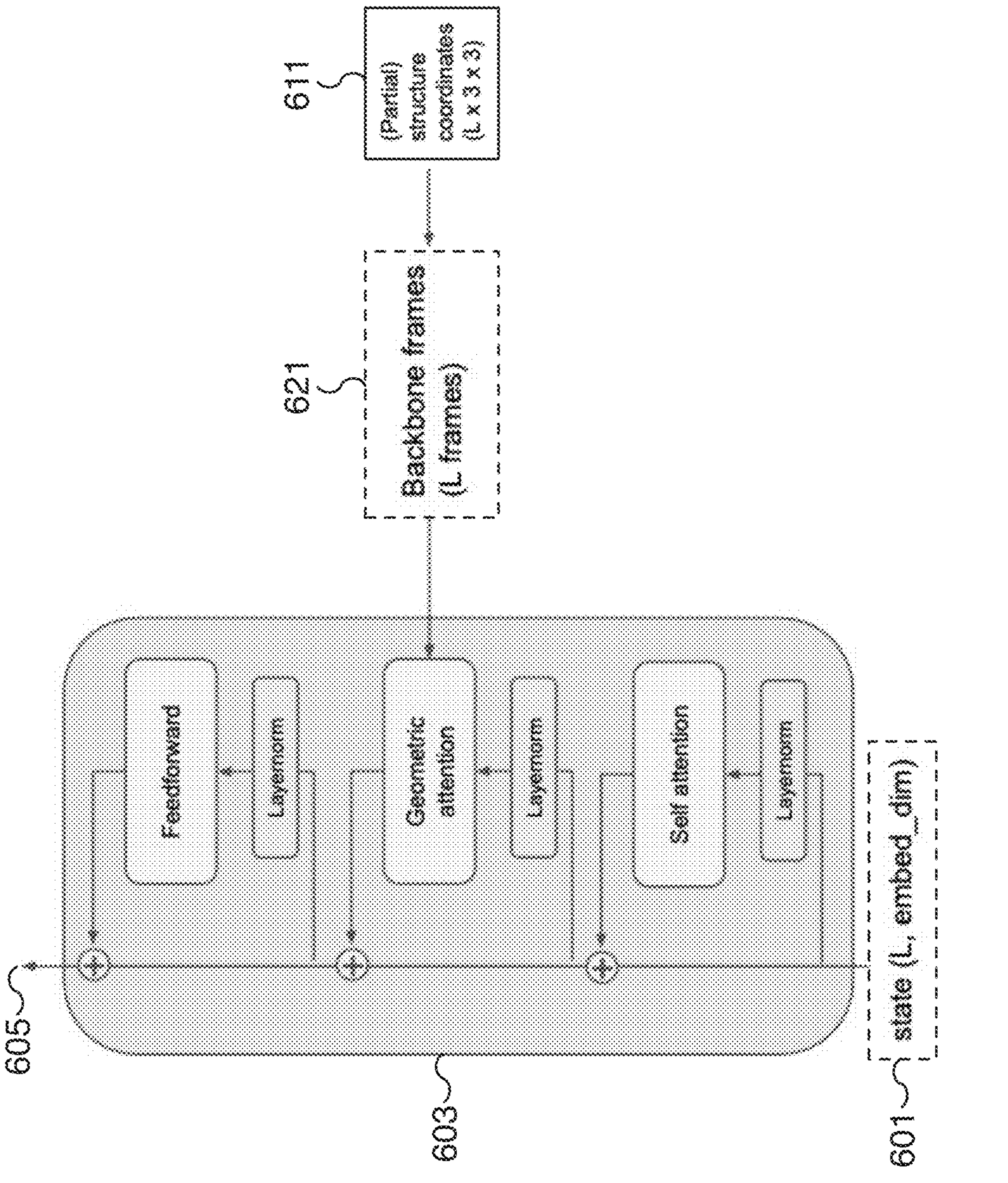
FIG. 6 is a block diagram illustrating an embodiment of a transformer block with a geometric attention mechanism of a multi-track biological language model.

FIG. 6 is a block diagram illustrating an embodiment of a transformer block with a geometric attention mechanism of a multi-track biological language model. In the example shown, state information 601 is provided by an upstream component of a multi-track biological language model to transformer block with a geometric attention 603. Transformer block with a geometric attention mechanism 603 includes multiple functional components including layer normalization, geometric attention, and feed forward blocks. In some embodiments, the multi-track biological language model is multi-track biological protein language model 503 of FIG. 5, transformer block with a geometric attention 603 is transformer block with geometric attention 541 of FIG. 5, structure input data 611 is structure input data 511 of FIG. 5, and/or backbone frames 621 is backbone frames 521 of FIG. 5.

As shown in FIG. 6, structure input data 611 corresponding to local amino acid structure data for the query protein is converted to backbone frames 621. Backbone frames 621 is received at the geometric attention block of transformer block with a geometric attention 603 for applying geometric attention based on the provided local structure described by structure input data 611. The arrangement of functional components including layer normalization, geometric attention, and feed forward blocks of transformer block with a geometric attention 603 determines an updated representation of the state 601 and is outputted as updated state 605. Updated state 605 can be provided to a downstream stage of the multi-track biological language model such as a downstream transformer block. In various embodiments, updated state 605 reflects the application of self-attention, geometric attention, and feed forward networks. As shown in FIG. 6, the provided local structure information can be limited to a partial description of the query protein. Although FIG. 6 is shown with backbone frames 621, other frame formats other than ones based on a backbone frame are appropriate as well. In some embodiments, structure input data 611 and transformer block with a geometric attention 603 are alternatively configured to utilize a structure format that relies on a different set of atoms (other than backbone atoms) such as a format that utilizes all atomic coordinates.

Figure 7:
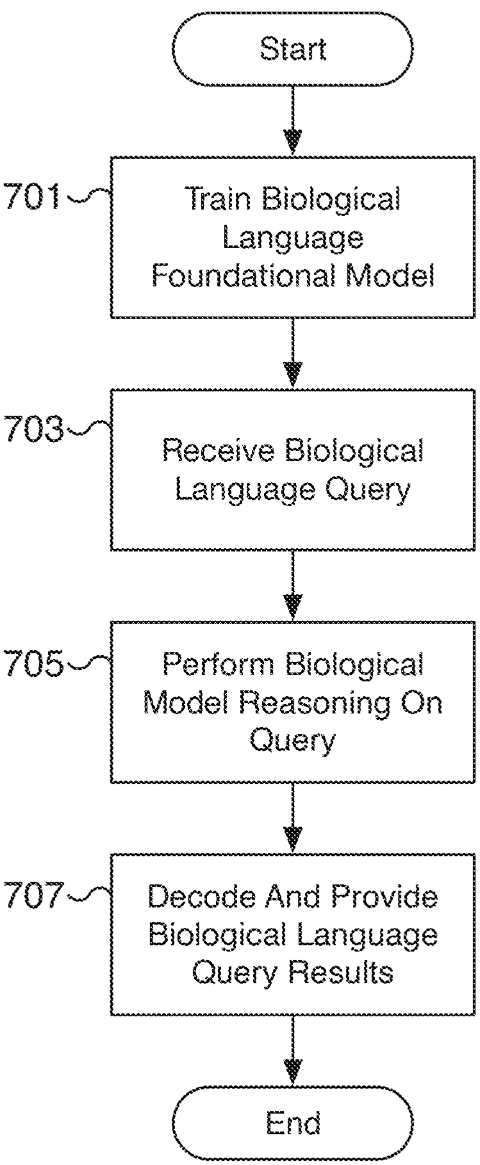
FIG. 7 is a flow chart illustrating an embodiment of a process for performing biological language reasoning using a biological language reasoning model.

FIG. 7 is a flow chart illustrating an embodiment of a process for performing biological language reasoning using a biological language reasoning model. For example, using the process of FIG. 7, a biological language query can be answered using a trained biological language reasoning model, such as a biological language reasoning model trained for generating and predicting proteins. In various embodiments, the model is a multi-track model that generates and predicts biological properties of a target object, such as a query protein. When applied to proteins, the model can predict both sequence and structure. Additional protein properties can include secondary structure, tertiary structure, quaternary structure, and/or functions at an atomic and/or amino acid level. In various embodiments, the disclosed biological language reasoning model is a multi-track model that allows the model to respond to queries along one or more different tracks. For example, a biological protein language reasoning model can be queried to predict and/or generate a protein's amino acid sequence, structure, secondary structure, protein solvent accessible surface area, and function. In some embodiments, the process of FIG. 7 is performed by a biological language model service such as biological language model service 111 of FIG. 1 and/or biological language model service 201 of FIG. 2. In some embodiments, the biological language model is biological language model 303 of FIG. 3.

At 701, a biological language foundational model is trained. For example, a biological language foundation model can be trained on billions or more parameters and with training data containing multiple tracks. For particular biological domains, such as for protein generation and prediction, the amount of experimental data may be limited. To address this limitation, a biological language foundation model can be trained on both experimental and synthetic data. For example, data sources can be scored based on their origin, accuracy, and/or quality when training and corresponding quality metrics can be specified during inference. In various embodiments, the trained biological language foundation model is a multi-track transformer encoder model and utilizes transformers that are not restricted in a specific or single direction when considering biological context, such as for a protein sequence or structure. For example, a biological protein language reasoning model is trained to predict protein sequence, structure, and/or function, among other protein properties even when provided with partial or masked query protein data. Additional tracks for a protein language model include secondary structure, tertiary structure, quaternary structure, function, and solvent accessible surface area tracks.

In some embodiments, the biological language foundational model is further trained on biological interactions including molecular interactions within a biological object and/or between two or more biological objects such as multiple proteins. For example, multimer data such as data based on proteins binding together is used to train the model to predict molecular binding between two or more proteins. In various embodiments, the protein binding data included in the training data is sourced from peptides, protein-protein binders, antibodies, and/or nanobodies, among other sources. Furthermore, data for interactions within a biological object such as long-range tertiary contacts for single proteins can also be used for training molecular interaction predictions. In some embodiments, one or more specialized tokens such as chain break and/or epitope tokens are used for describing multiple objects and/or molecular interaction locations. Moreover, the training for biological interactions can be performed as a pretraining and/or finetuning step. For example, the biological language foundational model can be finetuned using techniques such as supervised finetuning and direct preference optimization (DPO) techniques to emphasize and align the prediction results to binding tasks.

In various embodiments, the biological language foundation model is trained using a range of mask rates. By training on variable mask rates and without a specific masking objective, the trained biological language foundation model can predict multiple tokens for each forward pass. For example, a trained biological protein language foundation model can predict a complete protein structure (and sequence) when queried with a partial protein sequence. Similarly, a trained biological protein language foundation model can predict a complete protein sequence when provided with a partial protein structure. In various embodiments, the model is trained for promptability characteristics that allow the model to predict across and within different tracks such as to predict a sequence from function, function from sequence, structure from function, structure from partial structure, etc.

In some embodiments, the training of the biological language foundation model includes training one or more tokenizers. For example, each track of the multi-track biological language foundation model can utilize a tokenizer, such as a protein sequence tokenizer, protein structure tokenizer, and a protein function tokenizer, etc. In various embodiments, one or more of the tokenizers are trained to encode, decode, and understand specialized tokens such as chain break and epitope tokens. For example, a chain break token can be inserted between two biological objects such as between two proteins. As an input token, the chain break token signals to the biological language reasoning model that multiple objects are described in the input, such as a binding target protein followed by a masked binder protein. Based on the provided input, the biological language reasoning model predicts the structural binding result of the two biological objects including by generating the identities for masked positions of the binder protein. In some embodiments, a chain break token as an output token in the prediction output results indicates where one object ends and another starts. For example, a chain break token in the output prediction results can be used to indicate the end of a binding target protein sequence and the start of a binder protein sequence. As another example, a tokenizer can be trained to learn epitope tokens that are used to indicate an epitope of a binding target protein. For example, epitope tokens can be inserted in the binding target protein sequence at the start and end of an epitope location. In some embodiments, a different start epitope token and end epitope token is used. In various embodiments, epitope tokens are used to train the biological language reasoning model to understand the positions/locations of a binding target protein to which a generated binder protein should bind. In some embodiments, an epitope token is a property and/or subset of a function token. In some embodiments, alternatives to an epitope token are used, such as a binder track for the model or a conditioning epitope tensor. In various embodiments, in the context of proteins, a protein structure tokenizer is trained to encode local structure including local amino acid structure for proteins. For improved performance and resource utilization, a biological language foundation model can then be trained on pre-tokenized data such as pre-tokenized structure data. The use of pre-tokenized data for training results in significant performance and resource utilization advantages.

In some embodiments, the training step performed at 701 includes additional optional training steps such as fine-tuning, post-training, and/or model alignment. For example, one or more additional post-training steps can be performed to improve the model's performance, robustness, interoperability, safety, and/or accuracy, among other desired goals, as well as to customize and/or adapt the model for specific tasks. In some embodiments, the additional training is performed on a new dataset, for example, that is prepared for a specific targeted task.

At 703, a biological language query is received. For example, a biological reasoning query is received for the biological language foundation model trained at 701. The query can be a search query for a specific biological object such as a target protein that meets the provided constraints. In some embodiments, the query can be for a combination of biological objects such as for a masked binder protein that binds to an unmasked binding target protein. For example, constraints can be provided based on unmasked values for the different tracks of the multi-track biological language foundation model trained at 701. In some embodiments, the query is processed and used to perform multiple inference passes of the biological language foundation model. For example, multiple inference passes can be performed to iteratively narrow and refine the search query results.

In various embodiments, the biological language query received at 703 can be provided in one or more supported formats. For example, the query can be a biological language foundation model prompt with input tokens. As another example, the query can utilize a biological language programming language. The biological language programming language can define the context of the query object such as a query protein and constraints and/or target goals for the query. In some embodiments, the query is generated and/or provided at least in part via a visual interface, such as one that allows a user to specify protein sequence, structure, function, etc. using a graphical user interface tool. Other protein properties the query can search can include solvent accessible surface area and secondary structure of a query protein.

In some embodiments, the received query can further specify an accuracy required for the corresponding query result. For example, the search query can specify confidence values for prediction results including specifying the type of training data the prediction result should rely on. In some embodiments, the query can be conditioned on properties of training data such as whether the training data is based on experimental and/or synthetic training data.

At 705, biological model reasoning is performed on the received biological language query. For example, the biological language search query received at 703 is solved using the biological language foundation model trained at 701. In some embodiments, one or more inference passes of the biological language foundation model are performed to refine the search query results. In some embodiments, the biological language model is used to unmask the masked parameters for each track of the multi-track biological language foundation model. For example, sequence, structure, and function, among other tracks are unmasked to generate and predict a biological result such as a target protein. In various embodiments, the biological model reasoning is performed by applying multiple transformer encoder layers including multiple attention mechanisms of the biological language foundation model. The attention mechanisms can include self-attention and/or geometric attention mechanisms based on the biological language learned during the training phase performed at 701. In some embodiments, additional post-processing such as fine-tuning is performed to refine the prediction results of the biological language foundation model.

At 707, the biological language query results are decoded and provided. For example, the inference results from the biological language foundation model are processed to determine search query results. In some embodiments, the inference results determined at 705 are tokenized output and the tokenized output is decoded at 707. For example, a predicted set of protein sequence tokens including protein sequence tokens for one, two, or more proteins can be decoded into one or more user-accessible protein amino acid sequences including protein sequences that can be used for protein synthesis. In some embodiments, the predicted set of protein sequence tokens includes a predicted binder protein bound to a binding target protein. The binder protein and binding target protein may be separated by a chain break token. As another example, a predicted set of protein structure tokens can be decoded into a user-accessible protein structure that can be visualized. In various embodiments, the biological language query results are provided in a requested format. For example, the results can be provided according to a programming language format that allows for the use of a biological programming language to process the search query results programmatically. As another example, the results can be presented in a visual and/or multi-media format. For example, the results can be provided to a client via a graphical user interface including virtual and/or augmented user interfaces. In some embodiments, the results are provided and allow for a user (or program) to review, iterate on, refine, and/or modify the biological language query results and corresponding search.

Figure 8:
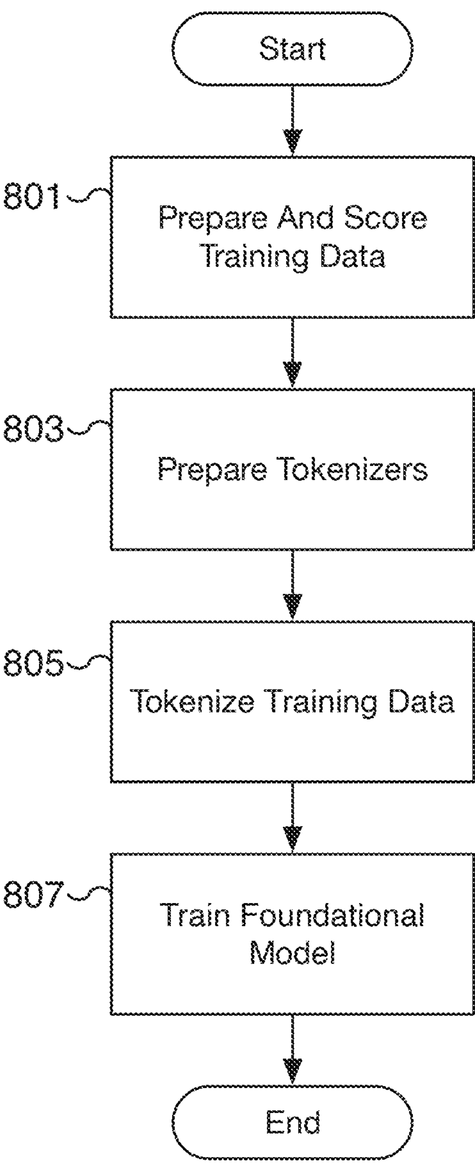
FIG. 8 is a flow chart illustrating an embodiment of a process for training a biological language reasoning model.

FIG. 8 is a flow chart illustrating an embodiment of a process for training a biological language reasoning model. For example, using the process of FIG. 8, a biological language reasoning model can be trained to perform biological language reasoning. In various embodiments, the biological language foundation model is trained as a multi-track transformer encoder model and utilizes transformers that are not restricted in a specific or single direction when considering biological context, such as for a protein sequence or structure. For example, a biological protein language reasoning model is trained to predict protein sequence, structure, and/or function, among other protein properties even when provided with partial or masked query protein data. Additional tracks for a protein language model include secondary structure, tertiary structure, quaternary structure, function, and solvent accessible surface area tracks. In some embodiments, the process of FIG. 8 is performed at 701 of FIG. 7 by a biological language model training module such as biological language model training module 213 of FIG. 2 of a biological language model service such as biological language model service 111 of FIG. 1 and/or biological language model service 201 of FIG. 2. In some embodiments, the biological language model trained using the process of FIG. 8 corresponds to the model associated with biological language model 303 of FIG. 3, biological language model module 401 of FIG. 4, and/or multi-track biological protein language model 503 of FIG. 5.

At 801, training data is prepared and scored. For example, training data for the target biological domain of the biological language reasoning model is prepared. For particular biological domains, such as for protein generation and prediction, the amount of experimental data may be limited. To address this limitation, a biological language foundation model can be trained on both experimental and synthetic data. For example, data sources can be scored based on their origin, accuracy, and/or quality when training and corresponding quality metrics can be specified during inference. Similarly, the training data can be scored with confidence values corresponding to the accuracy of the data. In various embodiments, the training data addresses all the tracks of the multi-track model. For example, for a multi-track protein language model that predicts sequence, structure, and function, training data can be prepared for each track using both experimental and/or synthetic data. For certain tracks, more experimental data may be available and for other tracks, a mixture of experimental and synthetic data may be utilized. In some embodiments, the training data is additionally masked for masked token prediction.

At 803, tokenizers for the biological language reasoning model are prepared. For example, for each track of the multi-track biological language reasoning model, a tokenizer can be prepared. In some embodiments, the tokenizer for a track is an autoencoder and/or utilizes an encoder-decoder architecture. For example, a protein structure tokenizer is prepared by training a protein structure encoder and decoder for tokenizing protein structure and decoding predicted structure tokens. Similarly, a function tokenizer can be trained based on an identified function vocabulary. In various embodiments, the tokenizers can be trained at the atomic level of the biological domain. For example, for protein generation and prediction, the tokenizers can be trained to encode tokens for each amino acid location of a query protein. In various embodiments, the training process for various tokenizers utilizes one or more loss functions. For example, a structure tokenizer can utilize one or more geometric loss functions to encode a semantic understanding of geometric structure. In some embodiments, tokenization is performed in real-time or near real-time rather than requiring a process that first creates a vocabulary. For example, by tokenizing in real or near real-time, the tokenizers can create new tokens as raw training data is sent to the model for training.

At 805, training data for the biological language reasoning model is tokenized. For example, the training data can be pre-tokenized prior to training. By tokenizing the training data and feeding pre-tokenized input to the biological language reasoning foundational model, aspects of the foundational model can be streamlined. Similarly, the tokenization of complex model input data, such as three-dimensional protein atomic structure data, prior to training significantly improves performance when training the biological language reasoning foundational model. For example, the resources and time required for training the biological language reasoning foundational model are significantly reduced when the model is at least partially trained with tokenized input rather than requiring the model to perform all tokenizing tasks at training. In various embodiments, the training data can be stored in a tokenized format for future and additional rounds of training.

At 807, a biological language reasoning foundational model is trained. For example, using the training data prepared at 801 and tokenized at 805, the biological language reasoning foundational model is trained. In some embodiments, the training is performed using different mask rates allowing the biological language reasoning foundational model to unmask biological features without direction restrictions and/or to predict multiple tokens for each forward pass. For example, the trained biological language foundation model can utilize transformers that are not restricted in a specific or single direction when considering biological context, such as for a protein sequence or structure. In various embodiments, the training process is an iterative process and the performance of the model is monitored using testing and validation data sets generated from the training data prepared at 801. In some embodiments, the training process utilizes one or more loss functions, such as loss functions based on token prediction losses.

Figure 9:
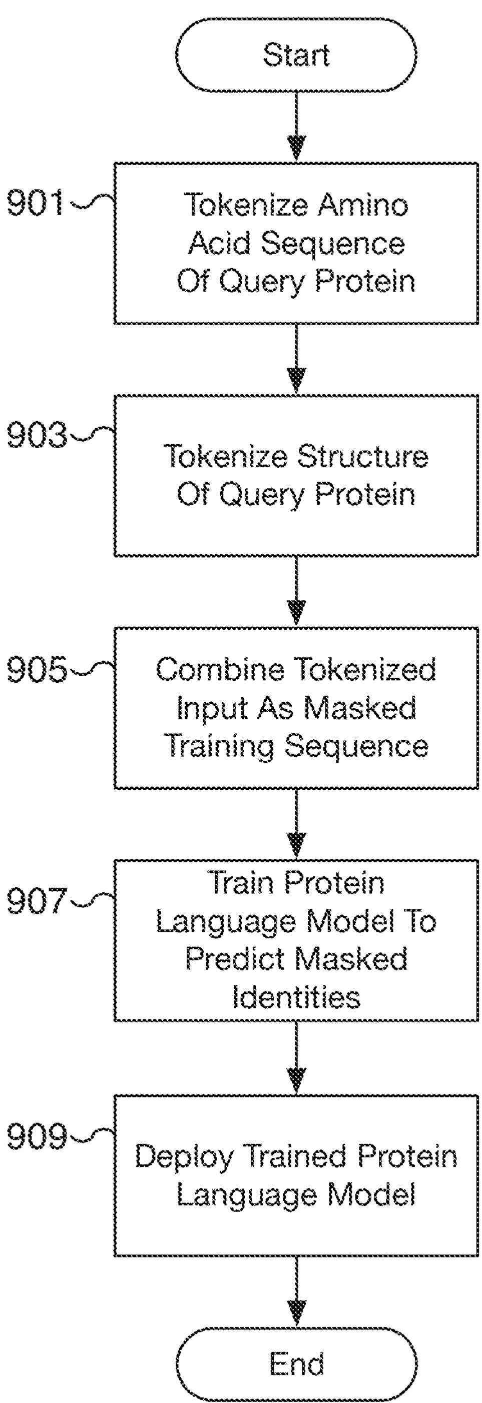
FIG. 9 is a flow chart illustrating an embodiment of a process for training a biological protein language model.

FIG. 9 is a flow chart illustrating an embodiment of a process for training a biological protein language model. For example, using the process of FIG. 9, a biological protein language model can be trained to perform biological protein language reasoning. In some embodiments, the protein language model is trained as a multi-track transformer encoder model and utilizes transformers that are not restricted in a specific or single direction when considering protein context, such as amino acid location for protein sequence, structure, or function. For example, the trained biological protein language model can predict at least a complete protein sequence and structure when provided with partial or masked input. As another example, the trained biological protein language model can predict a binder protein sequence and corresponding binder protein structure when provided with partial or full binding target protein and a masked binder protein as input. Additionally, the trained model can be extended to other protein properties such as function and secondary structure, among others. In some embodiments, the process of FIG. 9 is performed at 701 of FIG. 7 and/or at 805 and/or 807 of FIG. 8 by a biological language model training module such as biological language model training module 213 of FIG. 2 of a biological language model service such as biological language model service 111 of FIG. 1 and/or biological language model service 201 of FIG. 2. In some embodiments, the biological protein language model trained using the process of FIG. 9 corresponds to the model associated with biological language model 303 of FIG. 3, biological language model module 401 of FIG. 4, and/or multi-track biological protein language model 503 of FIG. 5.

At 901, the amino acid sequence of a query protein is tokenized. For example, each amino acid in a sequence of a query protein is converted to an input token. In various embodiments, the protein sequence tokenizer is trained based on the set of available amino acids to encode each amino acid of the protein sequence. Other approaches are appropriate as well. For example, the protein sequence tokenizer may also utilize a dictionary lookup to tokenize the amino acid sequence by mapping each amino acid in the amino acid sequence to an amino acid token. In some embodiments, each amino acid is associated with a unique identifier and the applied tokenizer can utilize a transformer model configured with attention mechanisms to tokenize the provided amino acid identifier. In some embodiments, the tokenization is performed in real-time or near real-time rather than requiring a process that first creates a vocabulary. For example, by tokenizing in real or near real-time, the tokenizers can adapt to new tokens as they appear.

At 903, the structure of the query protein is tokenized. For example, the structure of a query protein is received including a description of local amino acids. In some embodiments, the local amino acids of the protein are described by their spatial positioning including by three-dimensional coordinates of their backbone atoms. In various embodiments, the local structure is encoded using a trained protein structure tokenizer that applies geometric attention to embed local context into structure tokens. For example, each amino acid is tokenized in the context of its nearest neighboring amino acids. In some embodiments, the protein structure tokenizer is trained to encode the context of each amino acid of a protein with respect to the distance and direction of each amino acid to its determined nearest neighboring amino acids by physical distance. In some embodiments, the trained protein structure tokenizer is an autoencoder. The encoder can be applied to generate structure tokens and the corresponding decoder can be applied to decode protein structure tokens into a protein structure. In some embodiments, the structure tokens are discrete tokens created by quantizing an encoder output using a learned codebook.

At 905, the tokenized input is combined as a masked training sequence. For example, the tokens created for sequence and structure at 901 and 903, respectively, are combined as a training sequence. In various embodiments, the training sequence is masked at specific mask rates to allow the protein language model to learn a contextual understanding of protein sequence and structure. In various embodiments, the protein language model is a multi-track transformer model and the input tokens are combined according to sequence and structure tracks.

At 907, a protein language model is trained to predict masked identities. For example, using the training data created at 905 from masked training sequences, the protein language model is trained to predict masked identities. With a sufficient amount of masked training sequence data, including sequences masked at different mask rates, the model can learn a contextual understanding of protein sequence and structure. In various embodiments, the training process is an iterative process and the performance of the model is monitored using testing and validation data sets. In some embodiments, the training process utilizes one or more loss functions including geometric loss functions to encode a semantic understanding of geometric structure into the trained biological language reasoning foundational model.

At 909, the trained protein language model is deployed. For example, the trained weights of the model are deployed for use with a biological language model service. In some embodiments, the model is accessible via a biological language reasoning service that accepts search queries and provides model responses to the received queries. In some embodiments, additional training may be performed including fine-tuning steps, such as for specific search queries or query types, and/or a post processing pipeline may be configured. For example, a post-processing pipeline can be configured that is performed to convert model output to a format usable by client users.

Figure 10:
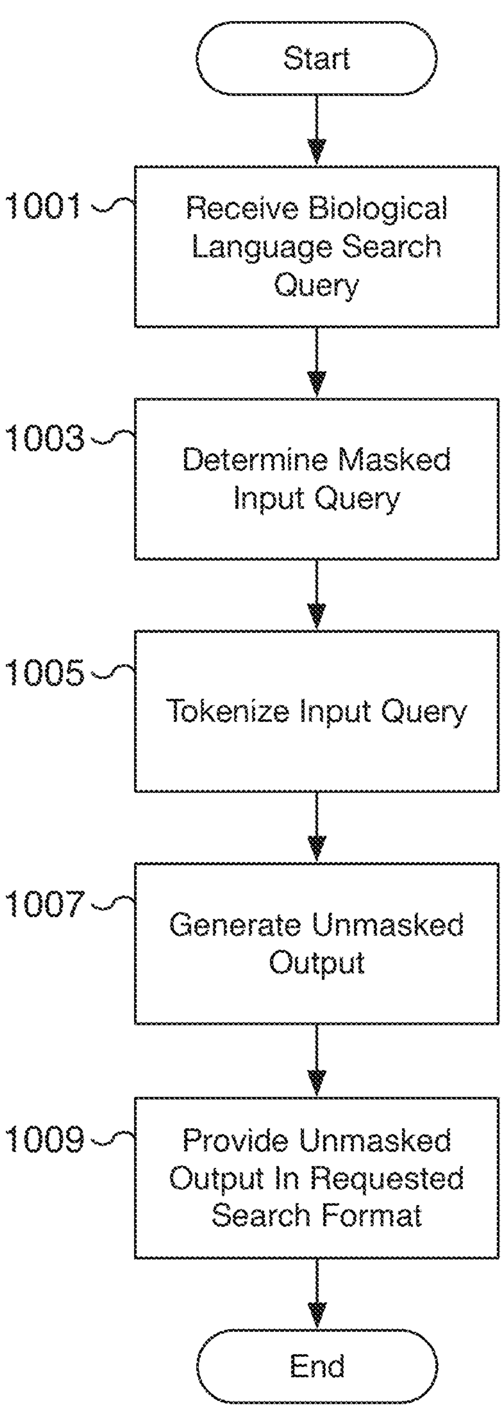
FIG. 10 is a flow chart illustrating an embodiment of a process for applying a biological language reasoning model to a biological language search query.

FIG. 10 is a flow chart illustrating an embodiment of a process for applying a biological language reasoning model to a biological language search query. For example, using the process of FIG. 10, a biological language search query is received, and a result is determined using a biological language reasoning model. In various embodiments, the search query is processed and corresponding input tokens for the model are created with selective portions of the input masked. In response to the masked input, the model can predict the identities of the masked portions. In some embodiments, the process of FIG. 10 is performed at 703, 705, and/or 707 of FIG. 7 by a biological language model service such as biological language model service 111 of FIG. 1 and/or biological language model service 201 of FIG. 2. In some embodiments, the search query can be processed and evaluated using a combination of the functional modules including search query module 215 of FIG. 2, prompt generation module 217 of FIG. 2, prompt evaluation module 219 of FIG. 2, and/or trained biological language model module 223 of FIG. 2. In some embodiments, the biological language reasoning model used for inference results corresponds to biological language model 303 of FIG. 3, biological language model module 401 of FIG. 4, and/or multi-track biological protein language model 503 of FIG. 5.

At 1001, a biological language query is received. For example, a user provides a biological language query with the expectation of a query result. In some embodiments, the query is provided using a programming language format such as using a biological language programming language that allows the query and results to be processed programmatically. In some embodiments, the biological language query corresponds to a generative artificial intelligence (AI) prompt that can be processed by the model. In some embodiments, the biological language query is received via an application programming interface (API). Other formats and interfaces for the biological language query can be appropriate as well including visual and/or graphical interfaces. For example, a biological language query can be constructed using a graphical user interface including by specifying structure constraints. In various embodiments, the search query can be processed to convert the query into a native format understood by the biological language model. For example, a search query constructed using a biological language programming language format can be compiled and/or parsed and converted into a native format understood by the biological language model.

At 1003, a masked input query is determined. For example, based on the biological language query received at 1001, the query is processed to determine a masked input query for the biological language reasoning model. In various embodiments, different tracks corresponding to different properties of the biological object are evaluated to determine which portions are masked and which are unmasked. For example, the provided constraints can be a partial description such as a partial physical structure with corresponding masked and unmasked identities. In some embodiments, the query is processed and a corresponding generative artificial intelligence (AI) prompt is created along with the masked input query.

At 1005, the input query is tokenized. For example, the masked input query determined at 1003 is tokenized to create input tokens for each track of the biological language reasoning model. In some embodiments, each track can utilize a different trained tokenizer such as a trained auto-encoder. For example, a trained structure tokenizer can tokenize a structure track of the masked input query while applying geometric attention. In various embodiments, the input tokens can embed a learned context of the input query object and can include learned local context information. In some embodiments, the input query includes and/or references multiple biological objects such as a sequence of two or more proteins. During the tokenization performed at 1005, the individual biological objects can be delineated. For example, the tokenized representations of two proteins can be separated by a break token to delineate when one protein ends and another starts.

At 1007, an unmasked output is generated. For example, the biological language reasoning model is evaluated with the input tokens to determine an output result. The output result predicts and unmasks the masked identities of the masked input query determined at 1003. In some embodiments, the input tokens are evaluated by the biological language reasoning model based on a provided generative artificial intelligence (AI) prompt. For example, a provided generative AI prompt provides direction and context for evaluating the input tokens created at 1005. The biological language reasoning model can utilize multiple transformer encoder layers including multiple attention mechanisms of the biological language reasoning model when generating values including unmasked values for the query result. In various embodiments, the output including the unmasked output is provided in a tokenized format. For example, the predicted structure can be a set of structure tokens with predicted values for any previously masked values as defined by the search query.

At 1009, the unmasked output is provided in the requested search format. For example, the unmasked output results generated at 1007 using the biological language reasoning model are processed to provide search query results in a requested format. In some embodiments, the unmasked output is tokenized by the biological language reasoning model and a decoding step is performed to decode tokens into more accessible formats. For example, a predicted set of structure tokens can be decoded into a user-accessible structure that can be visualized. In some embodiments, the search format utilizes a format such as a biological language programming language and the unmasked output results generated at 1007 are converted into a programming language result. Other formats may be applicable as well. For example, the unmasked output can be packaged as an application programming interface (API) result to conform with a pre-defined API interface.

Figure 11:
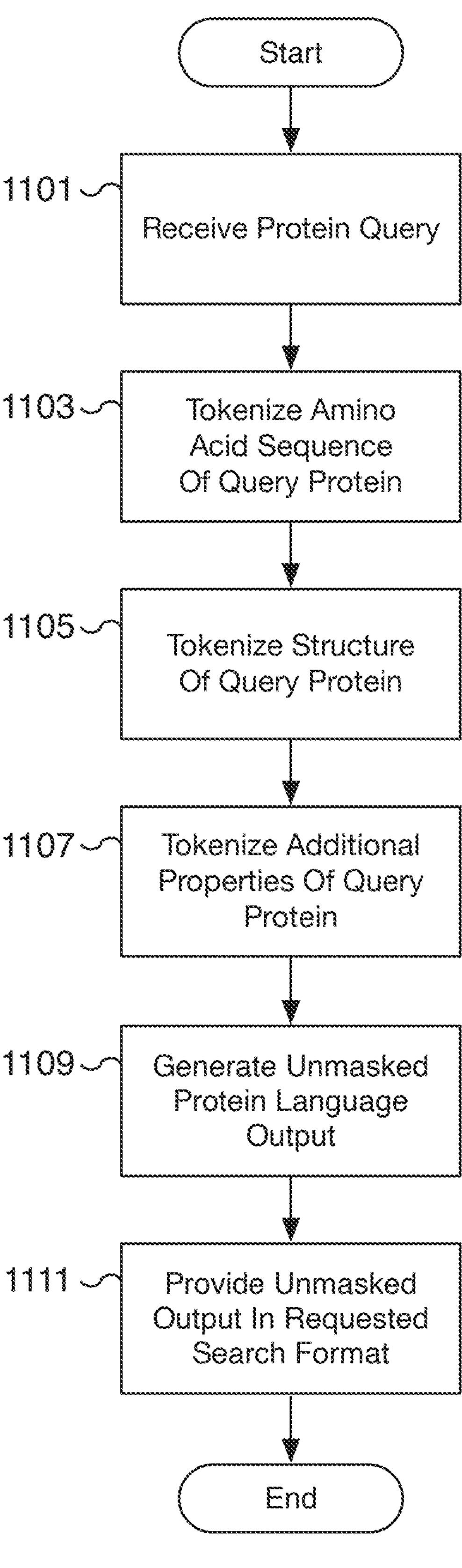
FIG. 11 is a flow chart illustrating an embodiment of a process for applying a biological protein language model to a biological protein language search query.

FIG. 11 is a flow chart illustrating an embodiment of a process for applying a biological protein language model to a biological protein language search query. For example, using the process of FIG. 11, a biological language reasoning model trained to understand and reason using a protein language on query proteins is applied to answer biological protein language search queries. In various embodiments, the biological language reasoning model is a multi-track biological protein language model with tracks at least for protein sequence and structure. Although described in FIG. 11 with protein sequence and structure tracks, additional tracks, such as secondary structure, function, and other protein property tracks can be supported as described herein. In various embodiments, a protein search query is processed and corresponding protein input tokens are created with selective portions of the input masked. In response to the masked input, the biological protein language model can predict the identities of the masked portions such as masked portions of the query protein's sequence and/or structure. In some embodiments, the process of FIG. 11 is performed at 703, 705, and/or 707 of FIG. 7 and/or using the process of FIG. 10 by a biological protein language model service such as biological language model service 111 of FIG. 1 and/or biological language model service 201 of FIG. 2. In some embodiments, the protein search query can be processed and evaluated using a combination of the functional modules including search query module 215 of FIG. 2, prompt generation module 217 of FIG. 2, prompt evaluation module 219 of FIG. 2, and/or trained biological language model module 223 of FIG. 2. In some embodiments, the biological protein language model used for inference results corresponds to biological language model 303 of FIG. 3, biological language model module 401 of FIG. 4, and/or multi-track biological protein language model 503 of FIG. 5.

At 1101, a biological protein language query is received. For example, a user provides a biological protein language query with the expectation of a protein query result. The biological protein language query can describe a specific query protein to predict a suitable protein (or proteins) that matches the constraints expressed by the biological protein language query. The biological protein language query may also describe a sequence of proteins, such as a combination of two or more proteins. For example, a query can include a binder protein and a binding target protein where the predicted binder protein should bind to the binding target protein. The biological protein language query may be constructed to predict one or more of the included proteins by unmasking any unknown properties including how the proteins of the query will fold and be held together. In some embodiments, the result of the biological protein language query is a set of proteins that resolve and/or satisfy the biological protein language query. In some embodiments, the biological protein language query is provided using a programming language format such as using a biological language programming language that allows the biological protein language query and results to be processed programmatically. In some embodiments, the biological protein language query corresponds to a generative artificial intelligence (AI) prompt that can be processed by the biological protein language model. In some embodiments, the biological protein language query is received via an application programming interface (API). Other formats and interfaces for the biological protein language query can be appropriate as well including visual and/or graphical interfaces. In various embodiments, the biological protein language query can be processed to convert the biological protein language query into a native format understood by the biological protein language model. For example, a biological protein language query constructed using biological language programming language format can be compiled and/or parsed and converted into a native format understood by the biological protein language model.

At 1103, the amino acid sequence of the biological protein language query protein is tokenized. For example, each amino acid in a sequence of the query protein is converted to an input token. In various embodiments, the protein sequence tokenizer is trained based on the set of available amino acids to encode each amino acid of the protein sequence. Other approaches are appropriate as well. For example, the protein sequence tokenizer may also utilize a dictionary lookup to tokenize the amino acid sequence by mapping each amino acid in the amino acid sequence to an amino acid token. In some embodiments, each amino acid is associated with a unique identifier and the applied tokenizer can utilize a transformer model configured with attention mechanisms to tokenize the provided amino acid identifier.

At 1105, the structure of the biological protein language query protein is tokenized. For example, the structure of the query protein is received including a description of local amino acids. In some embodiments, the local amino acids of the query protein are described by their spatial positioning including by three-dimensional coordinates of their backbone atoms. In various embodiments, the local structure is encoded using a trained protein structure tokenizer that applies geometric attention to embed local context into structure tokens. For example, each amino acid is tokenized in the context of its nearest neighboring amino acids. In some embodiments, the protein structure tokenizer is trained to encode the context of each amino acid of a protein with respect to the distance and direction of each amino acid to its determined nearest neighboring amino acids by physical distance. In some embodiments, the trained protein structure tokenizer is an autoencoder. The encoder can be applied to generate structure tokens and the corresponding decoder can be applied to decode protein structure tokens into a protein structure. In some embodiments, the structure tokens are discrete tokens created by quantizing an encoder output using a learned codebook.

At 1107, additional properties of the biological protein language query protein are tokenized. For example, input for additional tracks supported by the biological protein language model such as secondary structure, tertiary structure, quaternary structure, function, and solvent accessible surface area tracks are tokenized using the appropriate trained track tokenizer. In some embodiments, non-tokenized input may be received and processed by the model. For example, the biological protein language model can receive non-tokenized input, such as protein structure data, in addition to or as an alternative to tokenized input. In various embodiments, for non-tokenized input such as non-tokenized protein structure input, the biological protein language model can implement attention mechanisms such as geometric attention mechanisms to encode local geometric understanding.

In some embodiments, a function track supported by the biological protein language model allows each position of a biological object to be associated with and/or described by zero, one, or more functions. For example, for a protein object, an initial vocabulary of function labels is determined. The function labels can be sourced from one or more known public databases and/or one or more private data sources, among other sources. When applied to protein function, each position of a protein can be associated with any number of the known functions. For example, for a protein with sequence length L and a function vocabulary size K, there are L×K applicable labels. For a determined function vocabulary, vocabulary size K can exceed 30,000 entries corresponding to 30,000 or more different function annotation tags. In various embodiments, due to the large number of function annotation tags applicable for each protein sequence position, the function label input is compressed as part of tokenization. For example, at each sequence position, the function labels at that position can be converted into a single Term Frequency-Inverse Document Frequency (TF-IDF) vector. In various embodiments, each converted TF-IDF vector represents the saliency of text keywords that describe the applicable functions in plain text descriptions. In some embodiments, a TF-IDF vector is constructed using associated text function descriptions from relied upon data sources. Example descriptions include InterPro and Gene Ontology text descriptions. In some embodiments, the TF-IDF vectors are compressed and tokenized by converting the vectors into discrete integer tokens for input to the biological protein language model. For example, a set of locality sensitive hashes (LSHs) can be applied to each TF-IDF vector. In various embodiments, each LSH produces a single token within a set range, such as between 0 and 255. Multiple integer tokens can be generated for each protein position by using multiple LSHs. For example, when a fixed set of eight LSHs are applied, eight integer tokens can be generated at each position to represent the semantic information from the function text descriptions. In various embodiments, each LSH is computed using a fixed number of hyperplanes sampled from a normal distribution. The LSH is applied by determining which side of each hyperplane the TF-IDF vector falls via the sign of the inner product of the TF-IDF vector with the hyperplane's normal vector. When using eight hyperplanes, a list of eight hyperplane-side binary values can be converted into an integer format such as an integer between 0 and 255.

At 1109, an unmasked protein language output is generated. For example, the biological protein language reasoning model is evaluated with the input tokens determined at 1103, 1105, and 1107 to predict an output result. In various embodiments, the tokenized input may be combined into a multi-track input for the biological protein language model. The corresponding output of the biological protein language model may be a multi-track output that unmasks the masked identities associated with the tokenized query protein. In some embodiments, the input tokens are evaluated by the biological protein language reasoning model based on a provided generative artificial intelligence (AI) prompt. For example, a provided generative AI prompt provides direction and context for evaluating the input tokens created at 1103, 1105, and 1107. The biological protein language reasoning model can utilize multiple transformer encoder layers including multiple attention mechanisms of the biological protein language model when generating values including unmasked values for the protein query result. In various embodiments, the output including the unmasked output is provided in a tokenized format. For example, the predicted protein structure can be a set of protein amino acid structure tokens with predicted values for any previously masked values as defined by the search query.

At 1111, the unmasked output is provided in the requested search format. For example, the unmasked output results generated at 1109 using the biological protein language reasoning model are processed to provide search protein query results in a requested format. In some embodiments, the unmasked output is tokenized by the biological protein language reasoning model and a decoding step is performed to decode tokens into more accessible formats. For example, a predicted set of protein structure tokens can be decoded into a user-accessible structure that can be visualized. As another example, a predicted set of protein sequence tokens can be decoded into a protein sequence format that allows the predicted protein to be experimentally synthesized. In some embodiments, the protein query search format utilizes a format such as a biological language programming language and the unmasked output results generated at 1109 are converted into a programming language result. Other formats may be applicable as well. For example, the unmasked output can be packaged as an application programming interface (API) result to conform with a pre-defined API interface.

Figure 12:
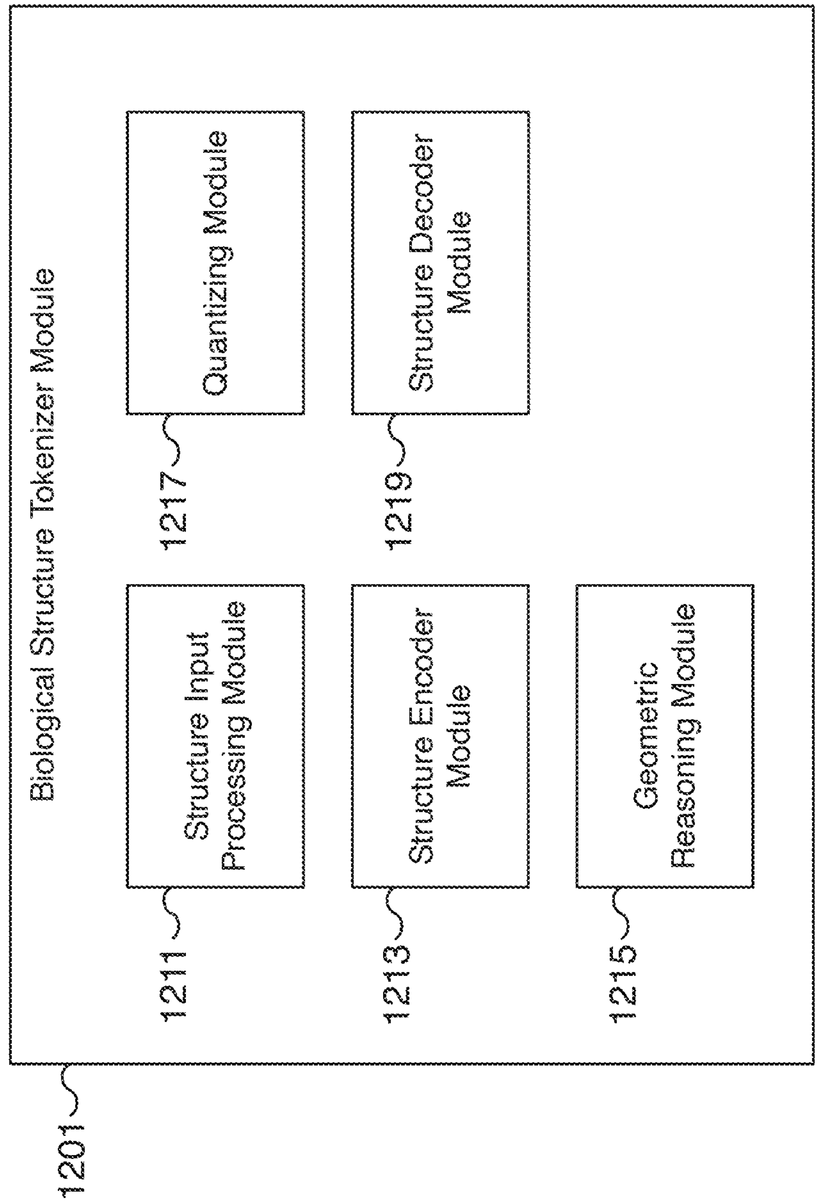
FIG. 12 is a block diagram illustrating an embodiment of a tokenizer for biological structure.

FIG. 12 is a block diagram illustrating an embodiment of a tokenizer for biological structure. For example, biological structure tokenizer module 1201 is trained to tokenize biological structure data for a specific biological domain such as for protein structure. Biological structure tokenizer module 1201 can be trained to tokenize structure data at the atomic level or at a coarser configured granularity depending on the application. Biological structure tokenizer module 1201 includes structure input processing module 1211, structure encoder module 1213, geometric reasoning module 1215, quantizing module 1217, and structure decoder module 1219. In some embodiments, biological structure tokenizer module 1201 is used to tokenize biological structure for training a biological language reasoning model, as a pre-processing step for performing inference using a biological language reasoning model, and/or for decoding structure token results generated by a trained biological language reasoning model. In some embodiments, biological structure tokenizer module 1201 is trained using tokenizer training module 211 of FIG. 2 and can utilize one or more configured geometric loss functions in the process of training. In some embodiments, biological structure tokenizer module 1201 corresponds to trained tokenizers module 221 of FIG. 2 of biological language model service 201 of FIG. 2. In some embodiments, biological structure tokenizer module 1201 is utilized by a biological language model service such as biological language model service 111 of FIG. 1 and/or biological language model service 201 of FIG. 2 as part of a process for performing biological language reasoning.

In some embodiments, structure input processing module 1211 is a processing module for processing provided structure data. For example, structure information can be provided in a non-tokenized format, such as a user-accessible format that allows users to interface with and in a biological language more easily. For example, for a biological protein language model, the local structure of amino acids can be provided in a standardized and/or documented structure format. In some embodiments, the received structure input utilizes backbone frames for each amino acid including specifying relevant atoms of an amino acid based on their three-dimensional spatial coordinates. In some embodiments, the received structure input includes all atomic coordinates for the relevant biological object, such as atoms of a protein. In various embodiments, structure input processing module 1211 receives the provided structure input and performs any necessary pre-processing before feeding the processed structure data to structure encoder module 1213. For example, structure input processing module 1211 can convert the received structure data into backbone coordinates, or another format, that are compatible with structure encoder module 1213.

In some embodiments, structure encoder module 1213 is a processing module for encoding biological structure data into a latent encoding. For example, structure encoder module 1213 can receive structure data such as backbone coordinates. When applied to a query protein, the backbone coordinates can correspond to the spatial coordinates of specific atoms of a specific amino acid of the protein. Other formats can be used as well, such as formats the include all atomic coordinates for eventually generating all-atom structure latents or tokens. In various embodiments, structure encoder module 1213 maps the received structure data into a lower-dimensional latent space. The generated structure latents are encoded with context information associated with local structure such as the local structure of protein amino acids relative to their nearest neighboring amino acids. In various embodiments, structure encoder module 1213 utilizes geometric reasoning module 1215 to perform geometric attention on the structure data as part of the encoding process.

In some embodiments, geometric reasoning module 1215 is a processing module for performing geometric reasoning including a geometric form of self-attention on structure data. For example, for protein structure, geometric reasoning module 1215 can encode the structure of local amino acids based on their relative distance and direction to neighboring local amino acids. In some embodiments, the neighboring amino acids are determined by physical distance allowing geometric reasoning module 1215 to encode complex physical structure properties of proteins at a local level. For example, using direction and distance factors between local neighboring amino acids, self-attention scores can be determined. In some embodiments, the determined direction properties are attenuated based on the determined distance properties when determining self-attention scores. In various embodiments, geometric reasoning module 1215 utilizes a geometric attention mechanism block in addition to other functional components such as layer normalization and feed forward blocks.

In some embodiments, quantizing module 1217 is a processing module for quantizing structure latents. For example, the latent values encoded by structure encoder module 1213 are quantized by quantizing module 1217 to determine structure tokens. In various embodiments, quantizing module 1217 discretizes the structure latents generated by structure encoder module 1213 using a learned codebook. For example, similar latents can be mapped to similar codewords corresponding to biological structure tokens using clustering and/or vector quantization techniques. In some embodiments, quantizing module 1217 uses a vector quantizer to create tokens from structure latents.

In some embodiments, structure decoder module 1219 is a processing module for decoding biological structure tokens back into their original structure data space. For example, structure decoder module 1219 can map the lower-dimensional latent space used by structure tokens back to the structure data space used for the input to structure encoder module 1213. When applied to a query protein, the decoded results can be backbone coordinates that correspond to the spatial coordinates of specific atoms of specific amino acids of the predicted protein. In some embodiments, the decoded results can include coordinates for all relevant or all atoms of a biological object such as all atoms of a query protein.

In some embodiments, an additional post-processing step is performed to convert the decoded structure data to a format used as input to structure input processing module 1211.

Figure 13:
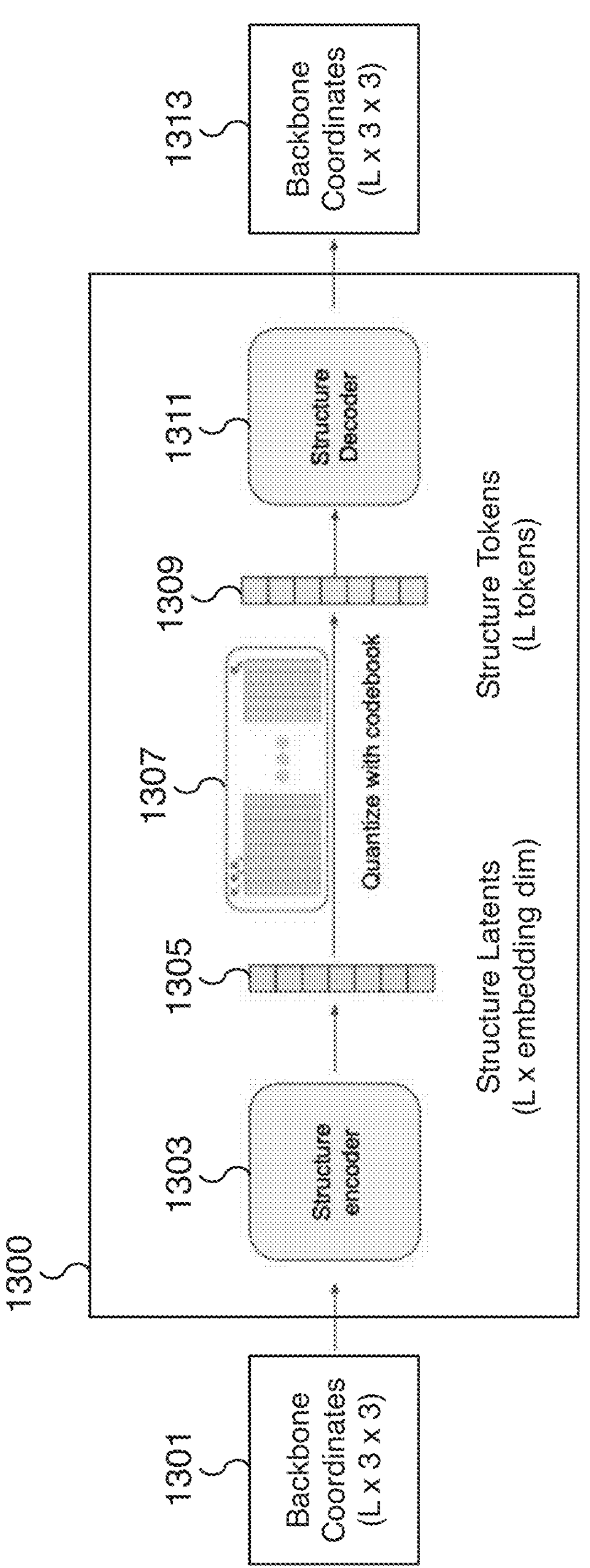
FIG. 13 is a block diagram illustrating an embodiment of a tokenizer for biological structure.

FIG. 13 is a block diagram illustrating an embodiment of a tokenizer for biological structure. In the example shown, structure tokenizer 1300 is an auto-encoder that can encode biological structure data into biological structure tokens and decode into biological structure tokens back to biological structure data. The encoded biological structure tokens are encoded with context information associated with local biological structure such as the local structure of protein amino acids relative to their nearest neighboring amino acids. In some embodiments, structure tokenizer 1300 is a variational autoencoder with vector quantization (VQ-VAE). As shown in FIG. 13, backbone coordinates 1301 are provided to structure encoder 1303, which generates structure latents 1305. Structure latents 1305 are quantized with quantizing module 1307 to generate structure tokens 1309. Structure tokens 1309 can be decoded by structure decoder 1311 to backbone coordinates 1313. In some embodiments, structure tokenizer 1300 corresponds to biological structure tokenizer module 1201 of FIG. 12, structure encoder 1303 corresponds to structure encoder module 1213 of FIG. 12, quantizing module 1307 corresponds to quantizing module 1217 of FIG. 12, and structure decode 1311 corresponds to structure decoder module 1219 of FIG. 12. In various embodiments, backbone coordinates 1301 are the output generated by structure input processing module 1211 of FIG. 12. In various embodiments, structure encoder 1303 can include a geometric reasoning block for encoding local structure. The geometric reasoning block can correspond to geometric reasoning module 1215 of FIG. 12.

In various embodiments, backbone coordinates 1301 and 1313 utilize a coordinates format for describing biological structure such as protein structure. In the example of FIG. 13, the structure data of backbone coordinates 1301 and 1313 each include backbone coordinates for a protein with L amino acids. Each of the L amino acids of the example protein have a local structure defined by three corresponding backbone atoms. The backbone atoms can correspond to nitrogen (N), alpha-carbon (CA), and carbon (C) atoms and each can be described by a set of three-dimensional spatial coordinates corresponding to X, Y, and Z coordinates. For a protein with L amino acids, the backbone coordinates have size L×3×3. When backbone coordinates 1301 are tokenized, the output is structure tokens 1309, which includes L tokens, one for each amino acid. When structure tokens 1309 are decoded, the output is decoded to backbone coordinates 1313. Although specific spatial and structure formats are described, alternative formats are appropriate as well. For example, structure encoder 1303 and structure decoder 1311 can utilize a different structure format such as a frame format that selects a single backbone atom as the origin and a rotation matrix based on the frame defined by the nitrogen (N), alpha-carbon (CA), and carbon (C) backbone atoms. As another example, in some embodiments, structure encoder 1303 and structure decoder 1311 can utilize a format that includes all atoms and all corresponding atomic coordinates for a biological object for encoding all-atom structure tokens.

Figure 14:
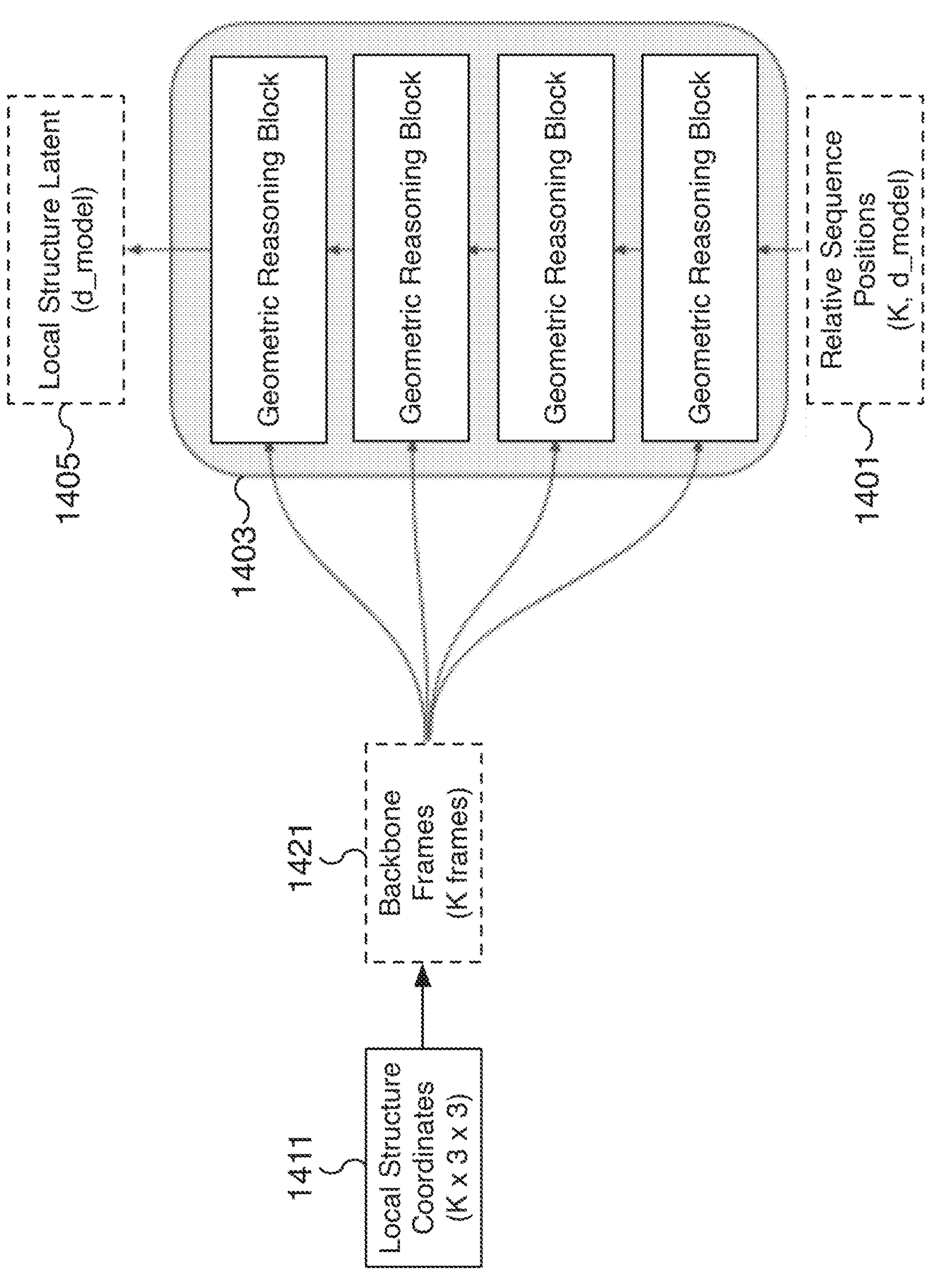
FIG. 14 is a block diagram illustrating an embodiment of a structure encoder of a biological structure tokenizer.

FIG. 14 is a block diagram illustrating an embodiment of a structure encoder of a biological structure tokenizer. In the example shown, structure encoder 1403 is a component of a biological structure tokenizer that encodes geometric biological structure. Structure encoder 1403 includes multiple instances of chained geometric reasoning blocks to apply geometric reasoning including geometric attention. Structure encoder 1403 receives relative sequence positions 1401 as input along with backbone frames 1421. Backbone frames are generated from local structure coordinates 1411. Structure encoder 1403 outputs local structure latent 1405. As shown in FIG. 14, the operation of structure encoder 1403 is applied to a single local reference target such as a query amino acid of a protein. In practice, structure encoder 1403 is applied to an entire query target (such as a query protein) and each query point (such as a query amino acid) can be processed in parallel. Although shown and described in FIG. 14 with respect to a particular local structure and backbone frames, structure encoder 1403 of a biological structure tokenizer can utilize other formats including all-atom formats for generating structure tokens. For example, in some embodiments, a structure encoder can generate all-atom structure tokens.

In some embodiments, local structure coordinates 1411 uses a coordinate format for local structure and includes local coordinates for K amino acids, each with three backbone atoms and each backbone atom with three coordinates (corresponding to X, Y, and Z coordinates). Depending on convention, the K amino acids can include the query point, such as the selected amino acid of the query protein. For example, for K=16, the query point and 15 other amino acids are described. The number K can be a hyperparameter and may have a configured value such as 16, 24, 32, etc., as appropriate. As shown in FIG. 14, local structure coordinates 1411 has size K×3×3. In some embodiments, local structure coordinates 1411 is converted to backbone frames 1421. For example, the K neighboring amino acids are converted to K frames, one for each of the K neighboring amino acids. The frame format can utilize an origin point and a rotation matrix. In various embodiments, structure encoder 1403 utilizes the frame format and receives backbone frames 1421 at each geometric reasoning block.

In some embodiments, relative sequence positions 1401 includes a vector that describes the relative position of the K amino acids of local structure coordinates 1411. For example, relative sequence positions 1401 can include K relative sequence position values with a second dimension based on the dimensions of the model (d_model). In some embodiments, a relative sequence position is a location offset and is based on the offset of a neighboring amino acid from the selected amino acid using the protein sequence for position ordering. For example, using the selected amino acid as a reference point, the selected amino acid has a relative sequence position with value 0, the previous amino acid has a relative sequence position with value −1, and the next amino acid has a relative sequence position with value 1. A subset of the K values of relative sequence positions 1401 may have relative sequence position values such as −3, −2, −1, 0, 1, 2, 3, 67, 68, −91, −92. In some embodiments, the sequence position values including the relative sequence position values are binned values. For example, relative sequence position values within than certain threshold range can be binned together.

In some embodiments, structure encoder 1403 corresponds to structure encoder module 1213 of FIG. 12 and/or structure encoder 1303 of FIG. 13. In some embodiments, local structure coordinates 1411 corresponds to at least a subset of coordinates of backbone coordinates 1301 of FIG. 13 and local structure latent 1405 corresponds to a latent result of structure latents 1305 of FIG. 13. In various embodiments, structure encoder 1403 may include additional components that are not shown.

Figure 15:
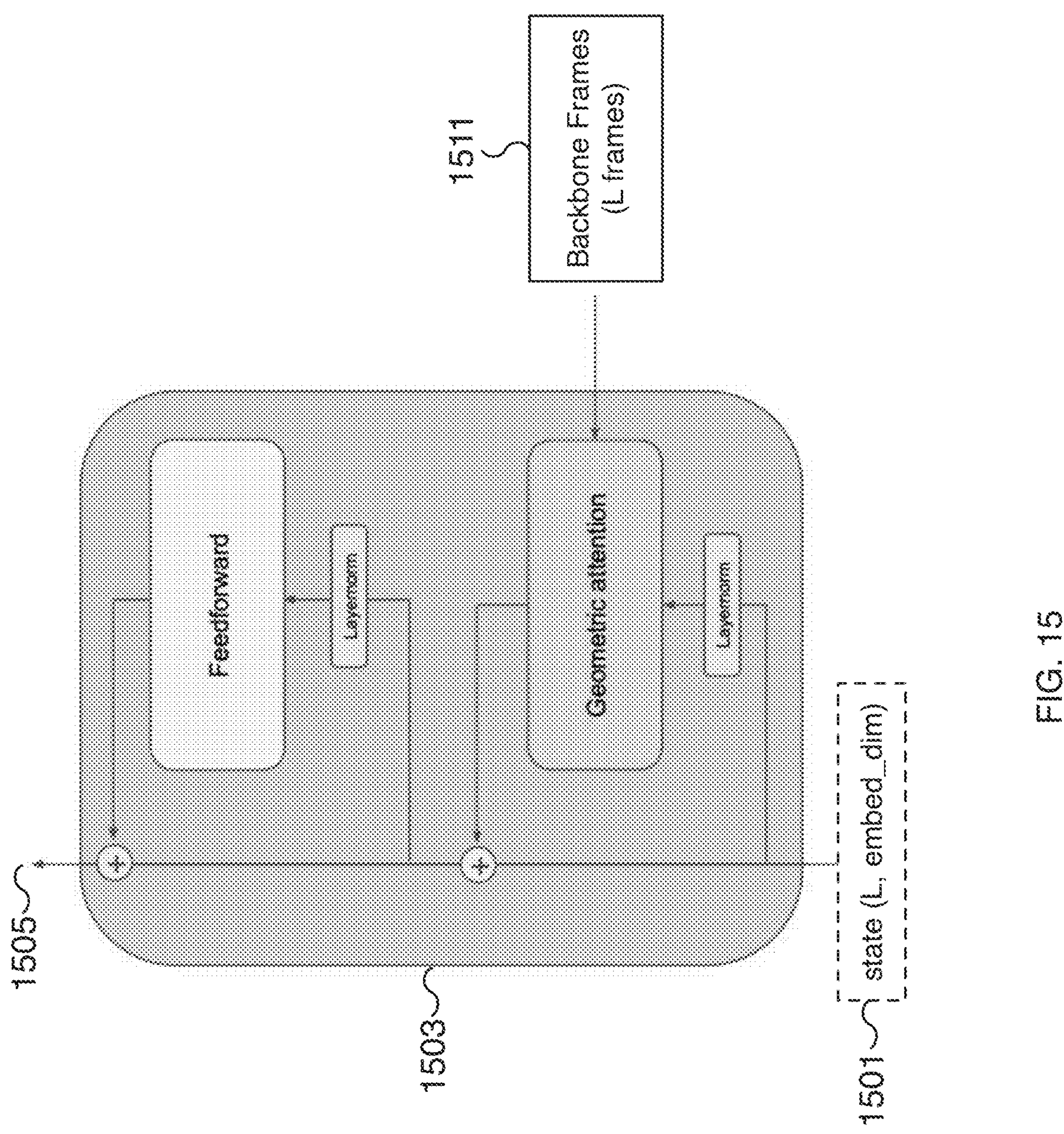
FIG. 15 is a block diagram illustrating an embodiment of a geometric reasoning block of a biological structure tokenizer.

FIG. 15 is a block diagram illustrating an embodiment of a geometric reasoning block of a biological structure tokenizer. In the example shown, geometric reasoning block 1503 is a component of a structure encoder of a biological structure tokenizer. Geometric reasoning block 1503 receives as input state information 1501 and backbone frames 1511. Geometric reasoning block 1503 includes multiple functional components including layer normalization, geometric attention, and feed forward blocks to determine updated state 1505. The arrangement of the functional components including layer normalization, geometric attention, and feed forward blocks of geometric reasoning block 1503 determines an updated representation of the state 1501 and is outputted as updated state 1505. In various embodiments, updated state 1505 reflects the application of geometric attention and feed forward networks.

In particular, the geometric attention block of geometric reasoning block 1503 includes geometric attention mechanisms to encode local geometric understanding. For example, for protein structure, the geometric attention mechanisms can encode an understanding of the local structure of each amino acid of a protein. In some embodiments, the geometric attention block determines local structure understanding for each amino acid based on the distance and direction of neighboring amino acids. In some embodiments, geometric reasoning block 1503 is utilized by geometric reasoning module 1215 of FIG. 12, structure encoder 1303 of FIG. 13, and/or structure encoder 1403 of FIG. 14. For example, structure encoder 1403 of FIG. 14 includes multiple instances of geometric reasoning block 1503.

In various embodiments, geometric reasoning block 1503 processes input state information 1501 and backbone frames 1511 for a biological object described by L positions of a sequence state, such as a protein described by L amino acids. For a specific position of the L positions of input state information 1501, the particular state information received can include local structure information such as the neighborhood context associated with that position. In some embodiments, the neighborhood context (not shown) includes as description of the K nearest neighbors, such as the K physically neighboring amino acids when describing the local structure of a specific amino acid of a protein. Additionally, each of the L positions of the biological object, such as each of the L amino acids of a protein, are described by one of the corresponding L frames of backbone frames 1511. Although shown and described in FIG. 15 with respect to backbone frames, in some embodiments, geometric reasoning block 1503 utilizes another format such as an all-atom format.

Figure 16:
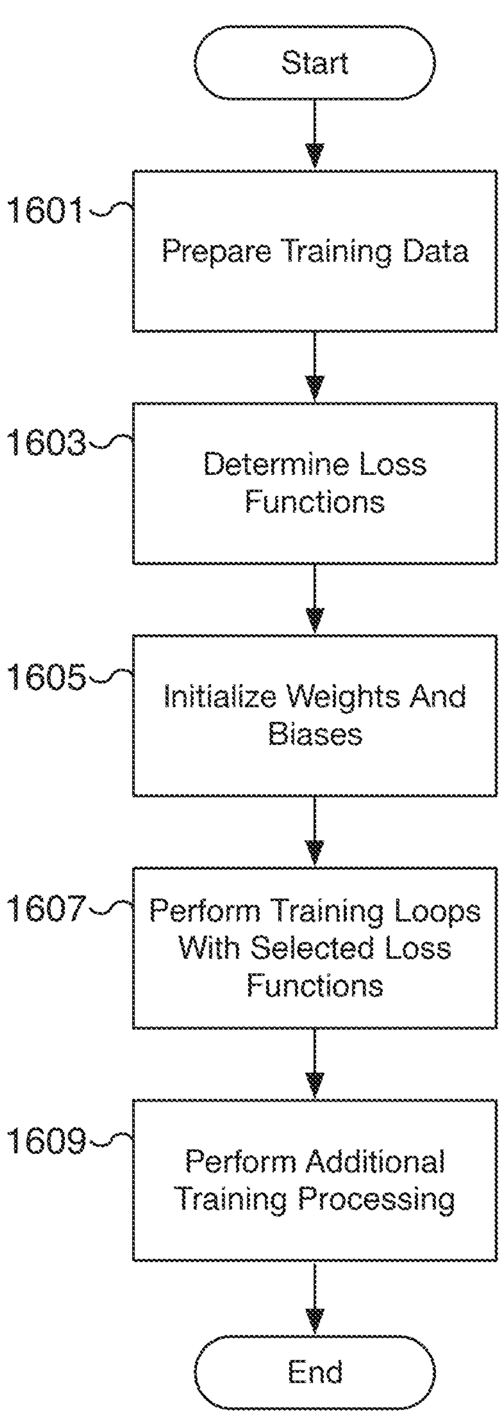
FIG. 16 is a flow chart illustrating an embodiment of a process for training a biological structure tokenizer.

FIG. 16 is a flow chart illustrating an embodiment of a process for training a biological structure tokenizer. For example, using the process of FIG. 16, a tokenizer for use with a biological language reasoning model is trained to encode biological structure including local structure into structure tokens. In some embodiments, the structure tokenizer utilizes geometric reasoning including geometric attention mechanisms to learn biological structure. The trained tokenizer can be used to tokenize training data for training a biological language reasoning model and/or for performing inference using the trained biological language reasoning model. In some embodiments, the biological structure tokenizer is an autoencoder and the associated decoder is used to decode structure tokens into biological structure. In some embodiments, the process of FIG. 16 is used to train a biological structure tokenizer including to determine the trained weights, biases, and/or codebook of biological structure tokenizer module 1201 of FIG. 12 and/or structure tokenizer 1300 of FIG. 13. In some embodiments, the process of FIG. 16 utilizes geometric reasoning module 1215 of FIG. 12 and/or geometric reasoning block 1503 of FIG. 15 to encode geometric biological structure including local geometric biological structure. In some embodiments, the process of FIG. 16 is performed at 701 of FIG. 7 and/or at 803 of FIG. 8 as part of the process of preparing tokenizers for performing biological language reasoning.

At 1601, training data is prepared. For example, the input data is preprocessed to prepare training data for the structure tokenizer. In some embodiments, the data is structure data such as protein structure data and the data is prepared into a format such as a format that extracts backbone atom coordinates. In some embodiments, the input data processed at 1601 corresponds to backbone coordinates 1301 of FIG. 13. In some embodiments, the input data is processed to prepare training data at least in part by determining a frame of reference for local structure, such as local structure of amino acids of a protein. In some embodiments, the training data is prepared using all atomic coordinates, for example, to train the biological structure tokenizer for generating all-atom structure tokens.

At 1603, one or more loss functions are determined. For example, one of more loss functions including geometric loss functions are selected for use during the training process. The determined geometric loss functions can be used during training to evaluate error measurements between input and reconstructed output. In various embodiments, geometric loss functions are selected to optimize the ability for the tokenizer to encode biological structure into latent geometric structure representations, to quantize the encoded structure latents into structure tokens, and to decode structure tokens back into a biological structure space of the input data. Different loss functions including different geometric loss functions can be utilized including at different phases of the training process. For example, a geometric loss function can be used for computing loss related to geometric distance and another for loss related to geometric direction. As another example, different geometric loss functions that classify geometric loss based on bins can be utilized, for example, early in the training cycle when the error loss can be large. For example, a distogram-based geometric loss function can be used to bin the relative distance between amino acids and/or an anglogram-based geometric loss function can be used to bin the relative direction or orientation of amino acids.

In some embodiments, a geometric distance loss function is used. For example, a geometric distance loss function can be used during training for structure prediction including for the prediction of structure coordinates such as protein structure coordinates. In some embodiments, the geometric distance loss is computed based on pairwise distances between backbone atoms, such as the backbone atoms of amino acids for a protein. For example, pairwise distances are computed between all pairs of atoms in the ground truth structure. The resulting matrix has dimension 3L×3L corresponding to three backbone atoms per position and the L sequence length of the protein. The same matrix for the predicted structure is computed and an error loss between the two matrices is determined. In some embodiments, the error loss computed is a mean squared error loss between the two matrices. Although the previous example is described with respect to protein backbone atoms and an example corresponding 3L×3L resulting matrix, the approach can be extended to any number of atoms in the structure. For example, the geometric distance loss function can be applied to all side chain atoms in a protein structure, or for interactions with other biological molecules.

In some embodiments, a geometric direction loss function is used. For example, a geometric direction loss function can be used during training for structure prediction including for the prediction of structure coordinates such as protein structure coordinates. In some embodiments, the geometric direction loss is modeled using a function based on the relative orientations of bond vectors in the predicted and ground truth structures and is applicable to any biological molecule. For example, the bond vectors and Z-axis vectors for all selected atoms in the ground truth and predicted structures can be computed. The Z-axis vectors can be defined as the cross product between any two bonds for a given atom. In the event an atom has fewer than two bonds, no Z-axis is computed. Next, the dot products between all pairs of vectors in the ground truth structure are computed. The resulting matrix has dimensions approximately 2*N, where N corresponds to the number of atoms in the ground truth structure. In various embodiments, N is an approximation since, for example, not all atoms may have defined Z-axis vectors. The corresponding dot product computations are repeated for the predicted structure vectors and an error loss between the ground truth and predicted structure matrices is determined. In some embodiments, the error loss computed is a mean squared error loss between the two matrices. In various embodiments, when the geometric direction loss function is applied to protein structure, the backbone vectors and Z-axis vectors for all residues in the ground truth and predicted structures are computed. Next, the dot products between all pairs of vectors in the ground truth structure are computed. The resulting matrix has dimensions 6L×6L, where the protein has a sequence length of L. The dot product computations are repeated for the predicted structure vectors and an error loss between the ground truth and predicted structure matrices is determined.

In some embodiments, the computed backbone vectors for the geometric direction loss function correspond to the vectors between the three backbone atoms of a residue. The backbone atoms can correspond to nitrogen (N), alpha-carbon (CA), and carbon (C) atoms and each can be described by a set of three-dimensional spatial coordinates corresponding to X, Y, and Z coordinates. In some embodiments, the three backbone vectors are the vectors defined by the nitrogen and alpha-carbon atoms (N→CA), the alpha-carbon and carbon atoms (CA→C), and the carbon and nitrogen atoms (C→N). The three additional Z-axis vectors can be determined by the cross-product applied to each different pair of backbone vectors. In some embodiments, the three Z-axis vectors correspond to the vectors (N→CA)×(CA→C), (CA→C)×(C→N), and (C→N)×(N→CA). Although the geometric direction loss function is described above with six specific vectors, other sets of vectors such ones relying on the X-axis and/or Y-axis vectors or another combination of vectors can be used as well.

In some embodiments, a geometric loss function can be used that relies on determining three vectors for each residue. For example, an anglogram-based or binned direction classification geometric loss function can be used during training for structure prediction including for the prediction of structure coordinates such as protein structure coordinates. In some embodiments, the geometric loss is computed based on computing two backbone vectors and a third orthogonal vector such as the Z-axis vector that can be determined by the cross-product of the two selected backbone vectors. In some embodiments, the three vectors are centered around the alpha-carbon atom and correspond to the vectors (N→CA), (CA→C), and (N→CA)× (CA→C). In some embodiments, the geometric loss is computed based on the relative orientations of the three vectors in the predicted and ground truth structures. For example, when applied for protein structure, the two backbone vectors and the Z-axis vector are computed for the ground truth structure. Next, the cosine similarity between all pairs of vectors is computed. The resulting matrix has dimensions 3L×3L, where the protein has a sequence length of L. The similarities are then binned into, for example, 16 bins, and each of the bins is then classified. In some embodiments, the anglogram-based geometric loss function provides improved results particularly when applied early in the training cycle when the determined geometric loss can be large. Although described above with respect to two particular backbone vectors and a corresponding Z-axis vector, another set of three appropriate vectors to define a residue can be used as well.

At 1605, the weights and biases of the tokenizer are initialized. For example, the weights and biases of the encoder, decoder, and quantizer are initialized. The values for the weights and biases may be initialized with a random initialization technique.

At 1607, training loops are performed with the selected loss functions. For example, multiple iterations of a training loop are performed to train the biological structure tokenizer. In some embodiments, the training process utilizes geometric reasoning including geometric attention mechanisms and the loss functions selected at 1603. For example, the weights and biases initialized at 1605 are updated during each pass through the training loop and the selected loss functions are applied to minimize loss. In various embodiments, the structure tokenizer includes a quantization step and the quantizer is updated during the training process. In some embodiments, the training loops are performed until a target error rate is reached and/or for a configured number of epochs.

At 1609, additional training processing is performed. For example, additional processing can be performed after the completion of the main training loops at 1607. In some embodiments, the additional processing includes additional fine-tuning and/or additional processing to the structure tokenizer to improve its performance. In some embodiments, an additional processing step includes storing the trained weights, biases, and codebook results and/or deploying the trained structure tokenizer for use in performing biological language reasoning tasks.

Figure 17:
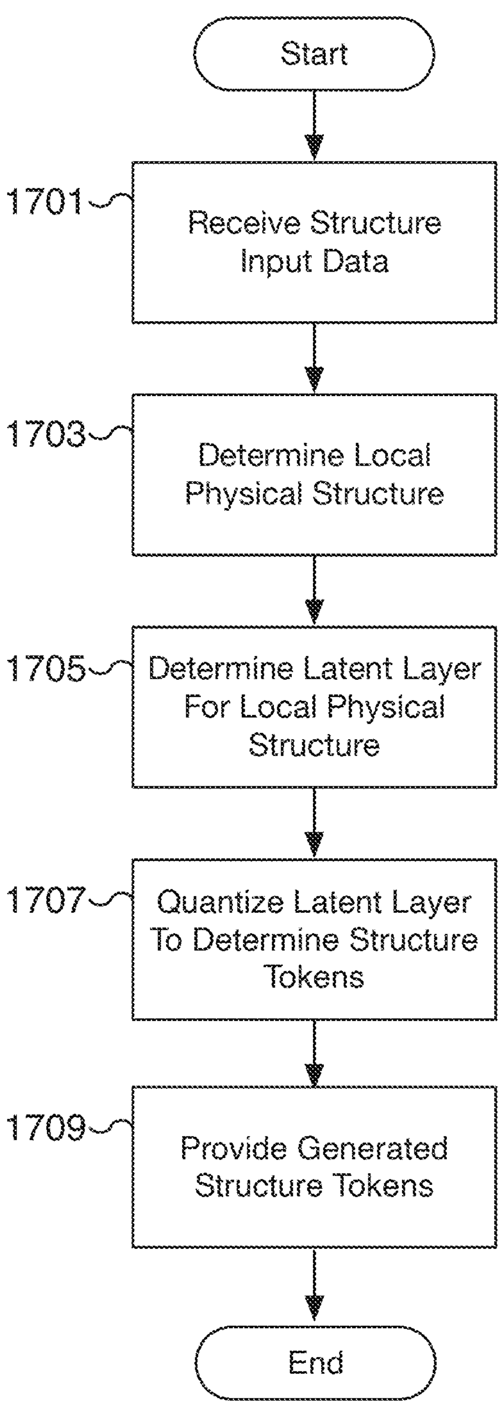
FIG. 17 is a flow chart illustrating an embodiment of a process for tokenizing biological structure.

FIG. 17 is a flow chart illustrating an embodiment of a process for tokenizing biological structure. For example, using the process of FIG. 17, a structure tokenizer is applied to generate structure tokens that encode biological structure including local structure from biological structure input data. The generated structure tokens can be used for training and/or performing inference with respect to a biological language reasoning model. In some embodiments, the tokenizing is performed for a specific biological domain such as for a specific protein or query protein to encode the biological structure of the protein including its local structure with respect to the amino acids of the protein. In some embodiments, the structure tokenizer utilizes geometric reasoning including geometric attention mechanisms. In some embodiments, the biological structure tokenizer is an autoencoder and the associated decoder is used to decode structure tokens into a decoded format of biological structure data. In some embodiments, the process of FIG. 17 is performed at 701, 703, and/or 707 of FIG. 7, at 805 of FIG. 8, at 903 of FIG. 9, at 1005 of FIG. 10, at 1105 of FIG. 11, and/or at various steps when structure data requires tokenizing for biological language reasoning. In some embodiments, the process of FIG. 17 is performed by biological structure tokenizer module 1201 of FIG. 12 and/or structure tokenizer 1300 of FIG. 13. In some embodiments, the process of FIG. 17 is performed using geometric reasoning module 1215 of FIG. 12 and/or geometric reasoning block 1503 of FIG. 15 to encode geometric biological structure including local geometric biological structure.

At 1701, structure input data is received. For example, structure input data for a biological target such as a query protein is received. The data can be provided in a format that describes biological structure such as with coordinates for backbone atoms. For example, when applied to protein structure, the coordinates of backbone atoms for each specified amino acid of a protein can be received. Alternative formats are appropriate as well based and can vary depending on the trained structure tokenizer. For example, in some embodiments, the format utilizes an all-atom format for generating all-atom structure tokens. In some embodiments, the structure input data format includes and/or utilizes backbone frames such as a frame format that describes local structure. For example, a frame can describe an origin, such as the coordinates of an origin for a specific backbone atom, and a corresponding rotation matrix to orient the local structure. In some embodiments, the structure input data corresponds to backbone coordinates 1301 of FIG. 13 and/or local structure coordinates 1411 of FIG. 14.

At 1703, the local physical structure is determined. For example, the local physical structure of the biological target is determined. In various embodiments, determining the local structure includes identifying local reference points and the corresponding surrounding structure of each reference point. For example, for a target protein, the local structure can be determined using each amino acid of the protein as a separate reference point. In various embodiments, the local structure of an amino acid of a protein can be based on its neighboring amino acids as determined by physical distance. Due to the physical structure of a protein, the determined neighboring amino acids typically differ from the amino acid sequence for the protein. Although described with respect to a protein, the local physical structure can be determined for the biological target using similar techniques.

At 1705, a latent layer is determined for the local physical structure. For example, structure latents for the local physical structure of the biological target are determined using the trained structure encoder of the structure tokenizer such as structure encoder module 1213 of FIG. 12, structure encoder 1303 of FIG. 13, and/or structure encoder 1403 of FIG. 14. In various embodiments, the determined structure latents encode local physical structure including neighboring structure for each local reference point. For example, for a target protein, structure latents can be determined for each described amino acid of the protein based on its neighboring amino acids. In various embodiments, the determined structure latents encode local geometric structure in a lower-dimensional latent space by applying geometric reasoning. In some embodiments, the determined structure latents correspond to structure latents 1305 of FIG. 13 and/or instances of local structure latent 1405 of FIG. 14.

At 1707, the latent layer is quantized to determine structure tokens. For example, the latent layer determined at 1705 is quantized using a quantizer or quantizing module such as quantizing module 1217 of FIG. 12 and/or quantizing module 1307 of FIG. 13 to determine a structure token for each local reference point. In various embodiments, structure tokens are created using a learned codebook. For example, similar latents can be mapped to similar codewords corresponding to biological structure tokens using clustering and/or vector quantization techniques. In some embodiments, the determined structure tokens correspond to structure tokens 1309 of FIG. 13.

At 1709, the generated structure tokens are provided. For example, the set of structure tokens determined at 1707, such as structure tokens for each amino acid of a query protein, are provided. The generated structure tokens can be used for training and/or for inference with a biological language reasoning model. For example, the generated structure tokens can be provided for preparing a structure track as part of a multi-track input, such as masked multi-track input 301 of FIG. 3, for a multi-track biological language model.

Figure 18:
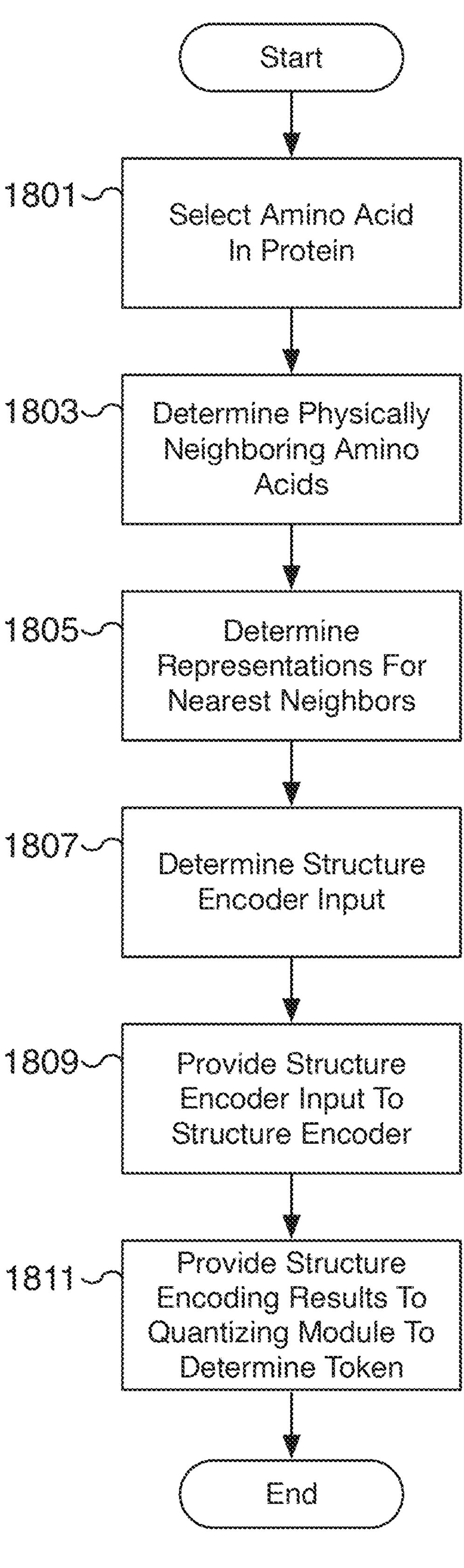
FIG. 18 is a flow chart illustrating an embodiment of a process for tokenizing a biological protein structure.

FIG. 18 is a flow chart illustrating an embodiment of a process for tokenizing a biological protein structure. For example, the process of FIG. 18 can be applied for each amino acid in a target (or query) protein to create a corresponding structure token. When applied to an entire protein, the set of corresponding structure tokens represents the entire protein's physical structure with latent encodings for local structure. The generated structure tokens can be used for training and/or performing inference with respect to a biological protein language reasoning model. In some embodiments, the structure tokenizer utilizes geometric reasoning including geometric attention mechanisms. In some embodiments, the protein structure tokenizer is an autoencoder and the associated decoder is used to decode protein structure tokens into a decoded format of protein structure data, for example, to visualize a generated protein.

In some embodiments, the process of FIG. 18 is performed at 701, 703, and/or 707 of FIG. 7, at 805 of FIG. 8, at 903 of FIG. 9, at 1005 of FIG. 10, at 1105 of FIG. 11, at 1703, 1705, 1707, and/or 1709 of FIG. 17, and/or at various steps when protein structure data requires tokenizing for biological language reasoning. In some embodiments, the process of FIG. 18 is performed by biological structure tokenizer module 1201 of FIG. 12 and/or structure tokenizer 1300 of FIG. 13. In some embodiments, the process of FIG. 18 is performed using geometric reasoning module 1215 of FIG. 12 and/or geometric reasoning block 1503 of FIG. 15 to encode geometric biological structure including local geometric biological structure.

At 1801, an amino acid in a protein is selected. For example, the process of FIG. 18 is performed over an entire protein for each amino acid described (or unmasked) for the protein. At 1801, a specific amino acid in a protein is selected for tokenization. In various embodiments, the process of FIG. 18 can be performed in parallel for each selected protein.

At 1803, physically neighboring amino acids are determined. For example, the nearest amino acids by physical distance to the amino acid selected at 1801 are selected. In some embodiments, the physically neighboring amino acids are determined by determining the distance between each specific amino acid and candidate amino acids of the protein. Based on the determined distance between a specific amino acid and a candidate amino acid, the candidate amino acid is included as one of the physically neighboring amino acids. In some embodiments, a total of K physically neighboring amino acids are selected, where the number K is configurable and can be a hyperparameter. In various embodiments, the physical distance can be determined by calculating the distance, such as the Euclidean distance, between reference points for each amino acid pair. For example, a reference location can be selected for a specific amino acid and a candidate amino acid. The reference location of an amino acid can include a coordinate for an origin location and a corresponding rotation matrix for the amino acid. In some embodiments, the origin location corresponds to the coordinates of a nitrogen (N), alpha-carbon (CA), or carbon (C) atom of the amino acid. Based on the selected reference locations, a distance is determined between an amino acid pair and used to determine whether a candidate amino acid is one of the nearest neighbors of the selected amino acid. Other techniques for determining the physically neighboring amino acids are appropriate as well. In various embodiments, the physically neighboring amino acids can include amino acids from another protein such as a binder protein or a binding target protein.

At 1805, representations for the physically neighboring amino acids are determined. For example, representations for the physically neighboring amino acids determined at 1803 are generated. In some embodiments, the representations utilize a frame format for each backbone atom of the amino acid. For example, a frame format for an amino acid can include the coordinates of the alpha-carbon atom of the amino acid and a 3×3 rotation matrix for the frame defined by the nitrogen, alpha-carbon, and carbon atoms of the amino acid. In some embodiments, the alpha-carbon is placed at the origin and the nitrogen atom defines the X-axis. Although specific spatial and structure formats are described, alternative representation formats are appropriate as well. For example, another reference point other than the nitrogen atom of a backbone can be used to define the X-axis. In some embodiments, the representations for the physically neighboring amino acids include a relative sequence position of each neighboring amino acid relative to the selected (or query) amino acid. For example, the representations for the physically neighboring amino acids can include a vector of sequence positions. In some embodiments, a relative sequence position is a location offset based on the offset of a neighboring amino acid from the selected amino acid using the protein sequence for position ordering. For example, using the selected amino acid as a reference point, the selected amino acid has a relative sequence position with value 0, the previous amino acid has a relative sequence position with value −1, and the next amino acid has a relative sequence position with value 1. In some embodiments, the determined representations for the physically neighboring amino acids correspond to relative sequence positions 1401 of FIG. 14, local structure coordinates 1411 of FIG. 14, and/or backbone frames 1421 of FIG. 14.

At 1807, input for a structure encoder is determined. For example, using the determined representations for the physically neighboring amino acids determined at 1805, a structure encoder input is determined. The determined input can include backbone frames for the physically neighboring amino acids and the relative sequence position for the physically neighboring amino acids. In some embodiments, the structure encoder input includes the selected (or query) amino acid as a neighboring amino acid, for example, with a relative sequence position with value 0. In some embodiments, the structure encoder input includes relative sequence positions 1401 of FIG. 14. In some embodiments, the structure encoder input is based on relative sequence positions 1401 of FIG. 14 and backbone frames 1421 of FIG. 14. In some embodiments, the structure encoder input includes all atomic coordinates, for examples, for generating all-atom structure tokens.

At 1809, structure encoder input is provided to the structure encoder. For example, the structure encoder input determined at 1807 is provided to the structure encoder of the trained structure tokenizer. The structure encoder encodes the provided input into one or more structure latent values. In various embodiments, the structure encoder applies one or more geometric reasoning blocks to encode local structure. In some embodiments, the structure encoder corresponds to structure encoder module 1213 of FIG. 12, structure encoder 1303 of FIG. 13, and/or structure encoder 1403 of FIG. 14.

At 1811, the structure encoding results are provided to a quantizing module for tokenization. For example, the structure latent results determined at 1809 by the structure encoder are provided to a quantizing module for quantization. In some embodiments, the quantizing module is quantizing module 1217 of FIG. 12 and/or quantizing module 1307 of FIG. 13. The output of the quantizing module is a structure token for the amino acid selected at 1801. In some embodiments, the structure token is created using a learned codebook. In some embodiments, the determined structure token is a structure token of structure tokens 1309 of FIG. 13.

Figure 19:
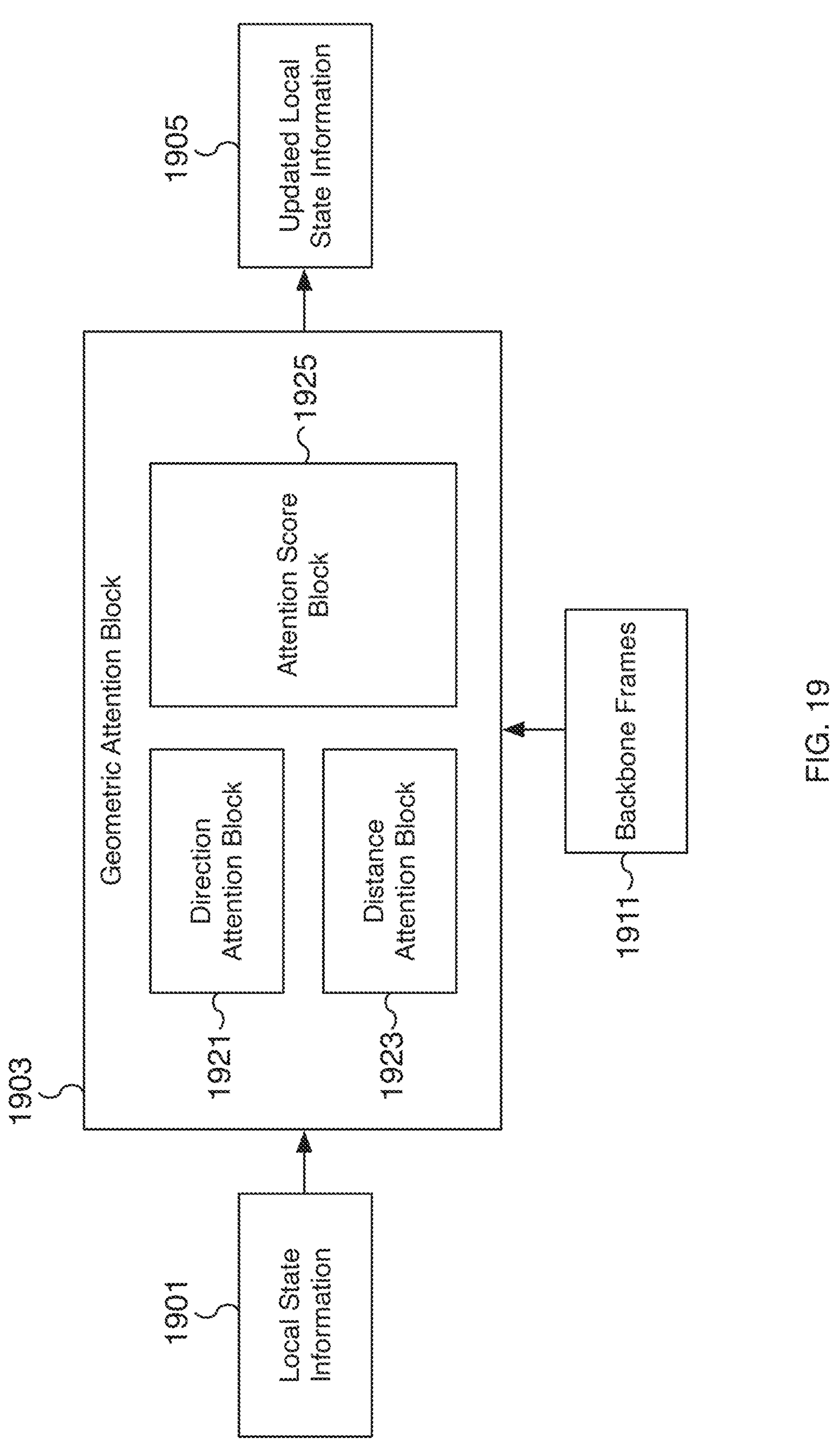
FIG. 19 is a block diagram illustrating an embodiment of a geometric attention block for performing geometric attention on biological structure.

FIG. 19 is a block diagram illustrating an embodiment of a geometric attention block for performing geometric attention on biological structure. For example, geometric attention block 1903 is trained to determine and apply geometric attention using local state information 1901 and backbone frames 1911 as inputs. Within geometric attention block 1903, direction attention block 1921 and distance attention block 1923 determine intermediary direction and distance attention score results using local state information 1901 and backbone frames 1911. The attention results of direction attention block 1921 and distance attention block 1923 are used by attention score block 1925 to determine a geometric attention result. As a result, local state information 1901 is updated using the determined geometric attention result and outputted as updated local state information 1905. In various embodiments, updated local state information 1905 includes a geometric attention result with geometric attention scores and an updated sequence state with updated weighted sequence representations. Although shown and described in FIG. 19 with respect to backbone frames, in some embodiments, geometric reasoning block 1903 utilizes another format such as an all-atom format.

In various embodiments, geometric attention block 1903 can be one of multiple geometric attention blocks that are chained together to apply geometric attention. In some embodiments, the geometric attention is applied to protein structure to encode local protein structure information. In some embodiments, geometric attention block 1903 corresponds to the geometric attention mechanism used by transformer block with geometric attention 541 of FIG. 5, transformer block with a geometric attention 603 of FIG. 6, and/or geometric reasoning block 1503 of FIG. 15.

In some embodiments, geometric attention block 1903 is utilized by geometric reasoning module 415 of FIG. 4 and/or geometric reasoning module 1215 of FIG. 12. In some embodiments, a biological language reasoning model such as the model corresponding to or associated with biological language model service 111 of FIG. 1, biological language model service 201 of FIG. 2, biological language model 303 of FIG. 3, and/or biological language model module 401 of FIG. 4 incorporates one or more instances of geometric attention block 1903. In some embodiments, a structure encoder such as structure encoder 1303 of FIG. 13 and/or structure encoder 1403 of FIG. 14 incorporates one or more instances of geometric attention block 1903.

As shown in FIG. 19, geometric attention block 1903 includes components direction attention block 1921, distance attention block 1923, and attention score block 1925. Other components of geometric attention block 1903 may exist but are not shown. In various embodiments, direction attention block 1921 is an attention block that determines an attention score based on the direction a local query object of a target object is to its local neighbors. For example, the direction (or orientation) of a query amino acid of a protein is compared to its neighboring amino acids. Similarly, distance attention block 1923 is an attention block that determines an attention score based on the distance a local query object of a target object is to its neighbors. For example, the distance between a query amino acid of a protein from each of its neighboring amino acids is determined. In various embodiments, distance attention block 1923 and attention score block 1925 each determine and utilize corresponding direction and distance, query and key vectors, respectively, for example, to apply separate learning parameters when determining attention scores.

In various embodiments, the determined direction and distance attention results of direction attention block 1921 and distance attention block 1923, respectively, are processed by attention score block 1925. For example, attention score block 1925 can determine a weighted attention score by applying learned and/or configured weights to direction attention and distance attention results. In various embodiments, a value vector is used to compute the geometric attention result. In some embodiments, rotation matrices are applied to the value vector and inverse rotation matrices are applied to the geometric attention result so that each is in alignment with the appropriate frame of reference. In some embodiments, the weighted attention scores undergo a normalization process as part of determining the geometric attention result.

In some embodiments, local state information 1901 can be initialized to include local state information, such as local state information for each amino acid in a protein. The included local information for a specific amino acid can include references to its neighboring amino acids. For example, a list of a specific amino acid's neighbors based on their offsets in the protein sequence can be included in an initial version of local state information 1901. In some embodiments, local state information 1901 corresponds to and/or reflects an updated version of state information 601 of FIG. 6 and/or relative sequence positions 1401 of FIG. 14.

In some embodiments, backbone frames 1911 includes local physical structure information, such as local amino acid structure information using a frame format. For example, a backbone frame can specify an origin and rotation matrix for a specific amino acid based on the backbone atoms of the amino acid. In some embodiments, backbone frames 1911 corresponds to backbone frames 521 of FIG. 5, backbone frames 621 of FIG. 6, and/or backbone frames 1421 of FIG. 14.

Figure 20:
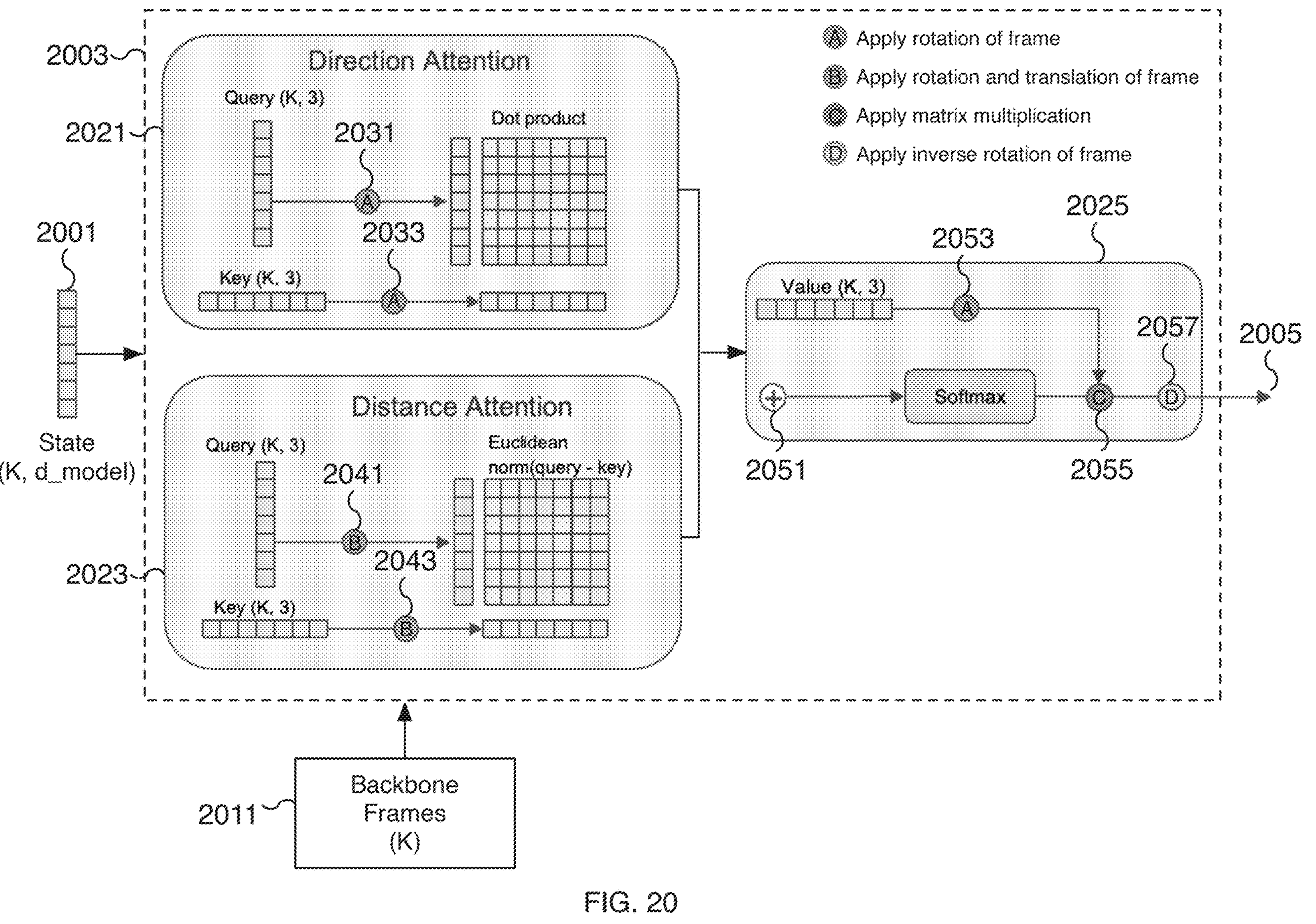
FIG. 20 is a block diagram illustrating an embodiment of a geometric attention block for performing geometric attention on biological structure.

FIG. 20 is a block diagram illustrating an embodiment of a geometric attention block for performing geometric attention on biological structure. For example, geometric attention block 2003 is trained to determine and apply geometric attention using local state information 2001 and backbone frames 2011 as inputs. Within geometric attention block 2003, direction attention block 2021 and distance attention block 2023 determine intermediary direction and distance attention score results using local state information 2001 and backbone frames 2011. The attention results of direction attention block 2021 and distance attention block 2023 are used by attention score block 2025 to determine a geometric attention result. Using the determined geometric attention result, local state information 2001 is updated by attention score block 2025 and outputted as updated local state information 2005. In some embodiments, geometric attention block 2003 is geometric attention block 1903 of FIG. 19 with additional implementation details for performing geometric attention. For example, local state information 2001 is local state information 1901 of FIG. 19, backbone frames 2011 is backbone frames 1911 of FIG. 19, direction attention block 2021 is direction attention block 1921 of FIG. 19, distance attention block 2023 is distance attention block 1923 of FIG. 19, attention score block 2025 is attention score block 1925 of FIG. 19, and/or updated local state information 2005 is updated local state information 1905 of FIG. 19. As shown in the legend of FIG. 20, computational operations 2031, 2033, and 2053 are denoted with the letter A and each corresponds to frame rotation operations, computational operations 2041 and 2043 are denoted with the letter B and each corresponds to combined frame rotation and translation operations, computational operation 2055 is denoted with the letter C and corresponds to matrix multiplication operations, and computational operation 2057 is denoted with the letter D and corresponds to frame inverse rotation operations. Although shown and described in FIG. 20 with respect to backbone frames, in some embodiments, geometric reasoning block 2003 utilizes another format such as an all-atom format.

In some embodiments, direction attention block 2021 receives local state information 2001 and backbone frames 2011 as inputs. Local state information 2001 is used by direction attention block 2021 to create direction query and direction key vectors. Computational operations 2031 and 2033 are applied to direction query and direction key vectors, respectively, to rotate the direction query and direction key vector elements by the rotation transformations of their respective frames using rotation transformations from backbone frames 2011. In various embodiments, computational operations 2031 and 2033 each corresponds to matrix multiplication operations to apply rotation transformations. For example, the K frames of backbone frames 2011 can include corresponding 3×3 rotation matrices that are applied position-wise to the appropriate elements of local state information 2001. In particular embodiments, the dimension K corresponds to the number of local neighbors, such as the K amino acids in the local physical structure context of a specific amino acid. The resulting direction query and direction key vectors are used to determine a direction attention result. In some embodiments, the direction attention result scores are determined using dot product operations on direction query and direction key vector elements. Direction attention block 2021 provides the direction attention result to attention score block 2025.

In some embodiments, distance attention block 2023 receives local state information 2001 and backbone frames 2011 as inputs. Local state information 2001 is used by distance attention block 2023 to create distance query and distance key vectors. Computational operations 2041 and 2043 are applied to distance query and distance key vectors, respectively, to rotate and translate the distance query and distance key vector elements by the rotation and translation transformations of their respective frames using rotation and translation transformations from backbone frames 2011. In various embodiments, computational operations 2041 and 2043 each corresponds to matrix multiplication and vector addition operations to apply rotation and translation transformations. For example, the K frames of backbone frames 2011 can include corresponding 3×3 rotation matrices and 3×1 translation vectors that are applied position-wise to the appropriate elements of local state information 2001. In particular embodiments, the dimension K corresponds to the number of local neighbors, such as the K amino acids in the local physical structure context of a specific amino acid. The resulting distance query and distance key vectors are used to determine a distance attention result. In some embodiments, the distance attention result scores are determined using Euclidean norm operations on the difference between corresponding distance query and distance key vector element values. Distance attention block 2023 provides the distance attention result to attention score block 2025.

In some embodiments, attention score block 2025 receives local state information 2001, backbone frames 2011, a direction attention result from direction attention block 2021, and a distance attention result from distance attention block 2023 as inputs. Attention score block 2025 outputs a geometric attention result that corresponds to updated local state information 2005. In various embodiments, attention score block 2025 determines a weighted attention result with weighted attention result computation 2051 based on direction attention and distance attention results, for example, to attenuate the direction attention result scores by the distance attention result scores. In some embodiments, intermediate weighted direction attention result and intermediate weighted distance attention result are determined by applying learned and/or configured direction and distance term weights, respectively, to the direction attention and distance attention results. The intermediate weighted distance result scores are then subtracted from the intermediate weighted direction result scores to determine a weighted attention result. For example, for a particular element of a weighted attention result, a weighted attention score for $element_{ij}$ can be determined with weighted attention result computation 2051 by computing $element_{ij}$=weight_direction*direction_term−weight_distance*distance_term. In various embodiments, geometric attention block 2003 learns the per-head distance and direction term weights that are applied when computing weighted attention scores for a weighted attention result.

In various embodiments, the weighted attention result determined at weighted attention result computation 2051 is provided to a softmax module to apply a softmax function. For example, a softmax function is applied to normalize the weighted attention scores of the weighted attention result into a valid probability distribution. In parallel to the softmax module, attention score block 2025 creates a value vector using local state information 2001 and backbone frames 2011 as input. Computational operation 2053 is applied to the value vector to rotate the value vector elements by the rotation transformations of their respective frames using rotation transformations from backbone frames 2011. In various embodiments, computational operation 2053 corresponds to matrix multiplication operations to apply rotation transformations, and computational operation 2053 functions similar to computational operations 2031 and 2033 described above.

As shown in FIG. 20, the resulting transformed value vector of attention score block 2025 is used to determine a geometric attention result by applying computational operation 2055 and computational operation 2057. Computational operation 2055 performs a matrix multiplication using the normalized weighted attention result and the transformed value vector. Computational operation 2057 applies an inverse rotation transformation to the result of computational operation 2055 to transform the geometric attention result into the appropriate frame of reference. In various embodiments, the rotation transformation applied at computational operation 2057 corresponds to the inverse of the rotation transformation applied at computational operation 2055. In various embodiments, attention score block 2025 updates the local state with the computed geometric attention result and outputs the geometric attention result as updated local state information 2005. In various embodiments, updated local state information 2005 includes the determined geometric attention result with geometric attention scores and an updated sequence state with updated weighted sequence representations. In some embodiments, updated local state information 2005 is the input source to a downstream geometric attention block, for example, when multiple geometric attention blocks are chained together. In some embodiments, the chained functionality includes additional functional blocks such as layer normalization and feed forward blocks. In various embodiments, geometric attention block 2003 applies geometric attention to sequence state information received as local state information 2001 and outputs updated sequence state information as updated local state information 2005.

Figure 21:
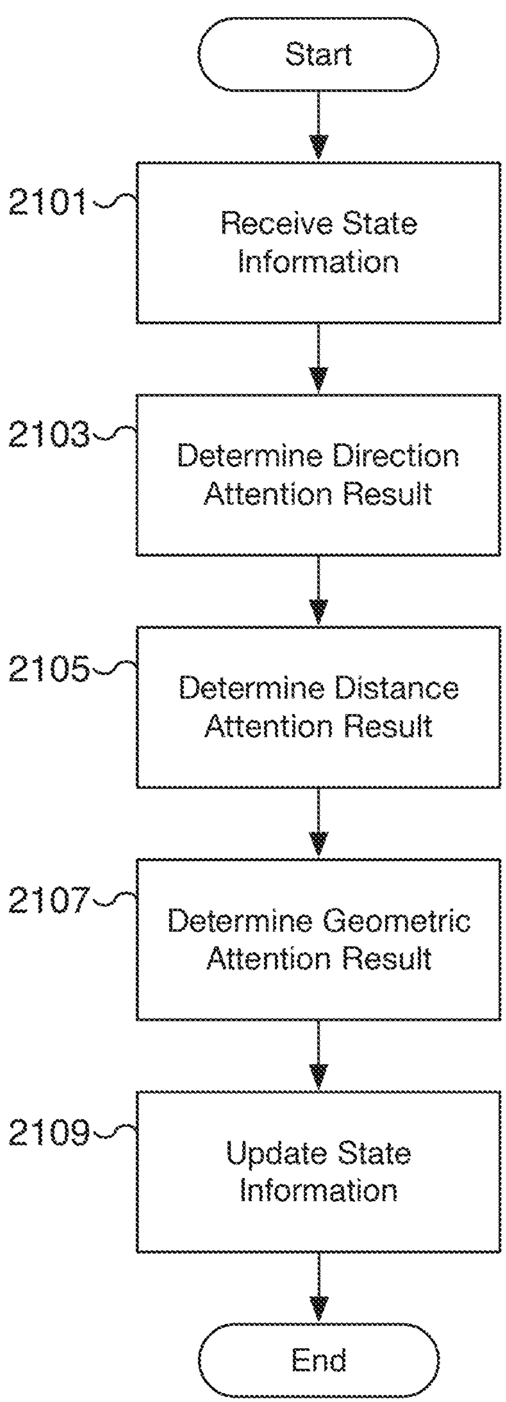
FIG. 21 is a flow chart illustrating an embodiment of a process for performing geometric attention on biological structure.

FIG. 21 is a flow chart illustrating an embodiment of a process for performing geometric attention on biological structure. For example, using the process of FIG. 21, a geometric attention block can determine geometric attention scores from local state and structure inputs. In some embodiments, the process of FIG. 21 updates state information based on a geometric attention result which can be forwarded to additional geometric attention blocks, as appropriate. The process of FIG. 21 can be performed as part of a process for tokenizing local structure for a biological domain such as for protein structure. By applying geometric attention to biological structure data, long-range geometric dependencies and/or contextual relationships between different elements within a biological object, such as between amino acids of a protein, can be captured. In some embodiments, the process of FIG. 21 is performed when performing biological language reasoning using biological structure data. In some embodiments, the process of FIG. 21 is performed by geometric attention block 1903 of FIG. 19 and/or geometric attention block 2003 of FIG. 20.

In some embodiments, the process of FIG. 21 is one of the processes performed by transformer block with geometric attention 541 of FIG. 5, transformer block with a geometric attention 603 of FIG. 6, and/or geometric reasoning block 1503 of FIG. 15. Similarly, the process of FIG. 21 can be one of the processes performed by geometric reasoning module 415 of FIG. 4 and/or geometric reasoning module 1215 of FIG. 12. In some embodiments, the process of FIG. 21 is performed by and/or when using a biological language reasoning model such as the model corresponding to or associated with biological language model service 111 of FIG. 1, biological language model service 201 of FIG. 2, biological language model 303 of FIG. 3, and/or biological language model module 401 of FIG. 4. Similarly, in some embodiments, the process of FIG. 21 is performed by a structure encoder such as structure encoder 1303 of FIG. 13 and/or structure encoder 1403 of FIG. 14.

At 2101, state information is received. For example, structure state information including local structure information for a biological object such as a protein is received. The received structure state information can include state sequence information and representations of a local neighboring structure and associated context. For example, for a biological protein object, the state information can include local state information for each amino acid in the protein. The included local information for a specific amino acid can include references to its neighboring amino acids. For example, a list of a specific amino acid's neighbors based on their offsets in the protein sequence can be included in an initial version of the state information received at 2101 such as a version of the state information before it has been updated with geometric attention. In some embodiments, the state information received at 2101 includes local physical structure information such as backbone frames. For a protein object, each included backbone frame can specify an origin and rotation matrix for a specific amino acid based on the backbone atoms of the amino acid. In some embodiments, the local structure information including all atomic coordinates for performing geometric attention on the biological structure. In some embodiments, the state information received at 2101 corresponds to local state information 1901 and backbone frames 1911 of FIG. 19 and/or local state information 2001 and backbone frames 2011 of FIG. 20.

At 2103, a direction attention result is determined. For example, direction attention scores can be determined based on learned direction relationships. When applied to a protein, direction attention scores can be determined based on the relationship between neighboring amino acids with respect to their directions (or orientations). In some embodiments, direction metrics can be determined by taking each pair of specific amino acids of a protein and transforming each into a shared frame of reference before comparing their respective directions. For example, the state information received at 2101 can describe each amino acid in its own frame of reference and further include a set of transformations to apply to transform each amino acid into a shared or global frame of reference. In various embodiments, the direction attention result is determined at least in part by capturing the direction relationship between neighboring amino acids such as the closet K amino acids to each specific amino acid of a protein. In various embodiments, query, key, and value vectors are used to determine a direction attention result. For example, a direction query and direction key vector can be used to determine a direction attention result. In some embodiments, the key vector is applied after the distance attention result determined at 2105 is used to attenuate the direction attention result.

At 2105, a distance attention result is determined. For example, distance attention scores can be determined based on learned distance relationships. When applied to a protein, distance attention scores can be determined based on the relationship between neighboring amino acids with respect to the distance between them. In some embodiments, direction metrics can be determined by taking each pair of specific amino acids of a protein and transforming each into a shared frame of reference before determining the distance between them. For example, the state information received at 2101 can describe each amino acid in its own frame of reference and further include a set of transformations to apply to transform each amino acid into a shared or global frame of reference. In various embodiments, the distance attention result is determined at least in part by capturing the distance relationship between neighboring amino acids such as the closet K amino acids to each specific amino acid of a protein. In various embodiments, query, key, and value vectors are used to determine a distance attention result. For example, a distance query and distance key vector can be used to determine a distance attention result. In some embodiments, the key vector is applied after the distance attention result is used to attenuate the direction attention result determined at 2103.

At 2107, a geometric attention result is determined. For example, a geometric attention result is determined using the direction attention result determined at 2103 and the distance attention result determined at 2105. In some embodiments, learned (or configured) weight terms are applied to the direction and distance attention results and then a weighted distance attention result is used to attenuate a weighted direction attention result. The resulting weighted attention result is normalized such as by applying a softmax function. A value vector is determined and applied to the normalized attention scores to determine a geometric attention result. In various embodiments, transformations are applied to the different elements, such as to the elements of the value vector and the geometric attention result to ensure that computational results are in the appropriate reference context and/or frame of reference. In various embodiments, the computed geometric attention result allows the model to focus on different aspects of local structure using extracted direction and distance features.

At 2109, state information is updated. For example, local state information such as local physical structure information including sequence state information is updated using the geometric attention result determined at 2107. In various embodiments, the updated state information corresponds to the state information received at 2101 updated with the performed geometric reasoning. For example, the geometric attention result can be applied to sequence state information received as local state information and the updated state information can include an updated sequence state with updated weighted sequence representations. In various embodiments, the updated state information can be provided to downstream processing blocks including chained geometric attention blocks.

Figure 22:
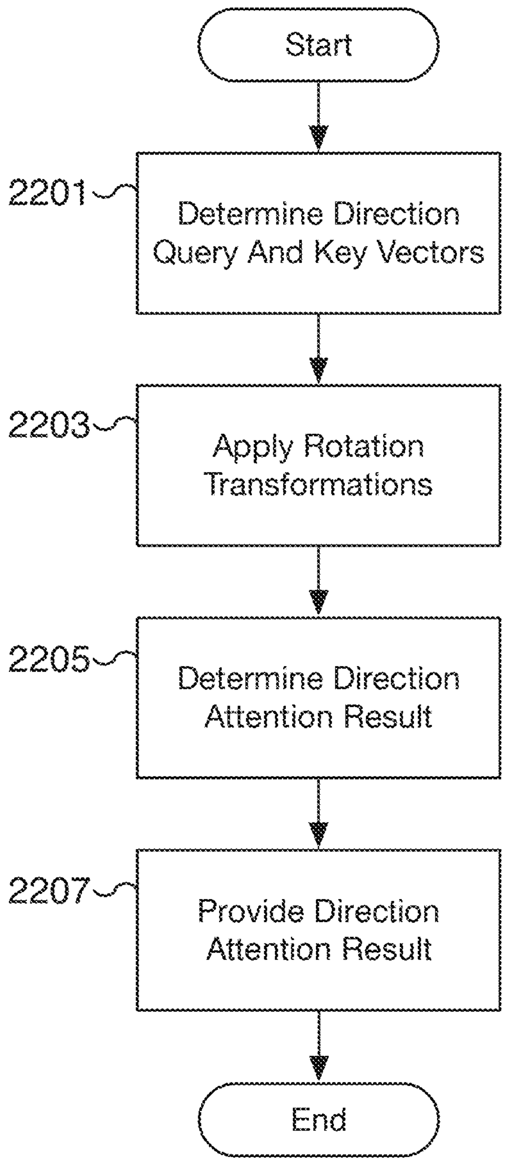
FIG. 22 is a flow chart illustrating an embodiment of a process for determining a direction attention result on biological structure.

FIG. 22 is a flow chart illustrating an embodiment of a process for determining a direction attention result on biological structure. For example, using the process of FIG. 22, a direction attention block of a geometric attention block can determine direction attention scores from local state and structure inputs. In some embodiments, the direction attention scores are intermediate values that are considered along with distance attention scores to determine weighted attention scores. For example, the direction attention result determined using the process of FIG. 22 can be provided to an attention score block of the geometric attention block to determine weighted attention scores and geometric attention scores. In some embodiments, the process of FIG. 22 is performed at 2103 of FIG. 21 by a direction attention block such as direction attention block 1921 of FIG. 19 and/or direction attention block 2021 of FIG. 20.

At 2201, direction query and direction key vectors are determined. For example, using received local state information including local structure context information, direction query and direction key vectors are determined. In some embodiments, the local state information is sequence state information and corresponds to local state information such as local state information 1901 of FIG. 19 and/or local state information 2001 of FIG. 20. In various embodiments, the direction query and direction key vectors are determined using learned weight matrices such as learned weight query and learned weight direction matrices.

At 2203, rotation transformations are applied. For example, using local physical structure information, the direction query and direction key vectors determined at 2201 are transformed to a shared frame of reference such as a global reference frame. In some embodiments, the applied transformations correspond to performing matrix multiplication operations using rotation matrices of the associated frames. For example, received local physical structure information such as backbone frames can include rotation matrices for transforming the respective elements of direction query and direction key vectors to the appropriate shared frame of reference. In some embodiments, the rotation matrices are derived from the backbone frames information, such as from the coordinate axes and/or origin coordinates of each backbone frame depending on the frame format. In some embodiments, the applied rotation transformations correspond to computational operations 2031 and 2033 of FIG. 20.

At 2205, a direction attention result is determined. For example, the transformed direction query and direction key vectors are compared to determine a direction attention result. In some embodiments, the direction attention result includes multiple direction attention scores by computing a direction attention score between each element and all other corresponding elements in the sequence. For example, a direction attention score for an element can be computed by performing a dot product operation on the corresponding direction query vector and direction key vector elements.

At 2207, the direction attention result is provided. For example, the direction attention result is provided to an attention score block where the direction attention result can be eventually evaluated with a value vector. In some embodiments, the direction attention result can be an intermediate result that is considered along with a distance attention result to determine a weighted attention result. Along with additional attention score processing steps, a normalized weighted attention result can be evaluated with a value vector to determine a geometric attention result. In some embodiments, the attention score block receiving the direction attention result is attention score block 1925 of FIG. 19 and/or attention score block 2025 of FIG. 20.

Figure 23:
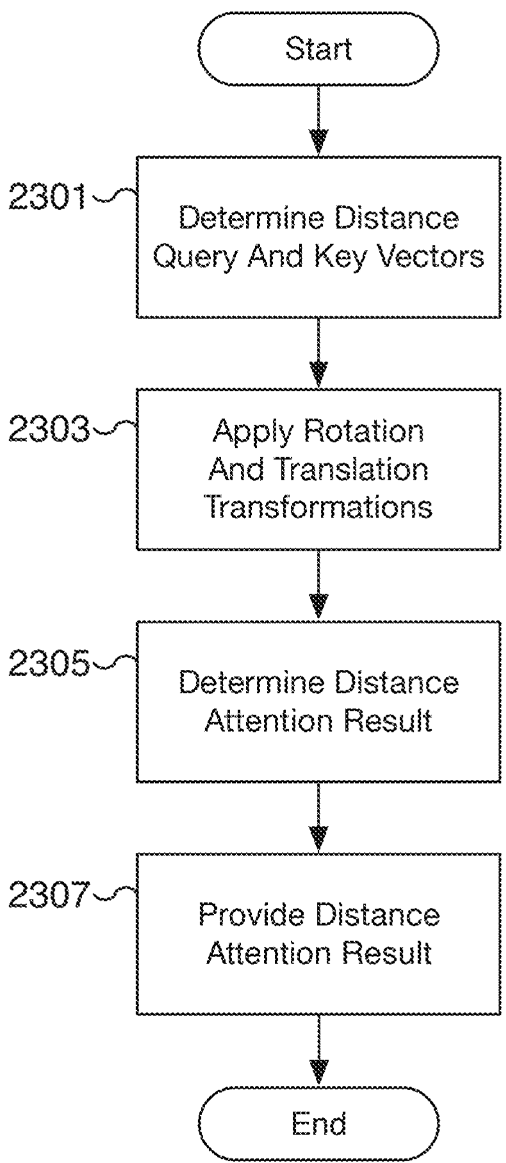
FIG. 23 is a flow chart illustrating an embodiment of a process for determining a distance attention result on biological structure.

FIG. 23 is a flow chart illustrating an embodiment of a process for determining a distance attention result on biological structure. For example, using the process of FIG. 23, a distance attention block of a geometric attention block can determine distance attention scores from local state and structure inputs. In some embodiments, the distance attention scores are intermediate values that are considered along with direction attention scores to determine weighted attention scores. For example, the distance attention result determined using the process of FIG. 23 can be provided to an attention score block of a geometric attention block to determine weighted attention scores and geometric attention scores. In some embodiments, the process of FIG. 23 is performed at 2105 of FIG. 21 by a distance attention block such as distance attention block 1923 of FIG. 19 and/or distance attention block 2023 of FIG. 20. In various embodiments, the process of FIG. 23 is similar to the process of FIG. 22 but used to perform distance attention scores.

At 2301, distance query and distance key vectors are determined. For example, using received local state information including local structure context information, distance query and distance key vectors are determined. In some embodiments, the local state information is sequence state information and corresponds to local state information such as local state information 1901 of FIG. 19 and/or local state information 2001 of FIG. 20. In various embodiments, the distance query and distance key vectors are determined using learned weight matrices such as learned weight query and learned weight distance matrices.

At 2303, rotation and translation transformations are applied. For example, using local physical structure information, the distance query and distance key vectors determined at 2301 are transformed to a shared frame of reference such as a global reference frame. In some embodiments, the applied transformations correspond to performing matrix multiplication and addition operations using rotation matrices and translation vectors, respectively, of the associated frames. For example, received local physical structure information such as backbone frames can include rotation matrices and translation vectors for transforming the respective elements of a distance query and distance key vectors to the appropriate shared frame of reference. In some embodiments, the rotation matrices and translation vectors are derived from the backbone frames information, such as from the coordinate axes and/or origin coordinates of each backbone frame depending on the frame format. In some embodiments, the applied rotation and translation transformations correspond to computational operations 2041 and 2043 of FIG. 20.

At 2305, a distance attention result is determined. For example, the transformed distance query and distance key vectors are compared to determine a distance attention result. In some embodiments, the distance attention result includes multiple distance attention scores by computing a distance attention score between each element and all other corresponding elements in the sequence. For example, a distance attention score for an element can be computed by performing a Euclidean norm operation with the corresponding distance query vector and distance key vector elements.

At 2307, the distance attention result is provided. For example, the distance attention result is provided to an attention score block where the distance attention result can be eventually evaluated with a value vector. In some embodiments, the distance attention result can be an intermediate result that is considered along with a direction attention result to determine a weighted attention result. Along with additional attention score processing steps, a normalized weighted attention result can be evaluated with a value vector to determine a geometric attention result. In some embodiments, the attention score block receiving the distance attention result is attention score block 1925 of FIG. 19 and/or attention score block 2025 of FIG. 20.

Figure 24:
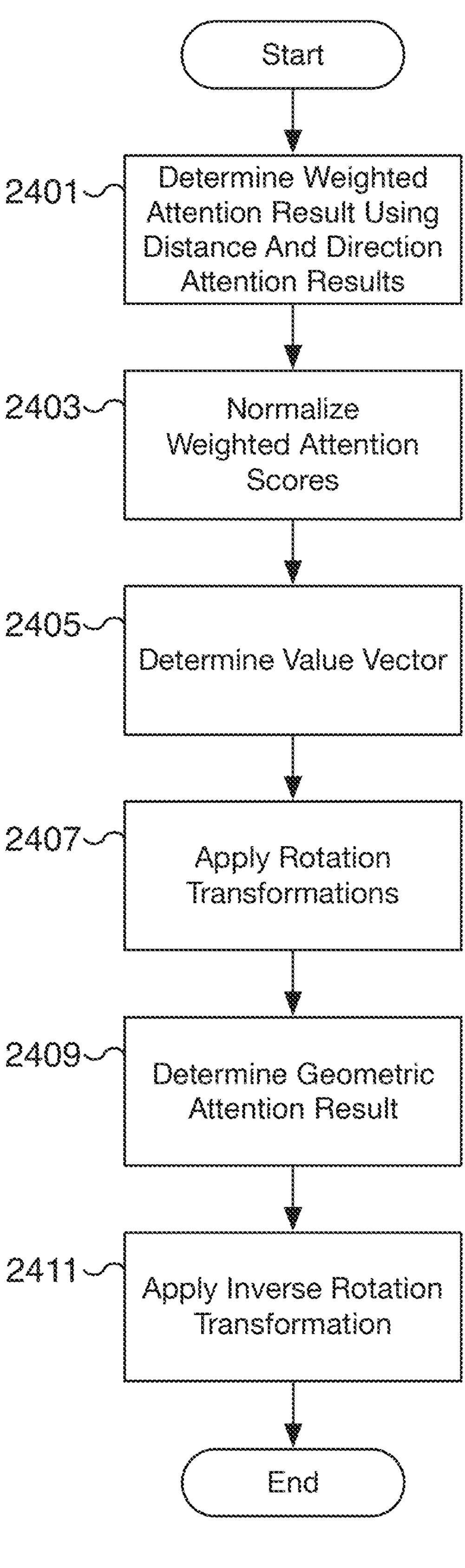
FIG. 24 is a flow chart illustrating an embodiment of a process for determining a geometric attention result on biological structure from direction and distance attention results.

FIG. 24 is a flow chart illustrating an embodiment of a process for determining a geometric attention result on biological structure from direction and distance attention results. For example, using the process of FIG. 24, an attention score block of a geometric attention block can determine geometric attention scores from local state and structure, direction attention, and distance attention inputs. In some embodiments, the geometric attention scores are based on weighted direction attention scores that are attenuated by weighted distance attention scores. For example, the process of FIG. 24 can attenuate the direction attention result determined using the process of FIG. 22 by the distance attention result determined using the process of FIG. 23 prior to applying a value vector to determine a geometric attention result. In some embodiments, the process of FIG. 24 is performed at 2107 of FIG. 21 by an attention score block such as attention score block 1925 of FIG. 19 and/or attention score block 2025 of FIG. 20. In various embodiments, the process of FIG. 24 is combined with at least the processes of FIGS. 22 and 23 to determine a geometric attention result.

At 2401, a weighted attention result is determined using distance and direction attention results. For example, a weighted attention result is determined based on a weighted attention result and a weighted distance result. The intermediate weighted direction attention and intermediate weighted distance attention results can be determined by applying learned and/or configured direction and distance term weights, respectively, to the direction attention and distance attention results. The intermediate weighted distance result scores are then subtracted from the intermediate weighted direction result scores to determine a weighted attention result. For example, for a particular element of a weighted attention result, a weighted attention score for $element_{ij}$ can be determined with weighted attention result computation 2051 by computing $element_{ij}$=weight_direction*direction_term-weight_distance*distance_term. In some embodiments, the operations performed to determine the weighted attention result at 2401 correspond to computational operation 2051 of FIG. 20.

At 2403, weighted attention scores are normalized. For example, the weighted attention result determined at 2401 is normalized into a valid probability distribution. In some embodiments, a softmax function is utilized to normalize the weighted attention scores of the weighted attention result. The normalized weighted attention scores can be evaluated with a value vector. In some embodiments, the normalization operations performed on weighted attention scores correspond to the softmax functional module shown in FIG. 20.

At 2405, a value vector is determined. For example, a value vector is determined using received local state information including local structure context information. In some embodiments, the local state information is sequence state information and corresponds to local state information such as local state information 1901 of FIG. 19 and/or local state information 2001 of FIG. 20. In various embodiments, the value vector is determined using a learned weight matrix such as a learned weight key matrix.

At 2407, rotation transformations are applied. For example, using local physical structure information, the value vector determined at 2405 is transformed to a shared frame of reference as the normalized weighted attention scores determined at 2403. In some embodiments, the applied transformations correspond to performing matrix multiplication operations using rotation matrices of the associated frames. For example, received local physical structure information such as backbone frames can include rotation matrices for transforming the respective elements of the value vector to the appropriate reference frame. In some embodiments, the rotation matrices are derived from the backbone frames information, such as from the coordinate axes and/or origin coordinates of each backbone frame depending on the frame format. In some embodiments, the rotation transformations applied at 2407 correspond to computational operation 2053 of FIG. 20.

At 2409, a geometric attention result is determined. For example, the transformed value vector from step 2407 is evaluated with the normalized weighted attention result from step 2403 to determine a geometric attention result. In some embodiments, the geometric attention result is determined by applying a matrix multiplication operation. In some embodiments, the matrix multiplication operation performed to determine the geometric attention result at 2409 corresponds to computational operation 2055 of FIG. 20.

At 2411, an inverse rotation transformation is applied. For example, an inverse rotation transformation is applied to the geometric attention result determined at 2409 to transform the geometric attention result into the appropriate frame of reference. In various embodiments, the rotation transformation applied at 2411 corresponds to the inverse of the rotation transformation applied at 2407. In some embodiments, the inverse rotation transformation applied at 2411 corresponds to computational operation 2055 of FIG. 20. In various embodiments, the transformed geometric attention result can be used to update the state information.

Figure 25:
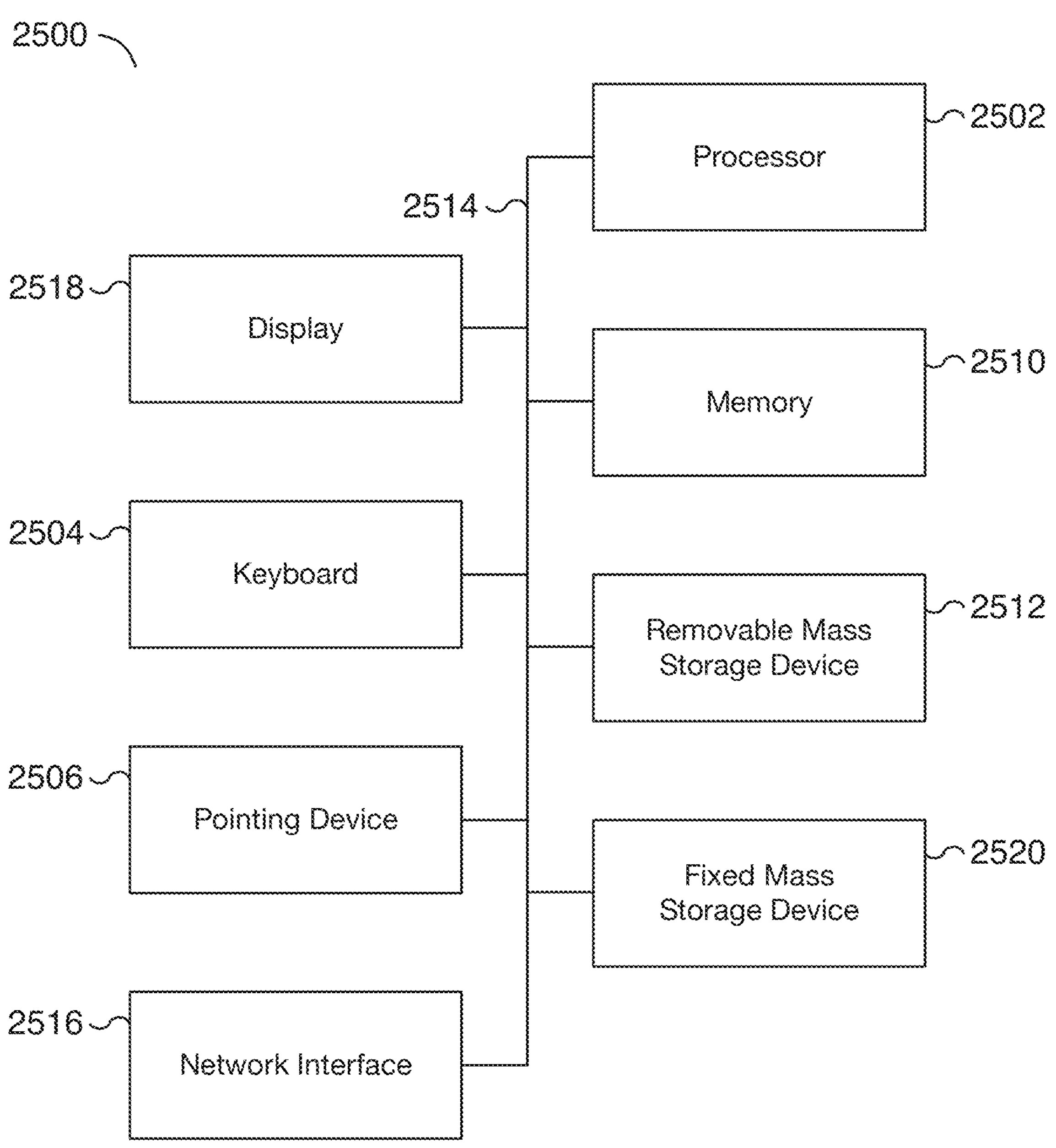
FIG. 25 is a functional diagram illustrating a programmed computer system for performing biological language reasoning.

FIG. 25 is a functional diagram illustrating a programmed computer system for performing biological language reasoning. As will be apparent, other computer system architectures and configurations can be utilized for performing biological language reasoning including those with one or more graphical processing units (GPUs). Examples of computer system 2500 include clients 101, 103, and 105 of FIG. 1, one or more computers of biological language model service 111 of FIG. 1, and/or one or more computers of biological language model service 201 of FIG. 2. Additional examples of computer system 2500 include one or more computers used to implement biological language model 303 of FIG. 3, biological language model module 401 of FIG. 4, multi-track biological protein language model 503 of FIG. 5, transformer block with a geometric attention 603 of FIG. 6, biological structure tokenizer module 1201 of FIG. 12, structure tokenizer 1300 of FIG. 13, structure encoder 1403 of FIG. 14, geometric reasoning block 1503 of FIG. 15, geometric attention block 1903 of FIG. 19, and/or geometric attention block 2003 of FIG. 20. Computer system 2500, which includes various subsystems as described below, includes at least one microprocessor subsystem (also referred to as a processor or a central processing unit (CPU)) 2502. For example, processor 2502 can be implemented by a single-chip processor or by multiple processors. In some embodiments, processor 2502 is a general purpose digital processor that controls the operation of the computer system 2500. Using instructions retrieved from memory 2510, the processor 2502 controls the reception and manipulation of input data, and the output and display of data on output devices (e.g., display 2518). In various embodiments, one or more instances of computer system 2500 can be used to implement at least portions of the processes of FIGS. 7-11, 16-18, and/or 21-24.

Processor 2502 is coupled bi-directionally with memory 2510, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 2502. Also as is well known in the art, primary storage typically includes basic operating instructions, program code, data and objects used by the processor 2502 to perform its functions (e.g., programmed instructions). For example, memory 2510 can include any suitable computer-readable storage media, described below, depending on whether, for example, data access needs to be bi-directional or unidirectional. For example, processor 2502 can also directly and very rapidly retrieve and store frequently needed data in a cache memory (not shown).

A removable mass storage device 2512 provides additional data storage capacity for the computer system 2500, and is coupled either bi-directionally (read/write) or unidirectionally (read only) to processor 2502. For example, storage 2512 can also include computer-readable media such as magnetic tape, flash memory, PC-CARDS, portable mass storage devices, holographic storage devices, and other storage devices. A fixed mass storage 2520 can also, for example, provide additional data storage capacity. The most common example of mass storage 2520 is a hard disk drive. Mass storages 2512, 2520 generally store additional programming instructions, data, and the like that typically are not in active use by the processor 2502. It will be appreciated that the information retained within mass storages 2512 and 2520 can be incorporated, if needed, in standard fashion as part of memory 2510 (e.g., RAM) as virtual memory.

In addition to providing processor 2502 access to storage subsystems, bus 2514 can also be used to provide access to other subsystems and devices. As shown, these can include a display monitor 2518, a network interface 2516, a keyboard 2504, and a pointing device 2506, as well as an auxiliary input/output device interface, a sound card, speakers, and other subsystems as needed. For example, the pointing device 2506 can be a mouse, stylus, track ball, or tablet, and is useful for interacting with a graphical user interface.

The network interface 2516 allows processor 2502 to be coupled to another computer, computer network, or telecommunications network using a network connection as shown. For example, through the network interface 2516, the processor 2502 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 2502 can be used to connect the computer system 2500 to an external network and transfer data according to standard protocols. For example, various process embodiments disclosed herein can be executed on processor 2502, or can be performed across a network such as the Internet, intranet networks, or local area networks, in conjunction with a remote processor that shares a portion of the processing. Additional mass storage devices (not shown) can also be connected to processor 2502 through network interface 2516.

An auxiliary I/O device interface (not shown) can be used in conjunction with computer system 2500. The auxiliary I/O device interface can include general and customized interfaces that allow the processor 2502 to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 25 is but an example of a computer system suitable for use with the various embodiments disclosed herein. Other computer systems suitable for such use can include additional or fewer subsystems. In addition, bus 2514 is illustrative of any interconnection scheme serving to link the subsystems. Other computer architectures having different configurations of subsystems can also be utilized.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:

receiving, by one or more processors, a protein query including backbone coordinate data representing three-dimensional local structure of a protein, and generating a sequence state including representations of neighboring amino acids included in a local physical structure for a specific amino acid of the protein, wherein the neighboring amino acids at least include a first neighboring amino acid and a second neighboring amino acid, and the neighboring amino acids are specifically selected for the specific amino acid based on being physically closest in to the specific amino acid in a three-dimensional space based on the backbone coordinate data;

determining, using a geometric attention block of a biological protein language model trained to predict elements of protein sequence, structure, and/or function, comprising a plurality of transformer blocks, the geometric attention block comprising a direction attention block and a distance attention block:

determining, by the direction attention block, a direction query vector and a direction key vector by applying a first directional rotation transformation derived from a local backbone reference frame associated with the first neighboring amino acid to at least a portion of a representation of the first neighboring amino acid included in the representations and applying a second directional rotation transformation derived from a local backbone reference frame associated with the second neighboring amino acid to at least a portion of a representation of the second neighboring amino acid included in the representations;

determining, by the direction attention block, a direction attention result including by performing a dot product operation on the direction query vector and the direction key vector; and determining, by the distance attention block, a distance attention result by performing a Euclidean norm operation based on representations of the first neighboring amino acid and the second neighboring amino acid that have been transformed into a common reference frame;

using at least the direction attention result and the distance attention result to update the sequence state within the geometric attention block of the biological protein language model to generate an updated sequence state; and predicting, by the biological protein language model using the updated sequence state a structural property of the protein, wherein the structure property is represented as a structure token corresponding to the specific amino acid.

2. The method of claim 1, further comprising determining a weighted direction attention result including by applying a learned direction weight term to the determined direction attention result.

3. The method of claim 1, further comprising:

determining a distance query vector and a distance key vector including by applying a first distance rotation transformation and a first distance translation transformation to at least the portion of the representation of the first neighboring amino acid included in the representations and applying a second distance rotation transformation and a second distance translation transformation to at least the portion of the representation of the second neighboring amino acid included in the representations;

determining a distance attention result including by evaluating the elements of the distance query vector and the distance key vector; and using at least the distance attention result to update the sequence state for an attention mechanism of the biological protein language model.

4. The method of claim 3, wherein the first direction rotation transformation and the first distance rotation transformation are the same; and wherein the second direction rotation transformation and the second distance rotation transformation are the same.

5. The method of claim 3, further comprising determining a weighted distance attention result including by applying a learned distance weight term to the determined direction attention result.

6. The method of claim 3, further comprising:

determining a weighted attention result including by subtracting a weighted distance attention result from a weighted direction attention result.

7. The method of claim 6, further comprising:

determining a value vector including by applying a first value rotation transformation to at least the portion of the representation of the first neighboring amino acid included in the representations and applying a second value rotation transformation to at least the portion of the representation of the second neighboring amino acid included in the representations;

determining a geometric attention result including by applying a matrix multiplication operation using the value vector and the weighted attention result as operands;

applying inverse rotation transformations to the determined geometric attention result; and using at least the determined geometric attention result to update the sequence state for an attention mechanism of the biological protein language model.

8. The method of claim 7, wherein at least a subset of the applied inverse rotation transformations has an inverse relationship with the first value rotation transformation and the second value rotation transformation.

9. A system, comprising:

one or more processors configured to:

receive a protein query including backbone coordinate data representing three-dimensional local structure of a protein, and generate a sequence state including representations of neighboring amino acids included in a local physical structure for a specific amino acid of the protein, wherein the neighboring amino acids at least include a first neighboring amino acid and a second neighboring amino acid, and the neighboring amino acids are specifically selected for the specific amino acid based on being physically closest in to the specific amino acid in a three-dimensional space based on the backbone coordinate data;

determine, using a geometric attention block of a biological protein language model trained to predict elements of protein sequence, structure, and/or function, comprising a plurality of transformer blocks, the geometric attention block comprising a direction attention block and a distance attention block:

determine, by the direction attention block, a direction query vector and a direction key vector including by being configured to apply a first directional rotation transformation derived from a local backbone reference frame associated with the first neighboring amino acid to at least a portion of a representation of the first neighboring amino acid included in the representations and applying a second directional rotation transformation derived from a local backbone reference frame associated with the second neighboring amino acid to at least a portion of a representation of the second neighboring amino acid included in the representations;

determine, by the direction attention block, a direction attention result including by performing a dot product operation on the direction query vector and the direction key vector; and determine, by the distance attention block, a distance attention result by performing a Euclidean norm operation based on representations of the first neighboring amino acid and the second neighboring amino acid that have been transformed into a common reference frame;

use at least the direction attention result and the distance attention result to update the sequence state within the geometric attention block of the biological protein language model to generate an updated sequence state; and predict, by the biological protein language model using the updated sequence state a structural property of the protein, wherein the structure property is represented as a structure token corresponding to the specific amino acid; and a memory coupled to at least one of the one or more processors and configured to provide instructions.

10. The system of claim 9, wherein the one or more processors are configured to:

determine a weighted direction attention result including by applying a learned direction weight term to the determined direction attention result.

11. The system of claim 9, wherein the one or more processors are configured to:

determine a distance query vector and a distance key vector including by applying a first distance rotation transformation and a first distance translation transformation to at least the portion of the representation of the first neighboring amino acid included in the representations and applying a second distance rotation transformation and a second distance translation transformation to at least the portion of the representation of the second neighboring amino acid included in the representations;

determine a distance attention result including by evaluating the elements of the distance query vector and the distance key vector; and update the sequence state for an attention mechanism of the biological protein language model using at least the distance attention result.

12. The system of claim 11, wherein the first direction rotation transformation and the first distance rotation transformation are the same; and wherein the second direction rotation transformation and the second distance rotation transformation are the same.

13. The system of claim 11, wherein the one or more processors are configured to:

determine a weighted distance attention result including by applying a learned distance weight term to the determined direction attention result.

14. The system of claim 11, wherein the one or more processors are configured to:

determine a weighted attention result including by being configured to subtract a weighted distance attention result from a weighted direction attention result.

15. The system of claim 14, wherein the one or more processors are configured to:

determine a value vector including by being configured to apply a first value rotation transformation to at least the portion of the representation of the first neighboring amino acid included in the representations and applying a second value rotation transformation to at least the portion of the representation of the second neighboring amino acid included in the representations;

determine a geometric attention result including by being configured to apply a matrix multiplication operation using the value vector and the weighted attention result as operands;

apply inverse rotation transformations to the determined geometric attention result; and update the sequence state for an attention mechanism of the biological protein language model using at least the determined geometric attention result.

16. A computer program product, the computer program product being embodied in a non-transitory computer readable storage medium and comprising computer instructions for:

receiving, by one or more processors, a protein query including backbone coordinate data representing three-dimensional local structure of a protein, and generating a sequence state including representations of neighboring amino acids included in a local physical structure for a specific amino acid of the protein, wherein the neighboring amino acids at least include a first neighboring amino acid and a second neighboring amino acid, and the neighboring amino acids are specifically selected for the specific amino acid based on being physically closest in to the specific amino acid in a three-dimensional space based on the backbone coordinate data;

determining, using a geometric attention block of a biological protein language model trained to predict elements of protein sequence, structure, and/or function, comprising a plurality of transformer blocks, the geometric attention block comprising a direction attention block and a distance attention block:

determining, by the direction attention block, a direction query vector and a direction key vector by applying a first directional rotation transformation derived from a local backbone reference frame associated with the first neighboring amino acid to at least a portion of a representation of the first neighboring amino acid included in the representations and applying a second directional rotation transformation derived from a local backbone reference frame associated with the second neighboring amino acid to at least a portion of a representation of the second neighboring amino acid included in the representations;

determining, by the direction attention block, a direction attention result including by performing a dot product operation on the direction query vector and the direction key vector; and determining, by the distance attention block, a distance attention result by performing a Euclidean norm operation based on representations of the first neighboring amino acid and the second neighboring amino acid that have been transformed into a common reference frame;

using at least the direction attention result and the distance attention result to update the sequence state within the geometric attention block of the biological protein language model to generate an updated sequence state; and predicting, by the biological protein language model using the updated sequence state a structural property of the protein, wherein the structure property is represented as a structure token corresponding to the specific amino acid.

* * * * *